United States Patent
Smyth et al.

(10) Patent No.: US 11,788,148 B2
(45) Date of Patent: Oct. 17, 2023

(54) PROGNOSTIC AND TREATMENT RESPONSE PREDICTIVE METHOD

(71) Applicants: The Institute of Cancer Research: Royal Cancer Hospital, London (GB); The Royal Marsden NHS Foundation Trust, London (GB); National University of Singapore, Singapore (SG)

(72) Inventors: Elizabeth Smyth, Cambridge (GB); Anguraj Sadanandam, London (GB); Gift Nyamundanda, Sutton (GB); David Cunningham, London (GB); Boon Ooi Patrick Tan, Singapore (SG)

(73) Assignees: The Institute of Cancer Research: Royal Cancer Hospital, London (GB); The Royal Marsden NHS Foundation Trust, London (GB); National University of Singapore, Singapore (SG)

(*) Notice: Subject to any disclaimer, the term of this patent is extended or adjusted under 35 U.S.C. 154(b) by 267 days.

(21) Appl. No.: 16/755,085

(22) PCT Filed: Oct. 12, 2018

(86) PCT No.: PCT/SG2018/050514
§ 371 (c)(1),
(2) Date: Apr. 9, 2020

(87) PCT Pub. No.: WO2019/074445
PCT Pub. Date: Apr. 18, 2019

(65) Prior Publication Data
US 2020/0239968 A1    Jul. 30, 2020

(30) Foreign Application Priority Data
Oct. 12, 2017 (GB) ..................... 1716712

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01);
(Continued)

(58) Field of Classification Search
CPC ............ C12Q 1/6886; C12Q 2600/106; C12Q 2600/118; C12Q 2600/158; G01N 2800/50; G01N 2800/52; G01N 2800/7028
See application file for complete search history.

(56) References Cited

U.S. PATENT DOCUMENTS

2013/0064901 A1    3/2013    Tan et al.

FOREIGN PATENT DOCUMENTS

| EP | 2711704 A1 | 3/2014 |
| WO | WO 2004/111603 A2 | 12/2004 |
| WO | WO 2015/033172 | 3/2015 |

OTHER PUBLICATIONS

Yang, Y. et al. Oncology Reports 30:596-614. (Year: 2013).*
(Continued)

*Primary Examiner* — Diana B Johannsen
(74) *Attorney, Agent, or Firm* — Klarquist Sparkman, LLP

(57) ABSTRACT

The present invention provides a method for predicting the treatment response of a human gastroesophageal cancer patient, the method comprising: a) measuring the gene expression of at least 3 of the following genes: CDH1, CDK6, COX2, ELOVL5, GATA4, EGFR, TBCEL, FGF7, CDH17, FNBP1, PIP5K1B, TWIST, CD44, MET, CEACAM1, TOX3, GLIPR2, GSTP1, RON, TMEM136, MYB, BRCA2, FGF1, POU5F1, EPR, DPYD, ABL2 and SH3RF1 in a sample obtained from the gastroesophageal
(Continued)

Predicted risk using seven significant genes tumour of the patient to obtain a sample gene expression profile of at least said genes; and b) making a prediction of the treatment response and/or prognosis of the patient based on the sample gene expression profile. Also provided are related computer-implemented methods and methods of treatment of gastroesophageal cancer.

1 Claim, 12 Drawing Sheets

(52) U.S. Cl.
CPC ... *C12Q 2600/158* (2013.01); *G01N 2800/52* (2013.01); *G01N 2800/7028* (2013.01)

(56) References Cited

OTHER PUBLICATIONS

Murphy, A. and Kelly, R.J. Gastroenterology Research and Practice, vol. 2015, Article ID 896560, 11 pages. (Year: 2015).*
Tan, I.B. et al. Gastroenterology 141:476-485. (Year: 2011).*
Ray, P.S. et al. Annals of Surgical Oncology 17(Suppl. 1);S80, Abstract No. P143. (Year: 2010).*
"100. Jahrestagung der Deutschen Gesellschaft für Pathologie e.V.," *Pathologe, Berlin, DE*, vol. 37, No. 1, pp. S3-S156, 2016; Abstract P01.10, p. S93.
Akiyama et al., "*GATA-4* and *GATA-5* Transcription Factor Genes and Potential Downstream Antitumor Target Genes are Epigenetically Silenced in Colorectal and Gastric Cancer," *Molecular and Cellular Biology*, vol. 23, No. 23, pp. 8429-8439, 2003.
Akutsu et al., "COX2 Expression Predicts Resistance to Chemotherapy in Esophageal Squamous Cell Carcinoma," *Ann. Surg. Oncol.*, vol. 18, pp. 2946-2951, 2011.
Kim et al., "Comparative analysis of protein expressions in primary and metastatic gastric carcinomas," *Human Pathology*, vol. 40, pp. 314-322, 2009.
Kim et al., "DNA microarray analysis of the correlation between gene expression patterns and acquired resistance to 5-FU/cisplatin in gastric cancer," *Biochemical and Biophysical Research Communications*, vol. 316, pp. 781-789, 2004.
Kim et al., "Three-gene predictor of clinical outcome for gastric cancer patients treated with chemotherapy," *The Pharmacogenomics Journal*, vol. 12, No. 2, pp. 119-127, 2012.
Luber et al., "Biomarker analysis cetuximab plus oxaliplatin/leucovorin/5-fluorouracil in first-line metastatic gastric and oesophagogastric junction cancer: results from a phase II trial of the Arbeitsgemeinschaft Internistische Onkologie (AIO)," *BMC Cancer*, 11:509, 2011 (10 pages).
Phipps et al., "Common genetic variation and survival after colorectal cancer diagnosis: a genome-wide analysis," *Carcinogenesis*, vol. 37, No. 1, pp. 87-95, 2016.
Szasz et al., "Cross-validation of survival associated biomarkers in gastric cancer using transcriptomic data of 1,065 patients," *Oncotarget*, vol. 7, No. 31, pp. 49322-49333, 2016.
Takada et al., "Screening of DNA copy-number aberrations in gastric cancer cell lines by array-based comparative genomic hybridization," *Cancer Sci.*, vol. 96, No. 2, pp. 100-110, 2005.
Ahn et al., "FGR2 in gastric cancer: protein overexpression predicts gene amplification and high H-index predicts poor survival," *Modern Pathology*, vol. 29, p. 1095-1103 (2016).
An et al., "Microsatellite instability in sporadic gastric cancer: its prognostic role and guidance for 5-FU based chemotherapy after R0 resection," *Int. J. Cancer*, vol. 131 (2), p. 505-511 (2012).
Alderson et al., "Neoadjuvant chemotherapy for resectable oesophageal and junctional adenocarcinoma: Results from the UK Medical Research Council randomized OEO5 trial (ISRCTN 01852072)" *ASCO Meeting Abstracts*, vol. 33 (15_suppl), p. 4002 (2015).

Bang et al., "Adjuvant capecitabine and oxaliplatin for gastric cancer after D2 gastrectomy (Classic): a phase 3 open-label, randomized controlled trial," Lancet, vol. 379 (9813), p. 315-321 (2012).
Beghelli et al., "Microsatellite instability in gastric cancer is associated with better prognosis in only stage II cancers," *Surgery*, vol. 139 (3), p. 347-356 (2006).
Birkman et al., "EGFR gene amplification is relatively common and associates with outcome in intestinal adenocarcinoma of the stomach, gastro-oesophageal junction and distal oesophagus," *BMC Cancer*, 16:406 (2016).
Blok et al., "Loss of E-cadherin expression in early gastric cancer," *Histopathology*, vol. 34 (5), p. 410-415 (1999).
Choi et al., "Analysis of MET mRNA expression in gastric cancers using RNA in situ hybridization assay: its clinical implication and comparison with immunohistochemistry and silver in situ hybridization," *PLos One*, vol. 9 (11), e111658 (2014).
The Cancer Genome Atlas Network, "Comprehensive molecular characterization of gastric adenocarcinoma," *Nature*, vol. 513 (7517), p. 202-209 (2014).
The Cancer Genome Atlas Network, "Integrated genomic characterization of oesophageal carcinoma," *Nature*, vol. 541, p. 169-190 (2017).
Cristescu et al., "Molecular analysis of gastric cancer identifies subtypes associated with distinct clinical outcomes," *Nat. Med.*, vol. 21 (5), p. 449-456 (2015).
Cunningham et al., "Perioperative Chemotherapy versus Surgery Alone for Resectable Gastroesophageal Cancer," *New England Journal of Medicine*, vol. 355 (1), p. 11-20 (2006).
Cunningham et al., "Peri-operative chemotherapy ± bevacizumab for resectable gastro-oesophageal adenocarcinoma: Results from the UK Medical Research Council randomized ST03 trial (ISRCTN 46020948)," *European Journal of Cancer*, vol. 51, p. S400 (2015).
Cunningham et al., "Phase III, randomized, double-blind, multicenter, placebo (P)-controlled trial of rilotumumab (R) plus epirubicin, cisplatin and capecitabine (ECX) as first-tine therapy in patients (pts) with advanced MET-positive (pos) gastric or gastroesophageal junction (G/GEJ) cancer: RILOMET-1 study," *ASCO Meeting Abstracts*, vol. 33 (15_suppl), p. 4000 (2015).
Deng et al., "A comprehensive survey of genomic alterations in gastric cancer reveals systematic patterns of molecular exclusivity and co-occurrence among distinct therapeutic targets," *Gut*, vol. 61, p. 673-684 (2012).
Fareed et al., "Tumor regression grade (TRG) analyses in patients with resectable gastro-oesophageal adenocarcinomas treated with platinum-based neoadjuvant chemotherapy," *Histopathology*, vol. 55 (4), p. 399-406 (2009).
Findlay et al., "A systematic review and meta-analysis of somatic and germline DNA sequence biomarkers of esophageal cancer survival, therapy response and stage," *Ann. Oncol.*, vol. 26 (4), p. 624-644 (2015).
Flucke et al., "Differences between biopsy- or specimen-related Lauren and World Health Organization classification in gastric cancer," *World J. Surg.*, vol. 26 (2), p. 137-140 (2002).
Goekkurt et al., "Polymorphisms of glutathione S-transferases (GST) and thymidylate synthase (TS)—novel predictors for response and survival in gastric cancer patients," *Br. J. Cancer*, vol. 94 (2), p. 281-286 (2006).
Goff et al., "Thymidylate synthase genotype-directed chemotherapy for patients with gastric and gastroesophageal junction cancers," *PLoS One*, vol. 9 (9), e107424 (2014).
Han et al., "Evaluation of Fibroblast Growth Factor Receptor 2 Expression, Heterogeneity and Clinical Significance in Gastric Cancer," *Pathobiology*, vol. 85 (6), p. 269-279 (2015).
Higaki et al., "Gene copy number gain of EGFR is a poor prognostic biomarker in gastric cancer: evaluation of 855 patients with brightfield dual in situ hybridization (Dish) method," *Gastric Cancer*, vol. 19(1), p. 63-73 (2016).
Ivanova et al., "Integrated epigenomics identifies BMP4 as a modulator of cisplatin sensitivity in gastric cancer," *Gut*, vol. 62 (1), p. 22-33 (2013).

(56) References Cited

OTHER PUBLICATIONS

Janbabi et al., "The prognostic impact of EGFR, ErbB2 and MET gene amplification in human gastric carcinomas as measured by quantitative Real-Time PCR," *J. Cancer Res. Clin. Oncol.*, vol. 141 (11), p. 1945-1952 (2015).
Kattan et al., "Postoperative Nomogram for Disease-Specific Survival After an R0 Resection for Gastric Carcinoma," *Journal of Clinical Oncology*, vol. 21 (19), p. 3647-3650 (2003).
Kim et al., "Heterogeneous amplification of ERBB2 in primary lesions is responsible for the discordant ERBB2 status of primary and metastatic lesions in gastric carcinoma," *Histopathology*, vol. 59 (5), p. 822-831 (2011).
Kim et al., "The benefit of microsatellite instability is attenuated by chemotherapy in stage II and stage 111 gastric cancer: Results from a large cohort with subgroup analyses," *Int. J. Cancer*, vol. 137 (4), p. 819-825 (2015).
Kim et al., "Prognostic implications of tumor-infiltrating FoxP3+ regulatory T cells and CD8+ cytotoxic T cells in microsatellite-unstable gastric cancers," *Hum. Pathol.*, vol. 45 (2), p. 285-293 (2014).
Lei et al., "Identification of molecular subtypes of gastric cancer with different responses to PI3-kinase inhibitors and 5-flurorouracil," *Gastroenterology*, vol. 145 (3), p. 554-565 (2013).
Lin et al., "Signatures of tumour immunity distinguish Asian and non-Asian gastric adenocarcinomas," *Gut*, vol. 64, p. 1721-1731 (2014).
Liu et al., "Influences of ERCC1, ERCC2, XRCC1, GSTP1, GSTT1, and MTHFR polymorphisms on clinical outcomes in gastric cancer patients treated with EOF chemotherapy," *Tumor Biol.*, vol. 37 (2), p. 1753-1762 (2016).
MacDonald et al., "Chemoradiotherapy after surgery compared with surgery alone for adenocarcinoma of the stomach or gastroesophageal junction," *New England Journal of Medicine*, vol. 345 (10), p. 725-730 (2001).
Metzger et al., "ERCC1 mRNA levels complement thymidylate synthase mRNA levels in predicting response and survival for gastric cancer patients receiving combination cisplatin and fluorouracil chemotherapy," *J. Clin. Oncol.*, vol. 16 (1), p. 309-316 (1998).
Ming "Gastric carcinoma, a pathological classification," *Cancer*, vol. 39 (6), p. 2475-2485 (1977).
Napieralski et al., "Methylation of tumor-related genes in neoadjuvant-treated gastric cancer: relation to therapy response and clinicopathologic and molecular features," *Clin Cancer Res*, vol. 13 (17), p. 5095-5102 (2007).
Noh et al., "Adjuvant capecitabine plus oxaliplatin for gastric cancer after D2 gastrectomy (Classic): 5-year follow-up of an open-label, randomized phase 3 trial," *Lancet Oncol.*, vol. 15 (12), p. 1389-1396 (2014).
Novotny et al., "Predicting individual survival after gastric cancer resection: Validation of a U.S.-derived nomogram at a single high-volume center in Europe," *Ann Surg*, vol. 243 (1), p. 74-81 (2006).
Ohtsu et al., "Bevacizumab in combination with chemotherapy as first-line therapy in advanced gastric cancer: a randomized, double-blind, placebo-controlled phase III study," *J. Clin. Oncol.*, vol. 29 (30), p. 3968-3976 (2011).
Okines et al., "Biomarker analysis in oesophagogastric cancer: Results from the REAL3 and TransMAGIC trials," *Eur. J. Cancer*, vol. 49 (9), p. 2116-2125 (2013).
Okines et al., "Effect of HER2 on prognosis and benefit from peri-operative chemotherapy in early oesophago-gastric adenocarcinoma in MAGIC trial," *Ann. Oncol.*, vol. 24 (5), p. 1253-1261 (2013).
Ott et al., "Chromosomal instability rather than p53 mutation is associated with response to neoadjuvant cisplatin-based chemotherapy in gastric carcinoma," *Clin. Cancer Res.*, vol. 9(6), p. 2307-2315(2003).
Ott et al., "Glutathione-transferase P1, T1 and M1 genetic polymorphisms in neoadjuvant-treated locally advanced gastric cancer: GSTM1-present genotype is associated with better prognosis in completely resected patients," *International Journal of Colorectal Disease*, vol. 23 (8), p. 773-782 (2008).
Ott et al., "The thymidylate synthase tandem repeat promoter polymorphism: A predictor for tumor-related survival in neoadjuvant treated locally advanced gastric cancer," *Int. J. Cancer*, vol. 119 (12), p. 2885-2894 (2006).
Palli et al., "Reproducibility of histologic classification of gastric cancer," *Br. J. Cancer*, vol. 63 (5), p. 765-768 (1991).
Peeters et al., "Validation of a nomogram for predicting disease-specific survival after an R0 resection for gastric carcinoma," *Cancer*, vol. 103 (4), p. 702-707 (2005).
Peng et al., "Prognostic significance of MET amplification and expression in gastric cancer: a systematic review with meta-analysis," *PLoS ONE*, vol. 9 (1), e84502 (2014).
Rice et al., "$7^{th}$ Edition of the AJCC Cancer Staging Manual: Esophagus and Esophagogastric Junction," *Annals of Surgical Oncology*, vol. 17 (7), p. 1721-1724 (2010).
Ruzzo et al., "Pharmacogenetic Profiling and Clinical Outcome of Patients With Advanced Gastric Cancer Treated With Palliative Chemotherapy," *Journal of Clinical Oncology*, vol. 24 (12), p. 1883-1891 (2006).
Sakurai et al., "Predictive value of orotate phosphoribosyltransferase in chemoresistant patients with gastric carcinoma who underwent S-1-based neoadjuvant/adjuvant chemotherapy," *Gan to Kagaku Ryoho*, vol. 35 (7), p. 1147-1155, Abstract only (2008).
Sakuramoto et al., "Adjuvant chemotherapy for gastric cancer with S-1, an oral fluoropyrimidine," *New England Journal of Medicine*, vol. 357 (18), p. 1810-1820 (2007).
Secrier et al., "Mutational signatures in esophageal adenocarcinoma define etiologically distinct subgroups with therapeutic relevance, "*Nat. Genet.*, vol. 48 (10), p. 1131-1145 (2016).
Seo et al., "Comprehensive analysis of excision repair complementation group 1, glutathione S-transferase, thymidylate synthase and uridine diphosphate glucuronosyl transferase 1A1 polymorphisms predictive for treatment outcome in patients with advanced gastric cancer treated with FOLFOX or FOLFIRI," *Oncol. Rep.*, vol. 22 (1), p. 127-136 (2009).
Shah et al., "Effect of Fluorouracil, Leucovorin, and Oxaliplatin With or Without Onartuzumab in HER2-Negative, MET-Positive Gastroesophageal Adenocarcinoma: The METGastric Randomized Clinical Trial," *JAMA Oncol.*, vol. 3 (5), p. 620-627 (2016).
Shah et al., "Molecular Classification of Gastric Cancer: A New Paradigm," *Clinical Cancer Research*, vol. 17 (9), p. 2693-2701 (2011).
Shibata et al., Histological classification of gastric adenocarcinoma for epidemiological research: concordance between pathologists, *Cancer Epidemiol Biomarkers Prev.*, vol. 10 (1), p. 75-78 (2001).
Shun et al., "An immunohistochemical study of E-cadherin expression with correlations to clinicopathological features in gastric cancer," *Hepato-gastroenterology*, vol. 45 (22), p. 944-949 (1998).
Smyth et al., "A randomized phase II study of perioperative epirubicin, cisplatin and capecitabine (ECX) + lapatinib for operable, HER-2 positive gastric, oesophagogastric junctional (OCJ) or lower oesophageal adenocarcinoma: Results from the UK MRC ST03 lapatinib feasibility study (ISRCTN 46020948)," *Annals of Oncology*, vol. 27 (suppl 6) (2016).
Smyth et al., "Gastric Cancer: ESMO Clinical Practice Guidelines for diagnosis, treatment and follow-up," *Ann. Oncol.*, vol. 27 (Suppl 5), p. v38-v49 (2016).
Songun et al., "Surgical treatment of gastric cancer: 15-year follow-up results of the randomized nationwide Dutch D1D2 trial," *Lancet Oncology*, vol. 11 (5), p. 439-449 (2010).
Su et al., "FGFR2 amplification has prognostic significance in gastric cancer: results from a large international multicentre study," *British Journal of Cancer*, vol. 110, p. 967-975 (2014).
Tan et al., "Intrinsic subtypes of gastric cancer, based on gene expression pattern, predict survival and respond differently to chemotherapy," *Gastroenterology*, vol. 141, p. 476-485, (2011).
Van Cutsem et al., "HER2 screening data from ToGA: targeting HFR2 in gastric and gastroesophageal junction cancer," *Gastric Cancer*, vol. 18 (3), p. 476-484 (2015).

(56) References Cited

OTHER PUBLICATIONS

Van Hagen et al., "Preoperative Chemoradiotherapy for Esophageal or Junctional Cancer," *New England Journal of Medicine*, vol. 366 (22), p. 2074-2084 (2012).

Waddell, et al., "Epirubicin, oxaliplatin, and capecitabine with or without panitumumab for patients with previously untreated advanced oesophagogastric cancer (REAL3): a randomized, open-label phase 3 trial," *Lancet Oncol.*, vol. 14 (6), p. 481-489 (2013).

Wang et al., "Polymorphisms in ERCC1, GSTs, TS and MTHFR predict clinical outcomes of gastric cancer patients treated with platinum/5-Fu-based chemotherapy: a systematic review," *BMC Gastroenterol*, 12:137 (2012).

Wilke et al., "Ramucirumab plus paclitaxel versus placebo plus paclitaxel in patients with previously treated advanced gastric or gastro-oesophageal junction adenocarcinoma (Rainbow): a double-blind, randomised phase 3 trial," *Lancet Oncol.*, vol. 15 (11), p. 1224-1235 (2014).

Yashiro et al., "Allelic imbalance at p53 and microsatellite instability are predictive markers for resistance to chemotherapy in gastric carcinoma," *Ann. Surg. Oncol.*, vol. 16 (10), p. 2926-2935 (2009).

Ychou et al., "Perioperative Chemotherapy Compared With Surgery Alone for Resectable Gastroesophageal Adenocarcinoma: An FNCLCC and FFCD Multicenter Phase III Trial," *Journal of Clinical Oncology*, vol. 29 (13), pp. 1715-1721 (2011).

Xu et al., "TXNL1-XRCC1 pathway regulates cisplatin-induced cell death and contributes to resistance in human gastric cancer," *Cell Death Dis.*, vol. 5, e1055 (2014).

\* cited by examiner

PROGNOSTIC AND TREATMENT RESPONSE PREDICTIVE METHOD

This application is the § 371 U.S. National Stage of International Application No. PCT/SG2018/050514, filed Oct. 12, 2018, which was published in English under PCT Article 21(2), which in turn claims priority from Application No. GB1716712.3, filed Oct. 12, 2017, which is incorporated herein by reference in its entirety.

FIELD OF THE INVENTION

The present invention relates to materials and methods for predicting response to chemotherapy and overall survival among cancer patients, particularly patients having resectable gastroesophageal cancer.

BACKGROUND TO THE INVENTION

Perioperative chemotherapy for patients with resectable gastroesophageal cancer has traditionally been offered on the basis of simplistic prognostic information such as AJCC/UICC stage [80]. The limitation of this approach is that stage of disease does not reliably predict chemosensitivity, nor benefit from chemotherapy.

The ability to classify tumours into molecular subgroups according to distinct biological features has been proposed as one method by which patients may be separated according to prognosis. It is hypothetically possible that subgroups with differential prognoses may derive distinct benefits from chemotherapy. However, methods that specifically model molecular profiles together with prognostic and predictive information will provide better predictive value.

Historically, the most well-known classification system for gastric cancer is the Lauren subtype system which divides gastric cancers into intestinal and diffuse subtypes based on cell morphology using H&E slides.[30] This system has been prognostic in several series, although this is variable, and Lauren classification was not prognostic in multivariate analysis of the MAGIC dataset [10, 27, 32, 36]. However, as Lauren subtype is assigned based on pathological review, an element of subjectivity is inevitable, which may explain this variance between datasets. Although other histological and molecular subtypes have been described, independently validation is lacking [300, 301].

In 2011, Tan et al described two intrinsic gastric cancer subtypes (G-INT and G-DIFF) which were derived from a panel of 37 gastric cancer cell lines using the Affymetrix Human Genome U133 plus GeneChips platform [302]. These were derived using a class discovery approach using unsupervised hierarchical clustering. Following this, the findings were confirmed using alternative methods such as silhouette plot, nonnegative matrix factorization, and principal components analysis.

Silhouette value is a measure of the similarity of an object to the allocated cluster (cohesion) compared to alternative clusters (separation) [303]. Non-negative matrix factorization reduces datasets containing large numbers of genes to a smaller number of metagenes, the association between the expression of the metagenes is then analysed [304, 305]. Principal component analysis (PCA) is a mathematical process that aims to decrease the dimensionality by transforming it to a new set of variables (the principle components) which summarize the data whilst retaining variation [306, 307].

Differences in the expression of 171 genes using a stringent false discovery rate were associated with two subtypes with limited correlation between genes (2/171 with r>0.88). Two class prediction algorithms were used to map the G-INT and G-DIF subtypes to two independent datasets (one from Singapore, the other Australian) with high concordance (94-96%). Both subtypes were statistically significantly associated with Lauren subtype (intestinal and diffuse) in both cohorts, hence the nomenclature chosen. However, the concordance if the intrinsic subtypes with Lauren subtype was imperfect (64%). Although Lauren classification was not prognostic in either cohort, intrinsic subtypes were statistically significantly associated with survival in the Singapore and combined cohorts, but not the Australian cohort (HR for G-DIF vs. G-INT in combined cohort 1.79; 95% CI, 1.28-2.51; P=0.001). Further validation of the prognostic value of the signatures was carried out using a separate microarray platform (Illumina Human-6 v2 Expression BeadChips) on a third dataset. Although relatively few patients in the cohort were treated with adjuvant 5-fluorouracil based chemotherapy, an interaction between intrinsic subtype and benefit from adjuvant chemotherapy was suggested with G-INT subtype patients appeared to derive more benefit from this approach than patients with the G-DIF subtype (p. value for interaction 0.002).

WO 2014/046619 describes a grouping for classifying a gastric cancer tumour sample obtained from a patient suffering or suspected to suffer from gastric cancer. A predictive gene signature is used to classify to an invasive subtype, a proliferative subtype or a metabolic subtype.

While previously described predictive models of gastric cancer show promise, there remains an unmet need for further models able to predict treatment response and/or survival of gastric cancer patients. The present invention seeks to fulfil these needs and provides further related advantages.

BRIEF DESCRIPTION OF THE INVENTION

The present inventors initially sought to validate the prognostic and predictive effects of the G-INT and G-DIF subtypes in the MAGIC dataset. However, no statistically significant differences in overall survival were seen between intrinsic subtypes in either arm of the trial, or in the population overall. The inventors therefore carried out an analysis to a) identify individual genes the expression of which is associated with overall survival in chemotherapy treated patients and b) group these genes as a signature in order to identify high and low risk groups of patients based on gene expression only in post-chemotherapy resection specimens. A signature comprising seven genes was found to be predict overall survival of the chemotherapy-treated patients. Accordingly, in a first aspect the present invention provides a method for predicting the treatment response of a human gastroesophageal cancer patient, the method comprising:

a) measuring the gene expression of at least 3, 4, 5, 6, 7 or more (such as all of) the following genes: CDH1, CDK6, COX2, ELOVL5, GATA4, EGFR, TBCEL, FGF7, CDH17, FNBP1, PIP5K1B, TWIST, CD44, MET, CEACAM1, TOX3, GLIPR2, GSTP1, RON, TMEM136, MYB, BRCA2, FGF1, POU5F1, EPR, DPYD, ABL2 and SH3RF1 in a sample obtained from the gastroesophageal tumour of the patient to obtain a sample gene expression profile of at least said genes; and b) making a prediction of the treatment response and/or prognosis of the patient based on the sample gene expression profile.

In a related aspect, the present invention provides a method for predicting the treatment response of a human gastroesophageal cancer patient, the method comprising:
  a) measuring the gene expression of at least 3, 4, 5, 6, 7 or more (such as all of) the following genes: CDH1, CDK6, COX2, ELOVL5, GATA4, EGFR, TBCEL, FGF7, CDH17, FNBP1, PIP5K1B, TWIST, CD44, MET, CEACAM1, TOX3, GLIPR2, GSTP1, RON, TMEM136, MYB, BRCA2, FGF1, POU5F1, EPR, DPYD and SH3RF1 in a sample obtained from the gastroesophageal tumour of the patient to obtain a sample gene expression profile of at least said genes; and
  b) making a prediction of the treatment response and/or prognosis of the patient based on the sample gene expression profile.

In some embodiments, the at least 3 genes comprise at least the genes CDH1, ELOVL5, EGFR, PIP5K1B, FGF1, CD44 and TBCEL.

In some embodiments step b) making a prediction of the treatment response of the patient based on the sample gene expression profile comprises:
  (i) optionally, normalising the measured expression level of each gene relative to the expression level of one or more housekeeping genes;
  (ii) computing a risk score by weighting the measured, and optionally normalised, expression level of each gene and summing the weighted expression level of each of the genes, wherein the contribution to the total risk score made by CD44 and EGFR has the opposite sign to that of the contribution made by CDH1, ELOVL5, PIP5K1B, FGF1 and TBCEL.

In some embodiments, the risk score is referenced to the median risk score of a sample cohort of gastric cancer patients, which median risk score serves as a threshold, and wherein:
  a computed risk score of above that threshold indicates that the patient is at high risk of poor treatment response, at high risk of suffering recurrence of the tumour and/or at high risk of having a shorter than median survival time; and
  a computed risk score of below that threshold indicates that the patient is at low risk of poor treatment response, at low risk of suffering recurrence of the tumour and/or at low risk of having a shorter than median survival time.

In some embodiments, the risk score for the patient is calculated by taking, for each gene, the product of the hazard ratio (HR) for that gene and the measured, and optionally normalised, gene expression value, summing those products for all seven genes, wherein the sign of the genes CDH1, ELOVL5, PIP5K1B, FGF1 and TBCEL is negative, lowering the total risk score with increasing expression, and the sign of the genes CD44 and EGFR is positive, increasing the total risk score with increasing expression.

In some embodiments, the HR for each of the genes is as follows:

| Genes | HR |
| --- | --- |
| CDH1_201131_s_at | 0.5279 ± 0.01 |
| ELOVL5 | 0.6523 ± 0.01 |
| EGFR | 1.5308 ± 0.01 |
| PIP5K1B | 0.537 ± 0.01 |
| FGF1 | 0.6604 ± 0.01 |

-continued

| Genes | HR |
| --- | --- |
| CD44v8.10 | 1.3418 ± 0.01 |
| TBCEL | 0.6569 ± 0.01 |

In some embodiments, step b) making a prediction of the treatment response of the patient based on the sample gene expression profile comprises:
  (i) optionally, normalising the measured expression level of each gene relative to the expression level of one or more housekeeping genes;
  (ii) comparing the sample gene expression profile, optionally after said normalising, with two or more reference centroids comprising:
    a first reference centroid that represents the average gene expression of at least the genes CDH1, ELOVL5, EGFR, PIP5K1B, FGF1, CD44 and TBCEL measured in a low risk training set made up of gastroesophageal cancer patients known to have had a median survival time following tumour resection of greater than 3 years or greater than 6 years; and
    a second reference centroid that represents the average gene expression of at least the genes CDH1, ELOVL5, EGFR, PIP5K1B, FGF1, CD44 and TBCEL measured in a high risk training set made up of gastroesophageal cancer patients known to have had a median survival time following tumour resection of less than 1.5 years or less than 1 year;
  c) classifying the sample gene expression profile as belonging to the risk group having the reference centroid to which it is most closely matched; and
  d) providing a prediction of treatment response or prognosis based on the classification made in step c).

In some embodiments, said first reference centroid comprises the following low-risk centroid and said second reference centroid comprises the following high-risk centroid:

| Genes | Low-Risk | High-Risk |
| --- | --- | --- |
| ELOVL5 | 0.1357 | −0.1357 |
| TBCEL | 0.135 | −0.135 |
| CDH1_201131_s_at | 0.1293 | −0.1293 |
| CD44v8.10 | −0.1045 | 0.1045 |
| PIP5K1B | 0.0928 | −0.0928 |
| EGFR | −0.0689 | 0.0689 |
| FGF1 | 0.0422 | −0.0422. |

In some embodiments, step b) making a prediction of the treatment response of the patient based on the sample gene expression profile comprises:
  (i) optionally, normalising the measured expression level of each gene relative to the expression level of one or more housekeeping genes;
  (ii) comparing the sample gene expression profile, optionally after said normalising, with at least three reference centroids corresponding to low, moderate and high risk subgroups, respectively, the reference centroid comprising:
    a first reference centroid that represents the average gene expression of at least the genes CDH1, ELOVL5, EGFR, PIP5K1B, FGF1, CD44 and TBCEL measured in a low risk training set made up of gastroesophageal cancer patients known to have had median survival time following tumour resection of greater than 7 years;

a second reference centroid that represents the average gene expression of at least the genes CDH1, ELOVL5, EGFR, PIP5K1B, FGF1, CD44 and TBCEL measured in a moderate risk training set made up of gastroesophageal cancer patients known to have had median survival time following tumour resection of between 1.4 and 4.5 years; and a third reference centroid that represents the average gene expression of at least the genes CDH1, ELOVL5, EGFR, PIP5K1B, FGF1, CD44 and TBCEL measured in a high risk training set made up of gastroesophageal cancer patients known to have had median survival time following tumour resection of less than 0.6 years or even less than 0.4 years;

c) classifying the sample gene expression profile as belonging to the risk group having the reference centroid to which it is most closely matched; and d) providing a prediction of treatment response or prognosis based on the classification made in step c).

In some embodiments, said first reference centroid comprises the following low-risk centroid, said second reference centroid comprises the following moderate-risk centroid, and said third reference centroid comprises the following high-risk centroid:

| Genes | Low | Moderate | High |
| --- | --- | --- | --- |
| TBCEL | 0.2627 | 0.0681 | −0.3688 |
| EGFR | −0.1283 | −0.1239 | 0.3531 |
| ELOVL5 | 0.2344 | 0.0563 | −0.3206 |
| CDH1_201131_s_at | 0.3142 | −0.0041 | −0.2778 |
| CD44v8.10 | −0.295 | 0.0997 | 0.0779 |
| FGF1 | 0.2825 | −0.0103 | −0.2371 |
| PIP5K1B | 0.2442 | 0.0037 | −0.2292. |

In some embodiments, the gene expression profile is of an expanded gene set comprising said seven genes CDH1, ELOVL5, EGFR, PIP5K1B, FGF1, CD44 and TBCEL and further comprising at least 1, 2, 3, 4, 5, 6, 7, 8, 9, 10, 11, 12, 13, 14, 15, 16, 17, 18, 19 or at least 20 genes selected from the group consisting of: FGF7, CDK6, GLIPR2, FNBP1, TOX3, ABL2, RON, CDH17, GATA4, TWIST, COX2, BRCA2, DPYD, CEACAM1, EPR, MET, TMEM136, MYB, SH3RF1, POU5F1 and GSTP1.

In some embodiments, the gene expression profile is of an expanded gene set comprising at least the genes CDH1, ELOVL5, EGFR, PIP5K1B, FGF1, CD44, TBCEL, FGF7, CDK6, GLIPR2, FNBP1, TOX3, ABL2, RON, CDH17, GATA4, TWIST, COX2, BRCA2, DPYD, CEACAM1, EPR, MET, TMEM136, MYB, SH3RF1, POU5F1 and GSTP1.

In some embodiments, step b) making a prediction of the treatment response of the patient based on the sample gene expression profile comprises:

(i) optionally, normalising the measured expression level of each gene relative to the expression level of one or more housekeeping genes;

(ii) comparing the sample gene expression profile, optionally after said normalising, with at least two reference centroids corresponding to low and high risk subgroups, respectively, the reference centroids comprising:

| Genes | Low-Risk | High-Risk |
| --- | --- | --- |
| ELOVL5 | 0.1967 | −0.1967 |
| TBCEL | 0.1961 | −0.1961 |

-continued

| Genes | Low-Risk | High-Risk |
| --- | --- | --- |
| CDH1_201131_s_at | 0.1903 | −0.1903 |
| FGF7 | 0.1737 | −0.1737 |
| CD44v8.10 | −0.1656 | 0.1656 |
| PIP5K1B | 0.1538 | −0.1538 |
| CDK6 | 0.1513 | −0.1513 |
| GLIPR2 | 0.1379 | −0.1379 |
| FNBP1 | 0.1308 | −0.1308 |
| EGFR | −0.1299 | 0.1299 |
| TOX3 | 0.1212 | −0.1212 |
| ABL2 | 0.1179 | −0.1179 |
| CDH1_201130_s_at | 0.1044 | −0.1044 |
| FGF1 | 0.1033 | −0.1033 |
| RON | −0.1003 | 0.1003 |
| CDH17 | 0.0996 | −0.0996 |
| GATA4 | −0.0929 | 0.0929 |
| TWIST | 0.0848 | −0.0848 |
| COX2 | 0.0739 | −0.0739 |
| BRCA2 | 0.0664 | −0.0664 |
| DPYD | 0.0635 | −0.0635 |
| CEACAM1 | 0.0607 | −0.0607 |
| EPR | 0.0568 | −0.0568 |
| MET | −0.0452 | 0.0452 |
| TMEM136 | 0.043 | −0.043 |
| MYB | 0.0206 | −0.0206 |
| SH3RF1 | 0.0129 | −0.0129 |
| POU5F1 | 0.0127 | −0.0127 |
| GSTP1 | 0.0043 | −0.0043. |

In some embodiments, step b) making a prediction of the treatment response of the patient based on the sample gene expression profile comprises:

(i) optionally, normalising the measured expression level of each gene relative to the expression level of one or more housekeeping genes;

(ii) comparing the sample gene expression profile, optionally after said normalising, with at least three reference centroids corresponding to low, moderate and high risk subgroups, respectively, the reference centroids comprising:

| Genes | Low | Moderate | High |
| --- | --- | --- | --- |
| TBCEL | 0.2631 | 0.0682 | −0.3694 |
| EGFR | −0.1285 | −0.1241 | 0.3536 |
| FGF7 | 0.1373 | 0.119 | −0.3519 |
| CDH17 | 0.0807 | 0.1335 | −0.3282 |
| ELOVL5 | 0.2348 | 0.0564 | −0.3212 |
| CDH1_201131_s_at | 0.3146 | −0.0041 | −0.2782 |
| TWIST | 0.0257 | 0.1469 | −0.3039 |
| CD44v8.10 | −0.2954 | 0.0998 | 0.078 |
| ABL2 | 0.2853 | −0.0256 | −0.2104 |
| FGF1 | 0.283 | −0.0104 | −0.2375 |
| CDH1_201130_s_at | 0.2752 | −0.034 | −0.1852 |
| FNBP1 | 0.1321 | 0.0756 | −0.2645 |
| CDK6 | 0.2446 | −0.0149 | −0.194 |
| PIP5K1B | 0.2446 | 0.0037 | −0.2295 |
| TOX3 | 0.1031 | 0.0698 | −0.227 |
| GLIPR2 | 0.1334 | 0.0462 | −0.2095 |
| GATA4 | 0.0048 | −0.1038 | 0.1937 |
| COX2 | 0.1143 | 0.0466 | −0.1928 |
| BRCA2 | 0.0496 | 0.0749 | −0.188 |
| MET | −0.1698 | 0.0384 | 0.0811 |
| POU5F1 | 0.1662 | −0.0272 | −0.0991 |
| TMEM136 | 0.1508 | −0.0421 | −0.0566 |
| MYB | 0.0064 | 0.0635 | −0.1271 |
| CEACAM1 | 0.0886 | 0.0147 | −0.1086 |
| GSTP1 | 0.0172 | 0.0436 | −0.0989 |
| RON | −0.0625 | −0.0208 | 0.0965 |
| DPYD | 0.0506 | −0.0154 | −0.0166 |
| EPR | −0.0284 | 0.0345 | −0.04 |
| SH3RF1 | 0.0297 | −0.0336 | 0.037. |

In some embodiments, the expression level of at least the genes CDH1, COX2, ELOVL5, GATA4 and EGFR are measured to obtain a gene expression profile of at least those five genes. In some particularly preferred embodiments, the expression level of at least the genes CDH1, CDK6, COX2, ELOVL5, GATA4, EGFR and TBCEL are measured to obtain a gene expression profile of at least those seven genes.

In some cases the CDH1 gene expression is of the CDH1 gene as associated with probe 201130_s_at of Affymetrix GeneChip Human Genome U133 Plus 2.0 Array. Alternatively or additionally, in some cases, the CDH1 gene expression is of the CDH1 gene as associated with probe 201131_s_at of Affymetrix GeneChip Human Genome U133 Plus 2.0 Array. In some embodiments, the CD44 gene expression is of the CD44v8-10 isoform.

In some embodiments, the patient is a patient who has had perioperative (particularly pre-operative) chemotherapy and surgical resection of the gastroesophageal tumour. Perioperative chemotherapy may include 1-3 cycles of chemotherapy pre-operatively and/or 1-3 cycles of chemotherapy post-operatively. In some specific embodiments, perioperative chemotherapy may be as described for the chemotherapy+surgery arm of the MAGIC trial (Cunningham et. al., *N. Engl. J. Med.* 2006; Vol. 355, pp. 11-20). In particular embodiments, the sample may be a sample taken from the tumour after all or part of the tumour has been removed, i.e. a resected tumour sample.

In some embodiments, the patient has had at least one treatment with one or more chemotherapeutic agents selected from the group consisting of: epirubicin, cisplatin, 5-fluourouracil, capecitabine, oxaliplatin, and docetaxel. In particular cases, the patient has had perioperative treatment with epirubicin, cisplatin and 5-fluourouracil (either infused or oral capecitabine). In certain cases, the patient has had perioperative treatment with docetaxel, oxaliplatin and 5-fluourouracil.

In some embodiments, making a prediction of the treatment response of the patient based on the sample gene expression profile comprises:
(i) optionally, normalising the measured expression level of each gene relative to the expression level of one or more housekeeping genes (e.g. one or more of: ACTB, GAPDH and TBP);
(ii) computing a risk score by weighting the measured (and optionally normalised) expression level of each gene (e.g. multiplying the measured expression level by a coefficient) and summing the weighted expression level of each of the genes, wherein the contribution to the total risk score made by GATA4 and EGFR has the opposite sign to that of the contribution made by CDH1, CDK6, COX2, ELOVL5 and TBCEL.

In certain cases, the risk score is related to a reference or threshold level, for example wherein the median risk of a cohort of patients is set to an arbitrary threshold (e.g. zero) or is median centred and wherein:
a computed risk score of above that threshold (e.g. a positive value) indicates that the patient is at high risk of poor treatment response, at high risk of suffering recurrence of the tumour and/or at high risk of having a shorter survival time than is typical of surgically-treated gastroesophageal cancer patients; and
a computed risk score of below that threshold (e.g. a negative value) indicates that the patient is at low risk of poor treatment response, at low risk of suffering recurrence of the tumour and/or at low risk of having a shorter survival time than is typical of surgically-treated gastroesophageal cancer patients.

In certain cases, the risk score is computed using the hazard ratio (HR) for each gene as determined by the Cox regression analysis described herein. In particular, the risk score for the patient may be calculated by taking, for each gene, the product of HR for that gene and the measured (and optionally normalised) gene expression value and summing those products for all seven genes, wherein the sign of the genes CDH1, CDK6, COX2, ELOVL5 and TBCEL is negative (lowering the total risk score with increasing expression) and the sign of the genes GATA4 and EGFR is positive (increasing the total risk score with increasing expression). In some cases the HR for each of the genes is as follows:

| Gene | HR |
| --- | --- |
| CDH1 | 0.47893519 ± 0.01 |
| CDK6 | 0.86568645 ± 0.01 |
| COX2 | 0.60951164 ± 0.01 |
| ELOVL5 | 0.66837402 ± 0.01 |
| GATA4 | 1.23187407 ± 0.01 |
| EGFR | 1.36866119 ± 0.01 |
| TBCEL | 0.68325777 ± 0.01. |

In some embodiments, step (b) making a prediction of the treatment response of the patient based on the sample gene expression profile comprises:
(i) optionally, normalising the measured expression level of each gene relative to the expression level of one or more housekeeping genes (e.g. one or more of: ACTB, GAPDH and TBP;
(ii) comparing the sample gene expression profile with two or more reference centroids comprising:
a first reference centroid that represents the average gene expression of at least the genes CDH1, CDK6, COX2, ELOVL5, GATA4, EGFR and TBCEL measured in a low risk training set made up of gastroesophageal cancer patients found to have had greater survival time following tumour resection than is typical for gastroesophageal cancer patients in the general population (e.g. greater than 3.51 years or even greater than 6.65 years); and
a second reference centroid that represents the average gene expression of at least the genes CDH1, CDK6, COX2, ELOVL5, GATA4, EGFR and TBCEL measured in a high risk training set made up of gastroesophageal cancer patients found to have had shorter survival time following tumour resection than is typical for gastroesophageal cancer patients in the general population (e.g. less than 1.36 years or even less than 0.95 years);
c) classifying the sample gene expression profile as belonging to the risk group having the reference centroid to which it is most closely matched; and
d) providing a prediction of treatment response based on the classification made in step c).

In some cases the two or more reference centroids may comprise three reference centroids corresponding to low, moderate and high risk subgroups, respectively, the reference centroid comprising:
a first reference centroid that represents the average gene expression of at least the genes CDH1, CDK6, COX2, ELOVL5, GATA4, EGFR and TBCEL measured in a low risk training set made up of gastroesophageal cancer patients found to have had greater average survival time following tumour resection than is typical for gastroesophageal cancer patients in the general population (e.g. greater than 7 years);

a second reference centroid that represents the average gene expression of at least the genes CDH1, CDK6, COX2, ELOVL5, GATA4, EGFR and TBCEL measured in a moderate risk training set made up of gastroesophageal cancer patients found to have had medium average survival time following tumour resection that is typical for gastroesophageal cancer patients in the general population (e.g. between 1.41 and 4.46 years or around 2.07 years); and a third reference centroid that represents the average gene expression of at least the genes CDH1, CDK6, COX2, ELOVL5, GATA4, EGFR and TBCEL measured in a high risk training set made up of gastroesophageal cancer patients found to have had shorter average survival time following tumour resection than is typical for gastroesophageal cancer patients in the general population (e.g. less than 0.54 years or even less than 0.42 years).

In certain cases, the reference centroids may have been pre-determined and may be obtained by, e.g., retrieval from a volatile or non-volatile computer memory or data store (including retrieval from a network or other remote store). The derivation of exemplary centroids is described in detail herein. In certain embodiments, the reference centroids may comprise one, two or all three centroids selected from the group consisting of:

| | Centroids | | |
|---|---|---|---|
| genes | 1. High Risk | 2. Low Risk | 3. Moderate Risk |
| TBCEL | −0.9271 | 0.2638 | 0.0217 |
| ELOVL5 | −0.7801 | 0.2959 | −0.0172 |
| COX2 | −0.6045 | 0.0574 | 0.0692 |
| CDH1 | −0.1409 | 0.2648 | −0.1046 |
| CDK6 | 0.0886 | 0.2509 | −0.1346 |
| EGFR | 0.0974 | −0.0777 | 0.0217 |
| GATA4 | 0.0698 | 0.067 | −0.0433. |

In some cases the CDH1 gene expression is of the CDH1 gene as associated with probe 201130_s_at of Affymetrix GeneChip Human Genome U133 Plus 2.0 Array.

In some cases the sample gene expression profile may be compared with each reference centroid for closeness of fit using K-means clustering, model based clustering, non-negative matrix factorization, variants of factor analysis or principal component analysis.

In accordance with any aspect of the present invention, the gene expression signature may be of an expanded gene set comprising said seven genes CDH1, CDK6, COX2, ELOVL5, GATA4, EGFR and TBCEL and further comprising at least one gene (e.g. 2, 3, 4, 5, 6, 7, 8, 9, 10, 11, 12, 13, 14, 15, 16, 17, 18, 19 or 20 genes) selected from the group consisting of: FGF7, CDH17, FNBP1, PIP5K1B, TWIST, CD44 MET, CEACAM1, TOX3, GLIPR2, GSTP1, RON, TMEM136, MYB, CDH1 (associated with probe 201130_s_at of Affymetrix GeneChip Human Genome U133 Plus 2.0 Array), BRCA2, FGF1, POU5F1, EPR, DPYD and SH3RF1.

In some cases the gene expression signature may be of an expanded gene set comprising at least the genes CDH1, CDK6, COX2, ELOVL5, GATA4, EGFR, TBCEL, FGF7, CDH17, FNBP1, PIP5K1B, TWIST, CD44 (e.g. isoform v8-10), MET, CEACAM1, TOX3, GLIPR2, GSTP1, RON, TMEM136, MYB, BRCA2, FGF1, POU5F1, EPR, DPYD and SH3RF1.

In particular embodiments, for example where an expanded gene set is employed, the reference centroids may comprise one, two or all three centroids selected from the group consisting of:

| | Centroids | | |
|---|---|---|---|
| Genes | 1. High Risk | 2. Low Risk | 3. Moderate Risk |
| FGF7 | −1.5785 | 0.0235 | 0.2413 |
| CDH17 | −1.2605 | −0.162 | 0.2794 |
| FNBP1 | −1.0724 | 0.1664 | 0.0917 |
| TBCEL | −0.9271 | 0.2638 | 0.0217 |
| PIP5K1B | −0.8545 | 0.1563 | 0.0617 |
| ELOVL5 | −0.7801 | 0.2959 | −0.0172 |
| TWIST | −0.7556 | −0.021 | 0.131 |
| CD44v8.10 | 0.0687 | −0.6475 | 0.2998 |
| MET | 0.628 | −0.4301 | 0.106 |
| COX2 | −0.6045 | 0.0574 | 0.0692 |
| CEACAM1 | −0.5618 | 0.1421 | 0.0217 |
| TOX3 | −0.5553 | 0.0584 | 0.0608 |
| GLIPR2 | −0.5525 | 0.1912 | −0.0034 |
| GSTP1 | −0.4809 | 0.0578 | 0.0492 |
| RON | 0.4109 | −0.309 | 0.0826 |
| TMEM136 | −0.3886 | 0.2811 | −0.0727 |
| MYB | −0.3709 | −0.0939 | 0.1044 |
| CDH1_201130_s_at | −0.128 | 0.3616 | −0.1531 |
| BRCA2 | −0.3143 | −0.0752 | 0.0864 |
| CDH1_201131_s_at | −0.1409 | 0.2648 | −0.1046 |
| FGF1 | −0.2643 | 0.1278 | −0.019 |
| CDK6 | 0.0886 | 0.2509 | −0.1346 |
| POU5F1 | −0.2326 | 0.2432 | −0.0795 |
| EPR | 0.028 | −0.2399 | 0.1107 |
| DPYD | 0.1492 | 0.0302 | −0.0384 |
| SH3RF1 | 0.1005 | 1.00E−04 | −0.0161 |
| EGFR | 0.0974 | −0.0777 | 0.0217 |
| GATA4 | 0.0698 | 0.067 | −0.0433. |

In accordance with any aspect of the present invention, the method may further comprise obtaining information as to the nodal status of the patient. A patient found to be positive for tumour cells at one or more lymph nodes may be classified as having greater risk of poor outcome (e.g. failure to respond to treatment and/or earlier death) independent of the risk classification made using the gene expression profile.

In accordance with any aspect of the present invention, the method may further comprise selecting the patient for an appropriate treatment in view of the risk classification made by the method of the present invention. In particular, when the patient is found to be at high or moderate risk of poor treatment response by the method of the present invention, the patient may be selected for additional or alternative treatment, including aggressive treatment. In certain cases, an aggressive treatment selection for a patient determined to be at high risk of poor treatment response may comprise the same chemotherapeutic agent or combination of agents that were administered to the patient perioperatively, but administered more frequently and/or at a higher dose. In some cases, an aggressive treatment selection for a patient determined to be at high or moderate risk of poor treatment response may comprise a different chemotherapeutic agent or combination of agents than were administered to the patient perioperatively. For example, the patient may be selected for an experimental drug treatment, antibody therapy (e.g. trastuzumab for HER2 positive gastric carcinoma), immunotherapy and/or radiotherapy. When the patient is found to be at low risk of poor treatment response by the method of the present invention, the patient may be selected less aggressive ongoing treatment or even for non-treatment. As described in detail herein, a number of the patients from the MAGIC trial (chemotherapy+surgery arm)

that were classified as low risk based on gene expression signature in accordance with the method of the present invention survived beyond the study period. Such low risk patients may benefit from avoidance of unnecessary follow-on treatment, e.g., by avoiding unwanted side effects associated with chemotherapy.

In a second aspect, the present invention provides a computer-implemented method for predicting the treatment response or prognosis of a human gastroesophageal cancer patient, the method comprising:
a) obtaining gene expression data comprising a gene expression profile representing gene expression measurements of at least the genes CDH1, ELOVL5, EGFR, PIP5K1B, FGF1, CD44 and TBCEL measured in a sample obtained from the gastroesophageal tumour of the patient; and
b) (i) optionally, normalising the measured expression level of each gene relative to the expression level of one or more housekeeping genes,
  (ii) comparing the sample gene expression profile with two or more reference centroids as defined in Table 16 or Table 18;
c) classifying the sample gene expression profile as belonging to the risk group having the reference centroid to which it is most closely matched; and
d) providing a prediction of treatment response or prognosis based on the classification made in step c).

In a related aspect, the present invention provides a computer-implemented method for predicting the treatment response or prognosis of a human gastroesophageal cancer patient, the method comprising:
a) obtaining gene expression data comprising a gene expression profile representing gene expression measurements of at least the genes CDH1, ELOVL5, EGFR, PIP5K1B, FGF1, CD44, TBCEL, FGF7, CDK6, GLIPR2, FNBP1, TOX3, ABL2, RON, CDH17, GATA4, TWIST, COX2, BRCA2, DPYD, CEACAM1, EPR, MET, TMEM136, MYB, SH3RF1, POU5F1 and GSTP1 measured in a sample obtained from the gastroesophageal tumour of the patient; and
b) (i) optionally, normalising the measured expression level of each gene relative to the expression level of one or more housekeeping genes,
  (ii) comparing the sample gene expression profile with two or more reference centroids as defined in Table 17 or Table 19;
c) classifying the sample gene expression profile as belonging to the risk group having the reference centroid to which it is most closely matched; and
d) providing a prediction of treatment response or prognosis based on the classification made in step c).

In a related aspect, the present invention provides a computer-implemented method for predicting the treatment response of a human gastroesophageal cancer patient, the method comprising:
a) obtaining gene expression data comprising a gene expression profile representing gene expression measurements as defined in connection with the first aspect of the invention, such as the measurements of at least the genes CDH1, CDK6, COX2, ELOVL5, GATA4, EGFR and TBCEL measured in a sample obtained from the gastroesophageal tumour of the patient; and
b) (i) optionally, normalising the measured expression level of each gene relative to the expression level of one or more housekeeping genes,
  (ii) comparing the sample gene expression profile with two or more reference centroids comprising:
    a first reference centroid that represents the average gene expression of at least the genes CDH1, CDK6, COX2, ELOVL5, GATA4, EGFR and TBCEL measured in a low risk training set made up of gastroesophageal cancer patients found to have had greater survival time following tumour resection than is typical for gastroesophageal cancer patients in the general population (e.g. greater than 3.51 years or even greater than 6.65 years); and
    a second reference centroid that represents the average gene expression of at least the genes CDH1, CDK6, COX2, ELOVL5, GATA4, EGFR and TBCEL measured in a high risk training set made up of gastroesophageal cancer patients found to have had shorter survival time following tumour resection than is typical for gastroesophageal cancer patients in the general population (e.g. less than 1.36 years or even less than 0.95 years);
c) classifying the sample gene expression profile as belonging to the risk group having the reference centroid to which it is most closely matched; and
d) providing a prediction of treatment response based on the classification made in step c).

In some cases the two or more reference centroids may comprise three reference centroids corresponding to low, moderate and high risk subgroups, respectively, the reference centroid comprising:

| genes | Centroids | | |
|---|---|---|---|
| | 1. High Risk | 2. Low Risk | 3. Moderate Risk |
| TBCEL | −0.9271 | 0.2638 | 0.0217 |
| ELOVL5 | −0.7801 | 0.2959 | −0.0172 |
| COX2 | −0.6045 | 0.0574 | 0.0692 |
| CDH1 | −0.1409 | 0.2648 | −0.1046 |
| CDK6 | 0.0886 | 0.2509 | −0.1346 |
| EGFR | 0.0974 | −0.0777 | 0.0217 |
| GATA4 | 0.0698 | 0.067 | −0.0433. |

In some cases the sample gene expression profile may be compared with each reference centroid for closeness of fit using K-means clustering.

As with the first aspect of the present invention, the gene expression signature may be of an expanded gene set comprising said seven genes CDH1, CDK6, COX2, ELOVL5, GATA4, EGFR and TBCEL and further comprising at least one gene (e.g. 2, 3, 4, 5, 6, 7, 8, 9, 10, 11, 12, 13, 14, 15, 16, 17, 18, 19 or 20 genes) selected from the group consisting of: FGF7, CDH17, FNBP1, PIP5K1B, TWIST, CD44 (e.g. isoform v8.10), MET, CEACAM1, TOX3, GLIPR2, GSTP1, RON, TMEM136, MYB, BRCA2, FGF1, POU5F1, EPR, DPYD and SH3RF1. In some cases the gene expression signature may be of an expanded gene set comprising at least the genes CDH1, CDK6, COX2, ELOVL5, GATA4, EGFR, TBCEL, FGF7, CDH17, FNBP1, PIP5K1B, TWIST, CD44v8.10, MET, CEACAM1, TOX3, GLIPR2, GSTP1, RON, TMEM136, MYB, BRCA2, FGF1, POU5F1, EPR, DPYD and SH3RF1. In some cases, the CDH1 gene expression is of the CDH1 gene as associated with probe 201130_s_at of Affymetrix GeneChip Human Genome U133 Plus 2.0 Array. Alternatively or additionally, in some cases, the CDH1 gene expression is of the CDH1 gene as associated with probe 201131_s_at of Affymetrix GeneChip Human Genome U133 Plus 2.0 Array.

In particular embodiments, the reference centroids may comprise:

| Genes | Centroids | | |
|---|---|---|---|
| | 1. High Risk | 2. Low Risk | 3. Moderate Risk |
| FGF7 | −1.5785 | 0.0235 | 0.2413 |
| CDH17 | −1.2605 | −0.162 | 0.2794 |
| FNBP1 | −1.0724 | 0.1664 | 0.0917 |
| TBCEL | −0.9271 | 0.2638 | 0.0217 |
| PIP5K1B | −0.8545 | 0.1563 | 0.0617 |
| ELOVL5 | −0.7801 | 0.2959 | −0.0172 |
| TWIST | −0.7556 | −0.021 | 0.131 |
| CD44v8.10 | 0.0687 | −0.6475 | 0.2998 |
| MET | 0.628 | −0.4301 | 0.106 |
| COX2 | −0.6045 | 0.0574 | 0.0692 |
| CEACAM1 | −0.5618 | 0.1421 | 0.0217 |
| TOX3 | −0.5553 | 0.0584 | 0.0608 |
| GLIPR2 | −0.5525 | 0.1912 | −0.0034 |
| GSTP1 | −0.4809 | 0.0578 | 0.0492 |
| RON | 0.4109 | −0.309 | 0.0826 |
| TMEM136 | −0.3886 | 0.2811 | −0.0727 |
| MYB | −0.3709 | −0.0939 | 0.1044 |
| CDH1_201130_s_at | −0.128 | 0.3616 | −0.1531 |
| BRCA2 | −0.3143 | −0.0752 | 0.0864 |
| CDH1_201131_s_at | −0.1409 | 0.2648 | −0.1046 |
| FGF1 | −0.2643 | 0.1278 | −0.019 |
| CDK6 | 0.0886 | 0.2509 | −0.1346 |
| POU5F1 | −0.2326 | 0.2432 | −0.0795 |
| EPR | 0.028 | −0.2399 | 0.1107 |
| DPYD | 0.1492 | 0.0302 | −0.0384 |
| SH3RF1 | 0.1005 | 1.00E−04 | −0.0161 |
| EGFR | 0.0974 | −0.0777 | 0.0217 |
| GATA4 | 0.0698 | 0.067 | −0.0433 |

In a third aspect, the present invention provides a method of treatment of gastroesophageal cancer in a human patient, said patient having had at least one perioperative treatment with one or more chemotherapeutic agents and having had surgical resection of a gastroesophageal tumour, the method comprising:
 (a) carrying out the method of the first or second aspects of the present invention; and
 (b) (i) when the patient is determined to be at high or moderate risk of poor treatment response, administering additional anti-cancer therapy (optionally more aggressive than said perioperative treatment); or
 (ii) when the patient is determined to be at low risk of poor treatment response, not administering additional anti-cancer therapy or administering additional anti-cancer therapy that is less aggressive than said perioperative treatment.

Aggressive anti-cancer therapy may be as described above in connection with the first aspect of the invention.

In accordance with any aspect of the present invention, the patient may be a human, particularly a human who has been diagnosed as having, or as having a risk of developing, a gastroesophageal cancer. In some cases, the patient has had chemotherapy for gastroesophageal cancer and/or has had surgical resection of a gastroesophageal tumour. In some cases the patient may be a plurality of patients. In particular, the methods of the present invention may be for stratifying a group of patients (e.g. for a clinical trial) into high and low risk or into high, moderate and low risk subgroups based on their gene expression profiles.

Embodiments of the present invention will now be described by way of example and not limitation with reference to the accompanying figures. However various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
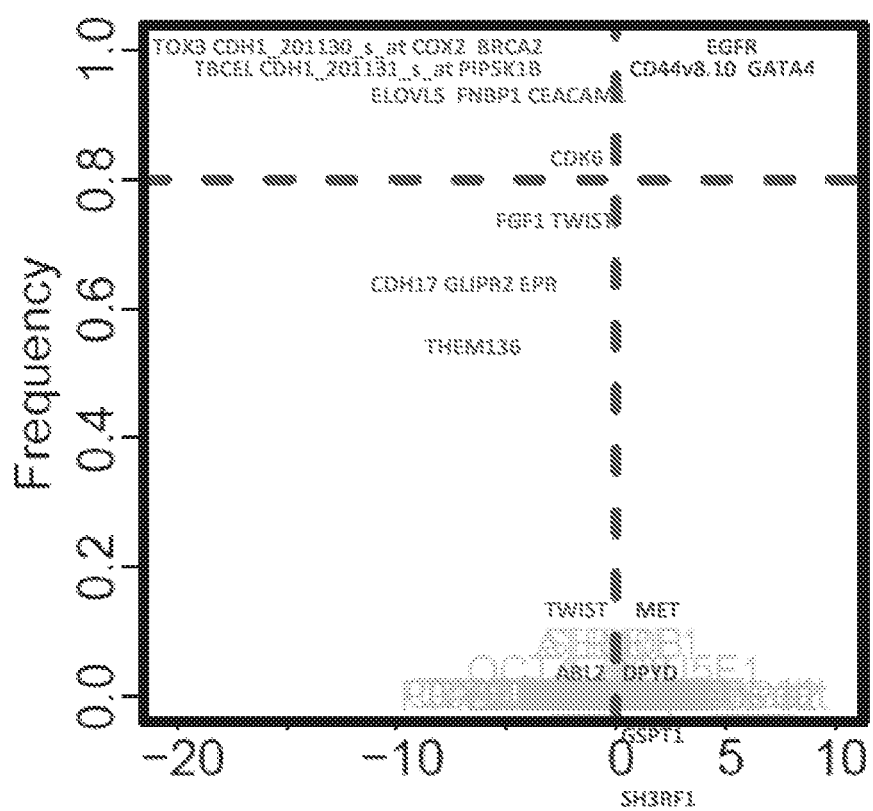
FIG. 1 shows genes associated with overall survival (OS) using regularized Cox regression in chemotherapy treated resection patients only. Deviation from the centre towards the right results in a worse overall survival when a gene is upregulated, and deviation towards the left results in better overall survival when a gene is upregulated. The frequency with which the gene was selected in the Cox regression analysis is depicted by the position of the gene on the y axis.

In describing the present invention, the following terms will be employed, and are intended to be defined as indicated below.

Samples

A "test sample" as used herein may be a cell or tissue sample (e.g. a biopsy), a biological fluid, an extract (e.g. a protein or DNA extract obtained from the subject). In particular, the sample may be a tumour sample, including a gastroesophageal tumour. The sample may be one which has been freshly obtained from the subject or may be one which has been processed and/or stored prior to making a determination (e.g. frozen, fixed or subjected to one or more purification, enrichment or extractions steps).

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Gene Expression

Reference to determining the expression level refers to determination of the expression level of an expression product of the gene. Expression level may be determined at the nucleic acid level or the protein level.

The gene expression levels determined may be considered to provide an expression profile. By "expression profile" is meant a set of data relating to the level of expression of one or more of the relevant genes in an individual, in a form which allows comparison with comparable expression profiles (e.g. from individuals for whom the prognosis is already known), in order to assist in the determination of prognosis and in the selection of suitable treatment for the individual patient.

The determination of gene expression levels may involve determining the presence or amount of mRNA in a sample of cancer cells. Methods for doing this are well known to the skilled person. Gene expression levels may be determined in a sample of cancer cells using any conventional method, for example using nucleic acid microarrays or using nucleic acid synthesis (such as quantitative PCR). For example, gene expression levels may be determined using a NanoString nCounter Analysis system (see, e.g., U.S. Pat. No. 7,473,767).

Alternatively or additionally, the determination of gene expression levels may involve determining the protein levels expressed from the genes in a sample containing cancer cells obtained from an individual. Protein expression levels may be determined by any available means, including using immunological assays. For example, expression levels may be determined by immunohistochemistry (IHC), Western blotting, ELISA, immunoelectrophoresis, immunoprecipitation and immunostaining. Using any of these methods it is possible to determine the relative expression levels of the proteins expressed from the genes listed in Table 3.

Gene expression levels may be compared with the expression levels of the same genes in cancers from a group of patients whose survival time and/or treatment response is known. The patients to which the comparison is made may be referred to as the 'control group'. Accordingly, the determined gene expression levels may be compared to the expression levels in a control group of individuals having cancer. The comparison may be made to expression levels determined in cancer cells of the control group. The comparison may be made to expression levels determined in samples of cancer cells from the control group. The cancer in the control group may be the same type of cancer as in the individual. For example, if the expression is being determined for an individual with gastric cancer, the expression levels may be compared to the expression levels in the cancer cells of patients also having gastric cancer.

Other factors may also be matched between the control group and the individual and cancer being tested. For example the stage of cancer may be the same, the subject and control group may be age-matched and/or gender matched.

Additionally the control group may have been treated with the same form of surgery and/or same chemotherapeutic treatment. For example, if the subject has been or is being treated with docetaxel, oxaliplatin and 5FU, all of the patients in the control group(s) may have been treated with docetaxel, oxaliplatin and 5FU.

Accordingly, an individual may be stratified or grouped according to their similarity of gene expression with the group with good or poor prognosis.

Methods for Classification Based on Gene Expression

In some embodiments, the present invention provides methods for classifying, prognosticating, or monitoring gastric cancer in subjects. In particular, data obtained from analysis of gene expression may be evaluated using one or more pattern recognition algorithms. Such analysis methods may be used to form a predictive model, which can be used to classify test data. For example, one convenient and particularly effective method of classification employs multivariate statistical analysis modelling, first to form a model (a "predictive mathematical model") using data ("modelling data") from samples of known subgroup (e.g., from subjects known to have a particular gastric cancer prognosis subgroup: high risk, moderate risk and low risk), and second to classify an unknown sample (e.g., "test sample") according to subgroup.

Pattern recognition methods have been used widely to characterize many different types of problems ranging, for example, over linguistics, fingerprinting, chemistry and psychology. In the context of the methods described herein, pattern recognition is the use of multivariate statistics, both parametric and non-parametric, to analyse data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of gene expression data is used to construct a statistical model that predicts correctly the "subgroup" of each sample. This training set is then tested with independent data (referred to as a test or validation set) to determine the robustness of the computer-based model. These models are sometimes termed "expert systems," but may be based on a range of different mathematical procedures such as support vector machine, decision trees, k-nearest neighbour and naïve Bayes. Supervised methods can use a data set with reduced dimensionality (for example, the first few principal components), but typically use unreduced data, with all dimensionality. In all cases the methods allow the quantitative description of the multivariate boundaries that characterize and separate each subtype in terms of its intrinsic gene expression profile. It is also possible to obtain confidence limits on any predictions, for example, a level of probability to be placed on the goodness of fit. The robustness of the predictive models can also be checked using cross-validation, by leaving out selected samples from the analysis.

After stratifying the training samples according to subtype, a centroid-based prediction algorithm may be used to construct centroids based on the expression profile of the gene set described in Table 3.

"Translation" of the descriptor coordinate axes can be useful. Examples of such translation include normalization and mean-centering. "Normalization" may be used to remove sample-to-sample variation. Some commonly used methods for calculating normalization factor include: (i) global normalization that uses all genes on the microarray or nanostring codeset; (ii) housekeeping genes normalization that uses constantly expressed housekeeping/invariant genes; and (iii) internal controls normalization that uses known amount of exogenous control genes added during hybridization (Quackenbush (2002) Nat. Genet. 32 (Suppl.), 496-501). In one embodiment, the genes listed in Table 3 can be normalized to one or more control housekeeping genes. Exemplary housekeeping genes include ACTB (60), GAPDH (2597) and TBP (6908), the numbers in brackets following each gene name being the NCBI Gene ID number for that gene; the nucleotide sequence for each gene as disclosed at that NCBI Gene ID number on 8 Oct. 2017 is expressly incorporated herein by reference. It will be understood by one of skill in the art that the methods disclosed herein are not bound by normalization to any particular housekeeping genes, and that any suitable housekeeping gene(s) known in the art can be used. Many normalization approaches are possible, and they can often be applied at any of several points in the analysis. In one embodiment, microarray data is normalized using the LOWESS method, which is a global locally weighted scatterplot smoothing normalization function. In another embodiment, qPCR and NanoString nCounter analysis data is normalized to the geometric mean of set of multiple housekeeping genes. Moreover, qPCR can be analysed using the fold-change method.

"Mean-centering" may also be used to simplify interpretation for data visualisation and computation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

When comparing data from multiple analyses (e.g., comparing expression profiles for one or more test samples to the centroids constructed from samples collected and analyzed in an independent study), it will be necessary to normalize data across these data sets. In one embodiment, Distance Weighted Discrimination (DWD) is used to combine these data sets together (Benito et al. (2004) Bioinformatics 20(1): 105-114, incorporated by reference herein in its entirety). DWD is a multivariate analysis tool that is able to identify systematic biases present in separate data sets and then make a global adjustment to compensate for these biases; in essence, each separate data set is a multi-dimensional cloud of data points, and DWD takes two points clouds and shifts one such that it more optimally overlaps the other. Further methods for combining data sets include the "ComBat" method and others described in Lagani et al., *BMC Bioinformatics,* 2016, Vol. 17(Suppl 5): 290, the entire contents of which is expressly incorporated herein by reference. ComBat is a method specifically devised for removing batch effects in gene-expression data (Johnson W E, Li C, Rabinovic A. Adjusting batch effects in microarray expression data using empirical Bayes methods. *Biostatistics.* 2007; 8:118-27, the entire contents of which is expressly incorporated herein by reference).

In some embodiments described herein, the prognostic performance of the gene expression signature and/or other clinical parameters is assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard (i.e., risk) of individuals given their prognostic variables (e.g., gene expression profile with or without additional clinical factors, as described herein). The "hazard ratio" is the risk of death at any given time point for patients displaying particular prognostic variables.

Genes Making Up the Gene Signature or Gene Expression Profile

In accordance with any aspect of the present invention, the genes that make up the gene expression profile may be selected from any 3, 4, 5, 6, 7 or more (such as all of the) genes selected from the following group: CDH1 (999), CDK6 (1021), COX2 (5743), ELOVL5 (60481), GATA4 (2626), EGFR (1956), TBCEL (219899), FGF7 (2252), CDH17 (1015), FNBP1 (23048), PIP5K1B (8395), TWIST (7291), CD44 (960), MET (4233), CEACAM1 (634), TOX3 (27324), GLIPR2 (152007), GSTP1 (2950), RON (4486), TMEM136 (219902), MYB (4602), BRCA2 (675), FGF1 (2246), POU5F1 (5460), EPR (2069), DPYD (1806), ABL2 (27) and SH3RF1 (57630), the number in brackets following each gene name being the NCBI Gene ID number for that gene; the nucleotide sequence for each gene as disclosed at that NCBI Gene ID number on 8 Oct. 2017 is expressly incorporated herein by reference. Particular subsets of the said genes are contemplated herein. For example, the genes CDH1, COX2, ELOVL5, GATA4 and EGFR exhibit the lowest p-values in the Cox regression analysis results shown in Table 3 and therefore said genes may provide a compact signature of genes whose expression is significantly associated with survival (improved by high expression for CDH1, COX2, ELOVL5; made worse by high expression for GATA4 and EGFR). A particularly preferred gene expression profile is that of the seven genes: CDH1, CDK6, COX2, ELOVL5, GATA4, EGFR and TBCEL. In some cases the CDH1 gene expression is of the CDH1 gene as associated with probe 201130_s_at of Affymetrix GeneChip Human Genome U133 Plus 2.0 Array. Alternatively or additionally, in some cases, the CDH1 gene expression is of the CDH1 gene as associated with probe 201131_s_at of Affymetrix GeneChip Human Genome U133 Plus 2.0 Array. In some case, CD44 expression is of the v8-10 isoform.

Prognosis

An individual grouped with the good prognosis group, may be identified as having a cancer that is sensitive to chemotherapy, e.g. perioperative chemotherapy for gastric cancer, they may also be referred to as an individual that responds well to chemotherapy treatment. An individual grouped with the poor prognosis group, may be identified as having a cancer that is resistant to chemotherapy treatment, including perioperative chemotherapy for gastric cancer.

Where the individual is grouped with the good prognosis group, the individual may be selected for treatment with suitable chemotherapy as described in further detail below. Where the individual is grouped with the poor prognosis group, the individual may be deselected for treatment with the aforementioned chemotherapy and may, for example, receive surgical treatment alone or surgery plus a novel or experimental therapy, including immunotherapy.

Whether a prognosis is considered good or poor may vary between cancers and stage of disease. In general terms a good prognosis is one where the overall survival (OS) and/or progression-free survival (PFS) is longer than average for that stage and cancer type. A prognosis may be considered poor if PFS and/or OS is lower than average for that stage and type of cancer. The average may be the mean OS or PFS.

For example, a prognosis may be considered good if the PFS is >6 months and/or OS>18 months. Similarly PFS of <6 months or OS of <18 months may be considered poor. In particular PFS of >6 months and/or OS of >18 months may be considered good for advanced cancers. As described in detail herein, the present inventors found that classification based on the gene expression model of the present invention was able to group patients into high risk, moderate risk and low risk subgroups. The median overall survival for high risk patients was 0.54 years (95% CI 0.42-0.98 years) for high risk patients, 2.07 years (95% CI 1.41-4.46 years) for patients in the intermediate risk group, and was not reached for patients in the low risk group.

In general terms, a "good prognosis" is one where survival (OS and/or PFS) of an individual patient can be favourably compared to what is expected in a population of patients within a comparable disease setting. This might be defined as better than median survival (i.e. survival that exceeds that of 50% of patients in population).

"Predicting the likelihood of survival of a gastric cancer patient" is intended to assess the risk that a patient will die as a result of the underlying gastric cancer.

"Predicting the response of a gastric cancer patient to a selected treatment" is intended to mean assessing the likelihood that a patient will experience a positive or negative outcome with a particular treatment.

As used herein, "indicative of a positive treatment outcome" refers to an increased likelihood that the patient will experience beneficial results from the selected treatment (e.g. reduction in tumour size, 'good' prognostic outcome, improvement in disease-related symptoms and/or quality of life).

"Indicative of a negative treatment outcome" is intended to mean an increased likelihood that the patient will not receive the aforementioned benefits of a positive treatment outcome.

Gastroesphogeal Cancer

As used herein, "gastroesphogeal cancer" refers to any gastric cancer, stomach cancer, or cancer of the oesophagus, and specifically includes secondary or metastatic tumours or microtumours that have spread from the primary site, such as the lining of the stomach to other sites (e.g. to liver, lungs, bones, lining of the abdomen and lymph nodes).

Chemotherapy

Perioperative chemotherapy with ECX (epirubicin, cisplatin and 5-fluourouracil (5FU) (either infused or oral capecitabine) was a standard of care from 2006-2017.

Cisplatin and 5FU or Oxaliplatin and 5FU are reasonable substitutes for this based on the REAL2 trial; this is accepted in guidelines (ESMO Gastric Cancer).

In 2017 a novel regimen of docetaxel, oxaliplatin and 5FU (FLOT) was demonstrated to be superior to ECX, and will become a new standard of care for gastric cancer.

The gene expression signature of the present invention was derived only in patients treated with ECX, however, without wishing to be bound by any particular theory, the present inventors believe that patients treated with a platinum-based chemotherapeutic and/or 5FU will display comparable outcome predictive power (i.e. treatment response prediction) for the said gene expression signature.

The following is presented by way of example and is not to be construed as a limitation to the scope of the claims.

EXAMPLES

Materials and Methods
Collection of MAGIC Trial Samples
Paraffin-embedded samples from the diagnostic biopsy and resection (where applicable) were requested for all 503 patients randomised. Approval was obtained from institutional review boards according to local and national requirements.

Selection of Genes for Analysis

Two hundred genes relevant to gastric cancer were selected for analysis plus three control genes (Table 1). In addition to genes representing the two intrinsic subtypes (G-INT and G-DIFF), we also selected for genes which had relevance for gastric cancer for other reasons. These were:

Chemotherapy sensitivity (e.g. MYC, COX2, STAT3, HIF1A) or platinum sensitivity (e.g. ERCC1/2, BRCA1/2, OPRT). Thirty six genes were selected in this category.

Genes frequently amplified in gastric cancer (e.g. FGFR2, ERBB2, KRAS) or genes frequently deleted in gastric cancer (e.g. FHIT, CDKN2A, CDKN2B, RB1). Fifty four genes were selected in this category.

Genes which had differentiated the two intrinsic subtypes in previous work (e.g. TOX3, MYB, CEACAM1 for G-INT) and (e.g. ABL2, SIX4, RASSF8 for G-DIFF). One hundred and ten genes were selected in this category.

The housekeeping genes chosen were ACTB, GAPDH and TBP which have been suggested as consensus reference genes for gene expression studies.[317]

TABLE 1

| Genes included in NanoString panel |
|---|
| NanoString Panel Gene |
| FGFR2 |
| CCNE1 |
| KRAS |
| GATA6 |
| CDK6 |
| GATA4 |
| CCND1 |
| EGFR |
| ERBB2 |
| MET |
| FHIT |
| CSMD1 |
| CDKN2A, CDKN2B |
| GMDS |
| WWOX |
| PARK2 |
| RB1 |
| PDE4D |
| PTPRD |
| ERCC1 |
| ERCC2 |
| XRCC1 |
| DPYD |
| OPRT |
| GSTP1 |
| GSTT1 |
| BRCA1 |
| BRCA2 |
| MRP1 |
| MRP2 |
| CDH1 |
| MGMT |
| TOP2 |
| MTHFR |
| TYMS |
| RDX |
| TSPAN8 |
| TBCEL |
| FERMT2 |
| GPX2 |
| LYZ |
| MYO5A |
| SOAT1 |
| LGALS4 |

TABLE 1-continued

| Genes included in NanoString panel |
|---|
| NanoString Panel Gene |
| PLS1 |
| C5orf32 |
| FUT2 |
| FADS1 |
| MYH10 |
| ATAD4 |
| DEGS2 |
| FNBP1 |
| NOSTRIN |
| ELOVL5 |
| MUC13 |
| ALDH3A1 |
| MYO1A |
| ABL2 |
| ABCC3 |
| AGR3 |
| VILL |
| PGBD1 |
| SH3RF1 |
| TRAK1 |
| SELM |
| EGLN3 |
| BCL2L14 |
| CDH17 |
| CEACAM1 |
| LOXL2 |
| LIPH |
| RSPH1 |
| SEPT6 |
| FZD2 |
| KALRN |
| KIAA1586 |
| CAPN8 |
| CLCN3 |
| PLEK2 |
| TMC5 |
| RASSF8 |
| NUAK1 |
| TMEFF1 |
| CYP3A5 |
| SCHIP1 |
| FAM101B |
| TMEM136 |
| ZCCHC11 |
| EPS8L3 |
| FAM127A |
| FA2H |
| TOX3 |
| SIX4 |
| DENND5A |
| BAIAP2L2 |
| TTC7B |
| ZNF512B |
| KIRREL |
| GNB4 |
| PIP5K1B |
| AGPAT2 |
| BCL2L15 |
| TNFRSF11A |
| FN1 |
| PLCH1 |
| GPR35 |
| GJC1 |
| ATP10B |
| TC2N |
| MMP28 |
| GLIPR2 |
| CYP3A5 |
| LLGL2 |
| CAPN10 |
| TRNP1 |
| DSE |
| FJX1 |
| SDCBP2 |
| MYB |
| ACSM3 |
| DNAH14 |

TABLE 1-continued

Genes included in NanoString panel
NanoString Panel Gene

ENAH
REG4
CYP2C18
CALD1
GPRASP2
PRR15
DLX1
GLT8D4
HEG1
HNF4G
KLF5
LPHN2
PTPRS
SGK493
TIMP3
TMEM45B
UGT8
RNF128
FRMD6
KCNE3
LOC100133019
DNAJC22
SNAP47
ST6GALNAC1
FGF1
FGF2
FGF20
FGF3
FGF5
FGF7
VEGFA
HGF
EGF
DPYSL3
MYL9
TAGLN
PTRF
FBN1
CALD1
BMP4
TP53
PIK3CA
CTNNB1
APC
PTEN
ARID1A
FAT4
MLH1
MSH2
FGFR2 IIIb
CD44
CD44v8-10
WNT5A
WNT7B
AXIN2
WNT6
WNT1
CDH1
PPP1R1bB (DARPP32)
MYC
BIRC5 (survivin)
GAS1
COX2
IGF1R
STAT3
HIF1a
RON
CDKN1A (p21)
HER3
HRG
EPR
AREG
OCT4 (POU5F1)
SOX2
NANOG
TWIST TABLE 1-continued Genes included in NanoString panel
NanoString Panel Gene

SNAIL
SLUG

NanoString Assessment

For the nCounter assay, 100 ng of total RNA was hybridized with the custom designed code set of 200 genes and processed according to manufacturer's instruction. The final hybridisation was at 65° C. Maximum hybridization time did not exceed 30 hours.

For normalisation of NanoString data, NanoStringNorm Package in R or nSolver (NanoString Technology) package was used.[318]

Normalisation was performed using a standard approach, i.e. data was normalised using both control probes and housekeeping genes.

Positive spike-in RNA hybridization controls for each lane were summed to estimate the overall efficiency of hybridization and recovery for each lane. Background for each lane was determined from the negative control counts.

Data were then log transformed and multidimensional scaling plots and principle component analysis were performed to assess for further technical variation or batch effects.

Samples were classified into G-INT or G-DIFF signatures using the Nearest-Template-Prediction (NTP) algorithm employing both weighted and unweighted analyses.[319]

For assessment of RTK/RAS markers "high" and "low" expressers for each marker gene are defined based on deviation in qq-plot.

Methodology of New Model Generation

Regularised Cox Regression was used to detect genes which were significantly associated with overall survival in patients treated with chemotherapy plus surgery. Regularised Cox prediction was used because overfitting of data in gene expression model generation is a common cause of models which have poor predictive power in validation sets. This is common when the number of parameters in the model (e.g. genes) is higher than the number of observations.

An overfitted model is too trained on "noise" in the dataset and is completely dependent on it. In regularized Cox regression, a penalty is introduced for complexity (such as adding the coefficients of the model into the minimization) in order to try to avoid overfitting.

Reference Example 1—Prognostic Effect of
G-INT/G-DIFF Intrinsic Subtypes

Five hundred and three patients were randomised to surgery alone or perioperative chemotherapy plus surgery in the MAGIC trial, of which 456 (91%) underwent surgery and had a date available for further analysis. Gene expression data was available for 204 patients who underwent surgery with a date available in the MAGIC trial.

Two hundred and nineteen patients were characterised, and twenty two technical replicates were performed. However, dates of surgery were only available for 204 of these patients, and therefore only those patients were analysed for survival.

Using an FDR ratio of <0.05 72 (35.3%) were characterised as G-INT, 69 (33.8%) were characterised as G-DIFF and 63 (30.9%) were classified as ambiguous.

Therefore, the MAGIC population contains a significant proportion of patients who could not be characterised using the G-INT and G-DIF gene expression signature and NTP algorithm.

The prognostic effect of subgroup was compared in all patients and in each arm of the trial separately (Table 2).

TABLE 2

Prognostic effects of intrinsic subtype by treatment arm and entire populations

| | Subjects | Events | mOS | 95% CI | HR | 95% CI | P |
|---|---|---|---|---|---|---|---|
| All patients | | | | | | | |
| G-INT | 71 | 48 | 1.30 | 1.13-2.46 | 1.0 | | |
| G-DIFF | 68 | 47 | 1.40 | 0.95-1.84 | 1.05 | 0.70-1.57 | 0.81 |
| Amb | 63 | 47 | 1.94 | 0.95-3.27 | 0.98 | 0.65-1.47 | 0.91 |
| Chemotherapy plus surgery arm | | | | | | | |
| G-INT | 26 | 16 | 1.82 | 0.93-6.64 | 1.0 | | |
| G-DIFF | 42 | 28 | 1.41 | 0.95-3.51 | 1.17 | 0.63-2.17 | 0.609 |
| Amb | 19 | 13 | 1.86 | 0.84-4.46 | 1.10 | 0.53-2.28 | 0.807 |
| Surgery alone arm | | | | | | | |
| G-INT | 45 | 32 | 1.28 | 1.13-2.31 | 1.0 | | |
| G-DIFF | 26 | 19 | 1.36 | 0.45-1.84 | 1.03 | 0.58-1.82 | 0.912 |
| Amb | 44 | 32 | 2.09 | 0.87-3.27 | 0.90 | 0.55-1.48 | 0.685 |

There were no statistically significant differences in overall survival between intrinsic subtypes in either arm of the trial, or in the population overall. However, the number of patients in each group is small, limiting power to draw conclusions.

In the surgery alone arm of the trial, G-INT and G-DIFF patients had comparable survival, however in the chemotherapy plus surgery arm, survival was marginally better for G-INT (and ambiguous), although these differences were not statistically significant. If gene expression status is unchanged post chemotherapy this could suggest that G-INT patients might derive more benefit from chemotherapy than G-DIFF. However, because of the high event rate in the population as a whole and the small number of patients in each subset, any difference would need to be very large to attain statistical significance and clinical relevance.

Example 2—Generation of a New Prognostic Gene Expression Signature

In view of the lack of statistically significant prognostic or predictive effect of the G-INT and G-DIFF subtypes in the MAGIC dataset (Reference example 1 above), the present inventors wished to perform further analyses using this dataset. In particular, it was considered that it would be helpful to identify patients who are high or low risk for recurrence following chemotherapy and resection for consideration of further treatment or not.

Accordingly, the NanoString analysis was repeated including normalisation for control and housekeeping genes. Following this a regularised Cox regression approach (see Methods above) was followed which in order to a) identify individual genes which are associated with overall survival in the chemotherapy+surgery treated patients and b) group these genes as a signature in order to identify high and low risk groups of patients based on gene expression only in post-chemotherapy resection specimens.

Penalized Cox regression was used to model the overall survival using gene expression of the chemotherapy treated patients and is depicted in FIG. 1. Deviation from the centre towards the right results in a worse overall survival when a gene is upregulated, and deviation towards the left results in better overall survival when a gene is upregulated. The frequency with which the gene was selected in the Cox regression analysis is depicted by the position of the gene on the y axis. The analysis was performed 100 times (therefore a frequency of 0.9 means a gene was selected in 90/100 runs of the regression experiment).

Thirty-four genes were selected by regularized Cox regression, of which 16 were selected more than 80% of the time. We then applied standard Cox regression to these 16 genes.

We found that 7 of the 16 genes were significantly associated with survival using this method.

Genes and expression levels which were associated with a lower risk of death are detailed in Table 3 below. Genes which were associated with improved survival when upregulated and those which were associated with worse survival when upregulated are indicated, respectively, in the final column.

TABLE 3

Genes associated with overall survival on Cox regression

| Gene | *NCBI Gene ID No. | HR | p value | Improved/worse survival |
|---|---|---|---|---|
| CDH1 | 999 | 0.47893519 | <0.00001 | Improved |
| CDK6 | 1021 | 0.86568645 | 0.043048 | Improved |
| COX2 | 5743 (human) | 0.60951164 | 0.00562 | Improved |
| ELOVL5 | 60481 | 0.66837402 | 0.000771 | Improved |
| GATA4 | 2626 | 1.23187407 | 0.007323 | Worse |
| EGFR | 1956 | 1.36866119 | 0.002253 | Worse |
| TBCEL | 219899 | 0.68325777 | 0.036071 | Improved |

*NCBI Gene ID No. refers to the gene sequence record available on 8 Oct. 2017 at ncbi.nlm.nih.gov/gene/ retrievable using the said number in column 2 for the human gene named in column 1, the complete nucleotide sequence of which is expressly incorporated herein by reference.

Example 3—Generation of High and Low Risk Groups Using Genes Selected in Cox Regression Models The expression levels of the seven genes shown in Table 3 were then used to develop a risk score. The individual risk score for each patient was a product of the expression of each gene multiplied by the hazard ratio associated with that gene in Cox regression. Patients were then dichotomised according to risk score split at the median.

Figure 2:
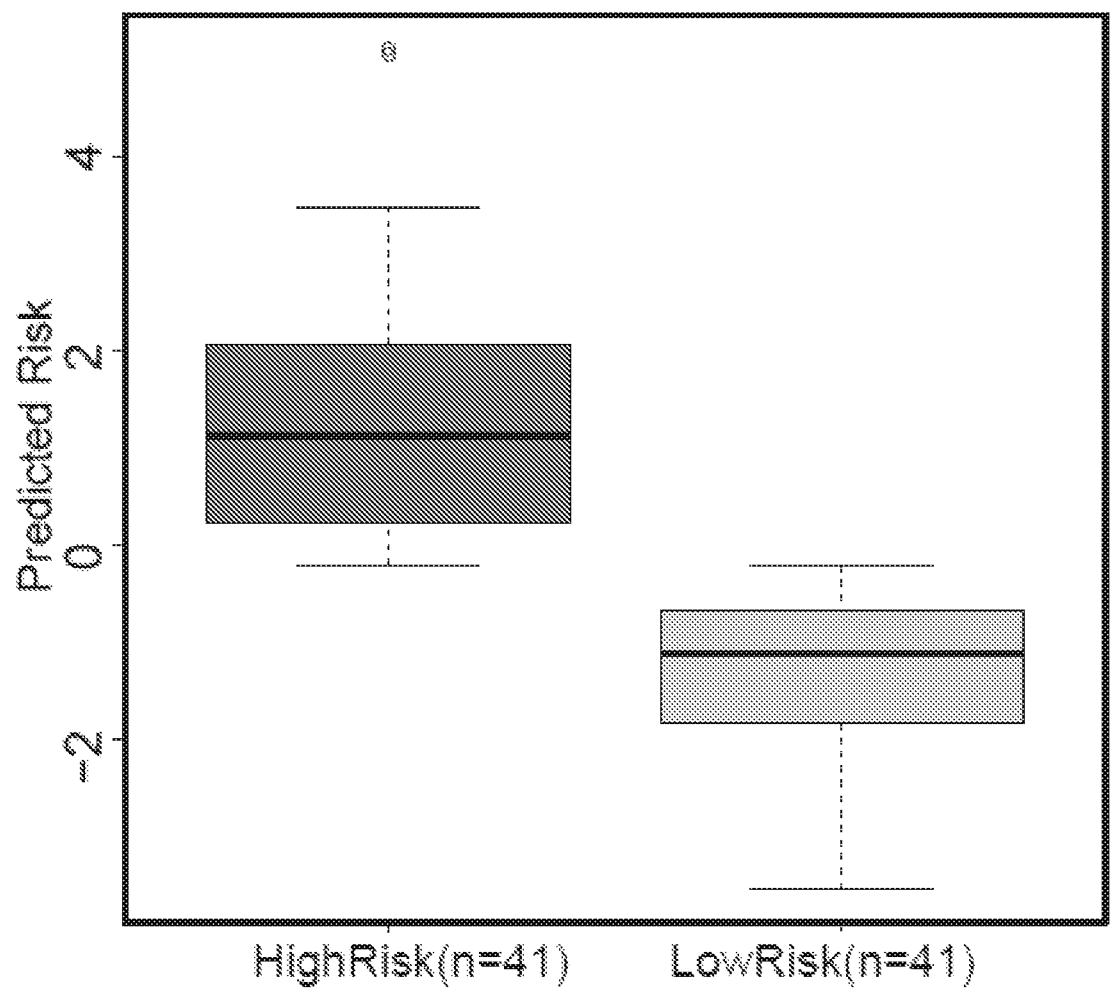
FIG. 2 shows a box and whiskers plot demonstrating predicted risk of death in high and low risk groups in chemotherapy treated patients.

FIG. 2 demonstrates a box and whisker plots plot with the predicted risk of death for high and low risk groups.

Figure 3:
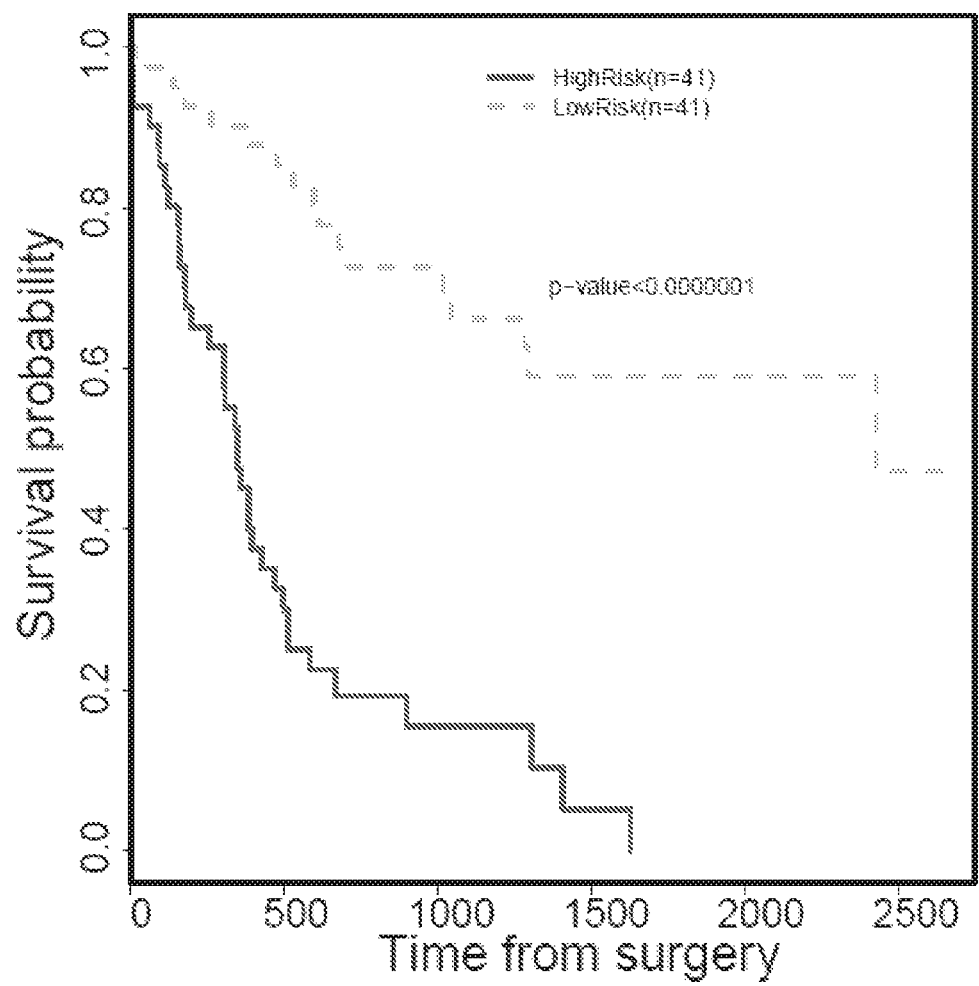
FIG. 3 shows overall survival (OS) from surgery in high and low risk groups (chemo+surgery arm) depicted as a Kaplan-Meier curve. The survival probability is shown on the y-axis and time from surgery is shown on the x-axis. The high risk group (n=41) is shown with a solid line. The low risk group (n=41) is shown with a dashed line. A p value of p<0.0000001 is shown.

FIG. 3 demonstrates a Kaplan-Meier curve depicting the survival of the high and low risk group in chemotherapy treated patients. When divided into high risk and low risk groups, median survival was 6.65 years (95% CI 3.51 years—not reached) for the low risk group, and 0.95 years (95% CI 0.70-1.36 years) for the high risk group. This suggests that this signature may have prognostic value in patients treated with chemotherapy who undergo resection.

Risk scores were then allocated into one of three groups using a K-means clustering model, which produced groups of high, medium and low risk for recurrence. K-means clustering calculates the distance between a sample measurement and the current group (centroid) average for that measurement. The sample is added to the group, to which it is closest to in measurement, and a new mean is then calculated for that group, and this process is repeated for each sample.

Figure 4:
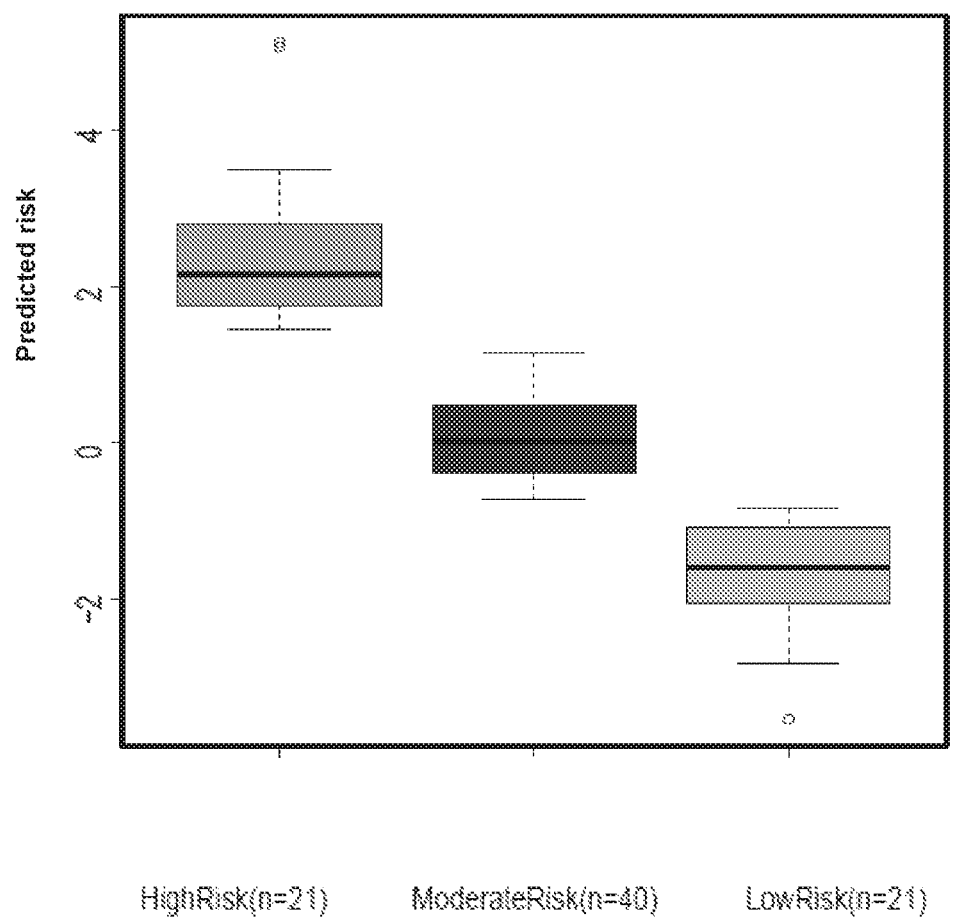
FIG. 4 shows a box and whiskers plot demonstrating predicted risk of death in high (n=21), intermediate (n=40) and low risk (n=21) groups in chemotherapy treated patients.

FIG. 4 shows a Box and whiskers plot demonstrating predicted risk of death in high, intermediate and low risk groups in chemotherapy treated patients.

Figure 5:
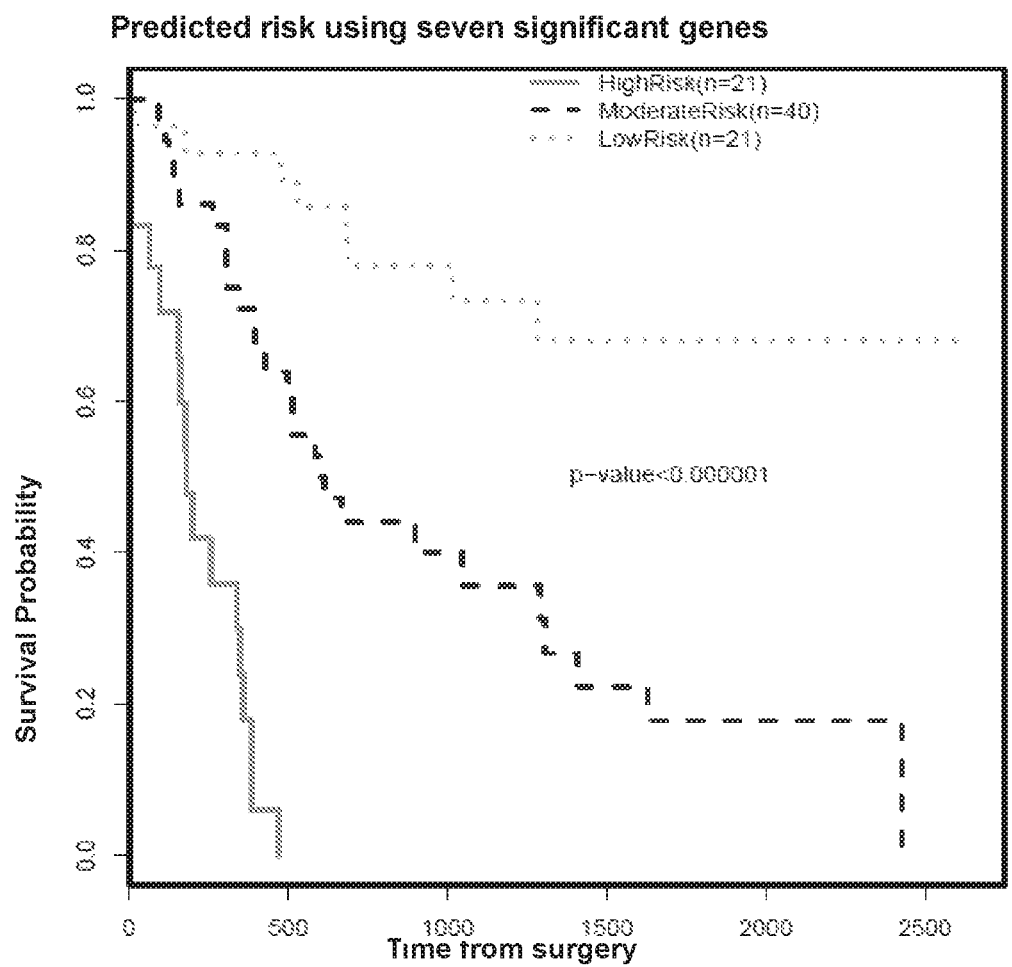
FIG. 5 shows a Kaplan-Meier curve depicting the survival of the high (n=21; solid line), medium (n=40; dashed line) and low risk (n=21; dotted line) groups in chemotherapy treated patients (chemo+surgery arm). The survival probability is shown on the y-axis and time from surgery is shown on the x-axis. A p value of p<0.000001 is shown.

FIG. 5 demonstrates a Kaplan-Meier curve depicting the survival of the high, medium and low risk group in chemotherapy treated patients. When three risk groups were created the median overall survival for high risk patients was 0.54 years (95% CI 0.42-0.98 years) for high risk patients, 2.07 years (95% CI 1.41-4.46 years) for patients in the intermediate risk group and was not reached for patients in the low risk group.

These data, and those above, suggest that assessment of gene expression in specimens from patients who have undergone chemotherapy plus surgery for operable gastroesophageal cancer could provide useful prognostic information. However, these analyses contain small numbers of patients and are univariate with respect to other factors which may predict for survival (lymph node status and mismatch repair status).

Example 4—Multivariate Analysis of Risk Groups Including Lymph Node Status

In order to evaluate whether risk group was an independent predictor of survival in patients treated with chemotherapy, multivariate analysis was performed including known predictive variables including nodal status and risk group. Mismatch repair status was not included due to the small number of patients in that population.

Risk group was found to be an independent predictor of overall survival, along with nodal status. The magnitude of benefit which is associated with being in a low risk group is detailed in Table 4, below. Patients in the low risk group (vs. high risk dichotomised by median) have a HR of survival of 0.02601, independent of nodal status. Similarly, when survival was clustered into three groups, patients in the medium and low risk groups had a HR for overall survival of 0.1492 and 0.0402 respectively (Table 5).

These data suggest that the gene expression-identified risk groups provide prognostic information beyond nodal status, and are thus a more useful predictor of survival than tumour response grading.

TABLE 4

Multivariate analysis of OS in chemotherapy treated patients (2 group model)

|  | HR | P value |
| --- | --- | --- |
| Node positive | 3.2959 | 0.03451 |
| Risk Group (Low) | 0.02601 | 0.00026 |

TABLE 5

Multivariate analysis of OS in chemotherapy treated patients (3 group model)

|  | HR | P value |
| --- | --- | --- |
| Node positive | 3.6333 | 0.0176 |
| Risk Group (Mod) | 0.1492 | <0.0001 |
| Risk Group (Low) | 0.0402 | <0.0001 |

Example 5—Assessment of Prognostic Value of Risk Groups in Surgery-Only Treated Patients As the gene signature for risk groups had been identified using chemotherapy treated patients, it was necessary to establish whether this was prognostic only in that group, or also in surgically treated patients.

None of the genes which were associated with overall survival in chemotherapy treated patients were statistically significantly associated with overall survival in the surgery alone arm of the trial. The results of this analysis are detailed in Table 6 below.

TABLE 6

Prognostic role of gene signature genes in surgery only patients

| Gene | HR | p value |
| --- | --- | --- |
| CDH1 | 0.891699 | 0.1743 |
| CDK6 | 1.27874 | 0.0777 |
| COX2 | 0.898601 | 0.4437 |
| ELOVL5 | 1.025455 | 0.8518 |
| GATA4 | 1.00259 | 0.9691 |
| EGFR | 1.009131 | 0.9302 |
| TBCEL | 0.870739 | 0.4066 |

Figure 6:
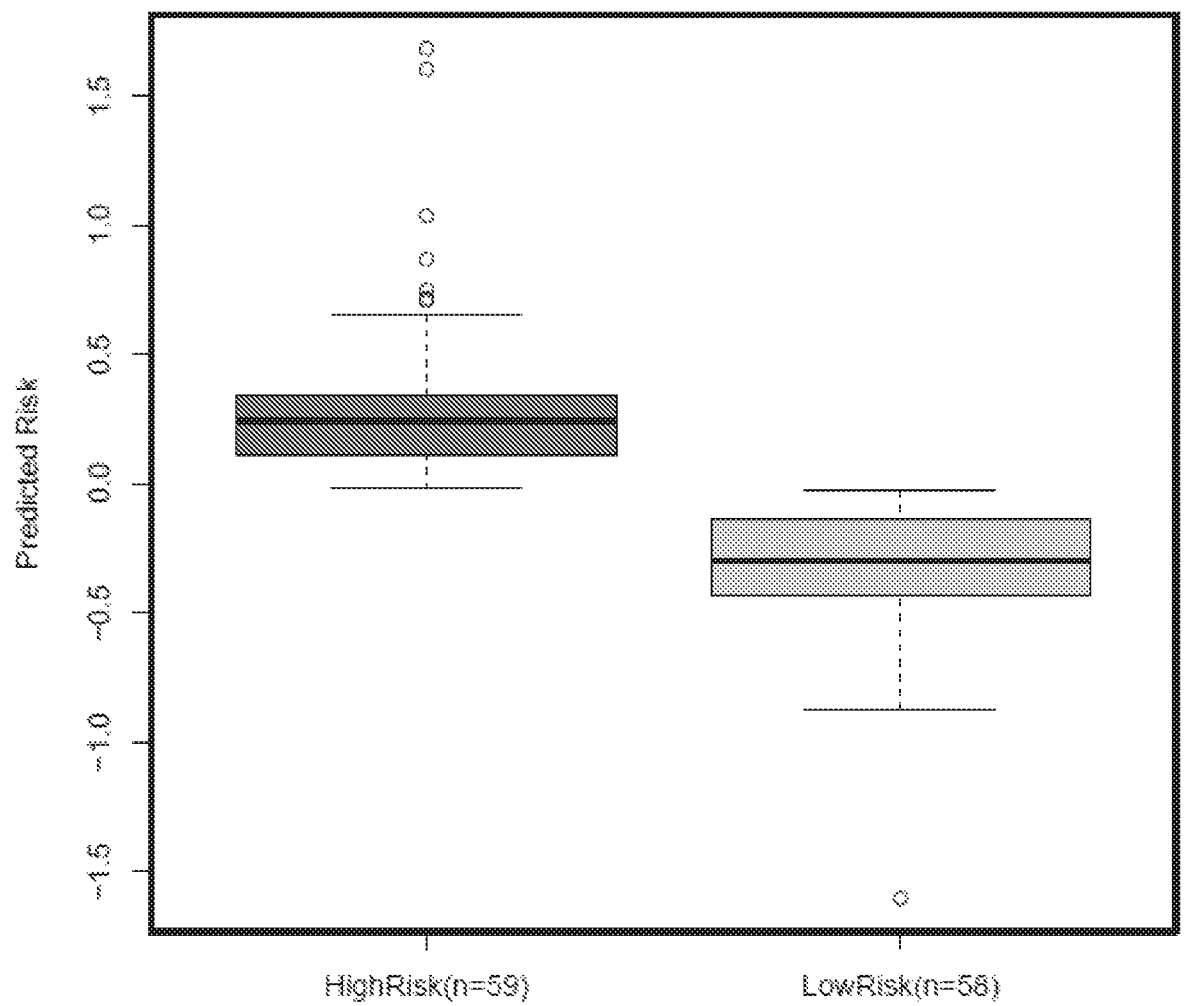
FIG. 6 shows a box and whiskers plot demonstrating predicted risk of death in high and low risk groups in surgically-only treated patients.
Figure 7:
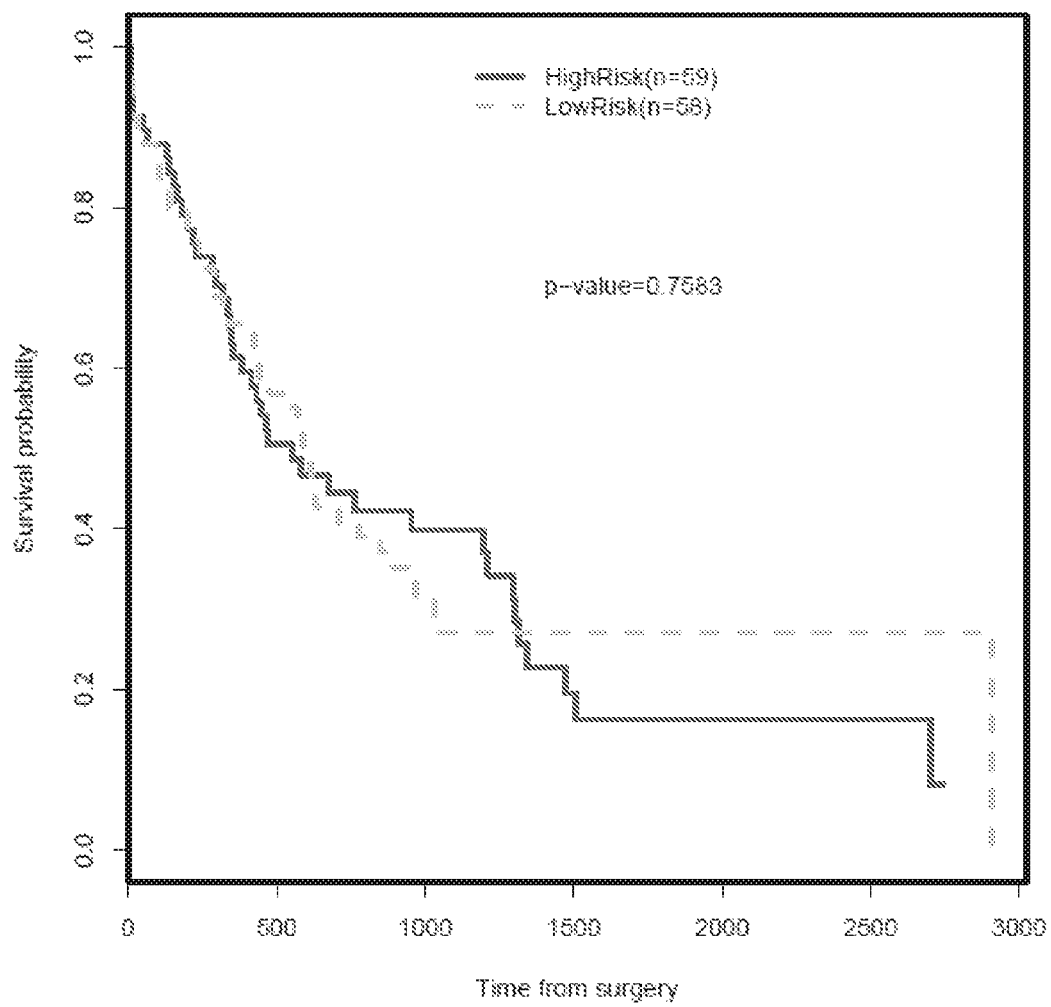
FIG. 7 shows a Kaplan-Meier curve depicting the survival of the high (n=59; solid line) and low risk (n=58; dashed line) groups in surgery-only treated patients (surgery alone arm). The survival probability is shown on the y-axis and time from surgery is shown on the x-axis. A p-value of p=0.7583 is shown.

The same risk-signature was applied to the surgery alone patient cohort; there was no significant increase in risk of death in high risk patients versus low risk patients (FIG. 6), and median survival was equivalent for high and low risk groups (FIG. 7). Multivariate analysis confirmed that risk score was not prognostic for survival in these patients (Table 7).

TABLE 7

Multivariate analysis of overall survival in surgery-only-treated patients (2 group model).

|  | HR | P value |
| --- | --- | --- |
| Node positive | 1.865 | 0.0532 |
| Risk Group (Low) | 0.8901 | 0.6413 |

Further validation of the present 7-gene expression signature in a separate cohort of neoadjuvantly treated resected gastroesophageal cancer patients is contemplated herein.

Example 6—Further Development and Validation of the Prognostic Gene Expression Signature Introduction Perioperative chemotherapy is one standard treatment option for patients with resectable gastric and esophageal cancer; this multimodality therapy leads to cure for approximately 50% of patients.[1-4] Improved post-operative risk stratification would be valuable in order to focus development of novel treatments on patients who are most likely to relapse. However, extraction of DNA and RNA from pre-chemotherapy biopsy samples is challenging and limits the applicability of molecular stratification for making pre-operative treatment decisions. Therefore, a unique approach to prognostic stratification using post-chemotherapy resection specimens may have clinical utility.

The MAGIC trial was a large phase III randomized trial in which patients were treated with either 6 cycles of perioperative epirubicin, cisplatin and 5-fluorouracil (ECF) chemotherapy (three cycles pre- and post-operatively) plus surgery, or with surgery alone. The results of the trial supported a survival benefit for perioperative chemotherapy treated patients and established platinum-fluoropyrimidine based perioperative chemotherapy as one standard of care for resectable gastroesophageal cancer.[1] We hypothesized that by performing transcriptomic analysis on resection specimens from patients treated with perioperative chemotherapy in the MAGIC trial distinct subgroups of patients with different survival outcomes can be identified. Herein, we present the results of this analysis performed in patients from the MAGIC trial, and validated in a second, independent, similar cohort of patients.

Methods

Patient Samples

Figure 8:
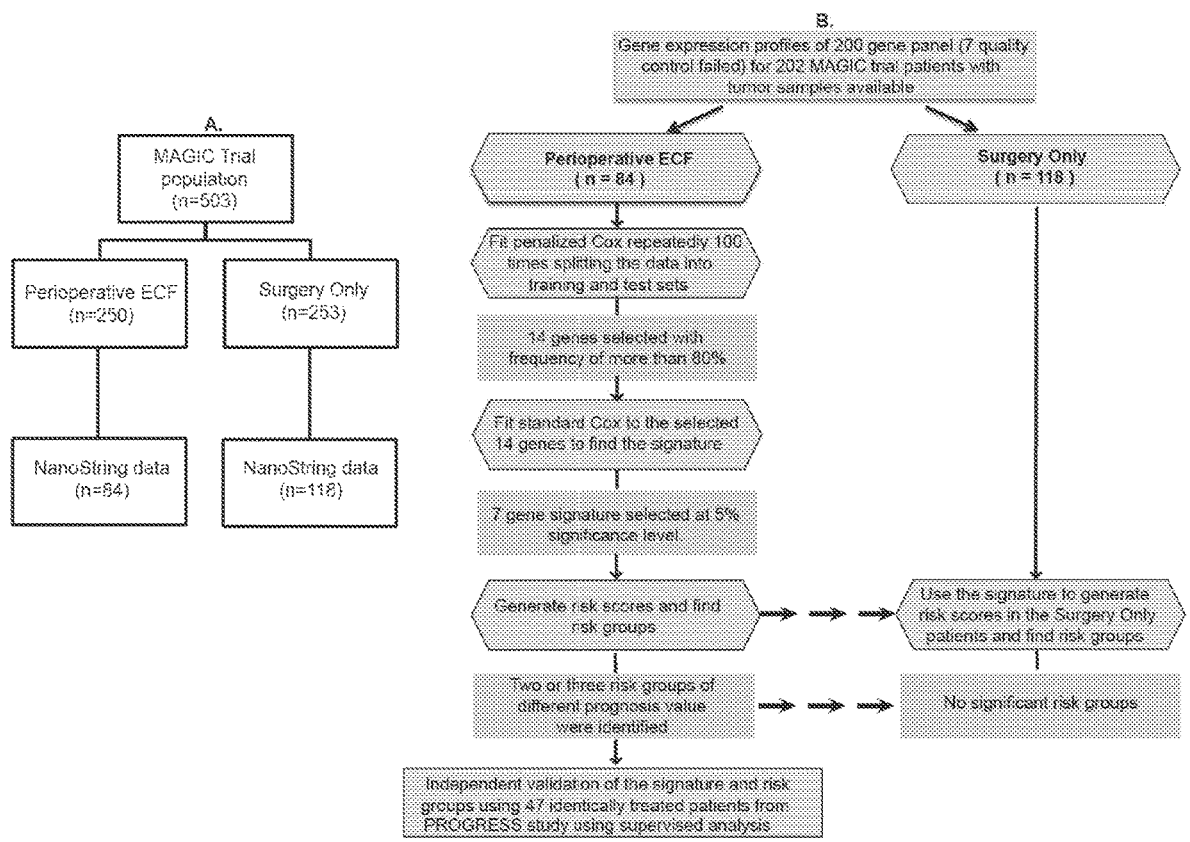
FIG. 8 Consort diagram and flow chart of statistical methods. A. CONSORT diagram highlighting which of the MAGIC trial patients had samples taken and included in this study. B. Flow chart showing the statistical pipeline followed to select genes, find risk groups and validate them. NanoString represents nCounter assay from NanoString Technologies.

Formalin-fixed paraffin-embedded (FFPE) resection specimens (n=202 with high quality RNA) with clinico-pathological information were available for gene profile analysis from those patients randomized within the MAGIC trial (n=503; FIG. 8A).[5] The validation cohort consists of a prospectively collected database of resected gastroesophageal cancer patient samples at the Royal Marsden Hospital (RMH) and Guys and St Thomas Hospital (GSTT) in London, United Kingdom.[6] From this database a translational protocol (PROGRESS) was funded by the RMH and Institute of Cancer Research/National Institute of Cancer Research Biomedical Research Centre. Approval was obtained from institutional review boards (MAGIC: IRAS 11/LO/0566; PROGRESS: IRAS 15/EE/0228).

Gene Expression Profiling

The samples from MAGIC trial were profiled for two hundred genes (including 110 characterising intrinsic gastric cancer subtypes; others were genes frequently amplified/deleted in gastroesophageal cancer or related to chemotherapy sensitivity[7, 8]) and PROGRESS (subset of genes from above) study were profiled using NanoString platform (see Supplementary Methods for more details on RNA isolation, NanoString methods, and quality control measures [9]).

Gene Selection and Risk Group Identification

The pipeline employed to stratify patients into different risk groups is highlighted in FIG. 8B. Firstly, genes expressed in at least 75% of the samples were selected. Genes associated with OS in the perioperative group were identified using penalized Cox regression[10] by repeatedly splitting (100 times) the data into training/testing random sets and selecting genes with frequency of more than 80% occurrence as potential markers for prognosis. Next, a standard Cox regression model was fitted to the expression data of the selected genes to identify robust genes significantly (p<0.05) associated with OS. Finally, the risk score (risk of mortality), $R_i$, for the $i^{th}$ patient in the perioperative group were determined as follows;

$$R_i = \Sigma_{j=1}^{p} \log(\exp[\beta_j]) * X_j$$

where p is the number of selected genes, $\beta_j$ is the regression coefficient (natural-logarithm of hazard ratio; HR) for $X_j$ expression for gene j. The risk scores were then used to stratify patients into different risk groups based on the median cut-off or unsupervised K-means clustering approach. The prognostic value of the risk groups was evaluated using multivariate Cox analysis.

Results

Figure 11:
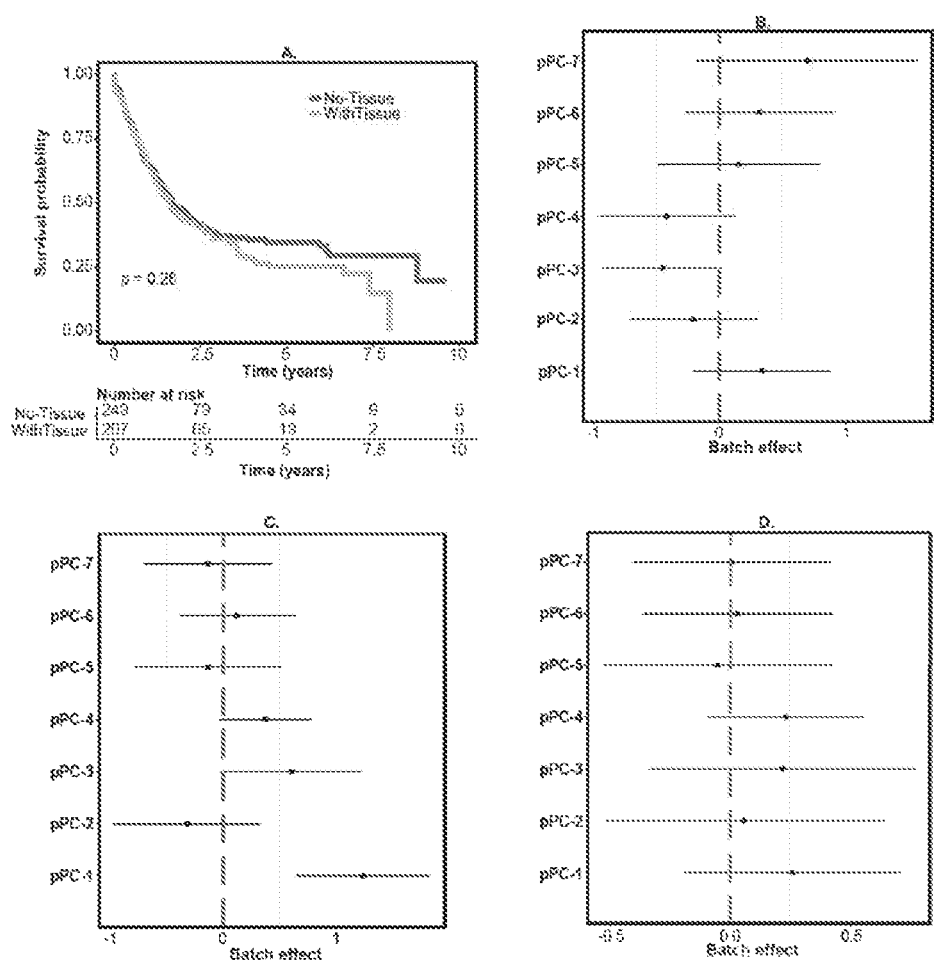
FIG. 11. A. Kaplan-Meier plot showing the comparison of the OS between patients who had tissue available for NanoString analysis (With Tissue) and those who did not (NoTissue). B-D. Forest plots from exploBATCH assessing batch effect: (B.) between different runs of the nCounter data and (C-D.) between pilot and the rest of the nCounter data from MAGIC trial. Forest plot from (C.) shows batch effect before correction and (D.) shows after batch correction using ComBat. If zero is included in the batch effect (x-axis representing confidence interval, there is no batch effect and vice versa).

In the MAGIC trial, 503 patients were randomised to surgery alone or perioperative chemotherapy of which 456 (91%) underwent surgery and had a date of surgery available for survival analysis. There was no significant differences in OS between patients who had tissue available included in this study for nCounter analysis and those who did not (log-rank p=0.3; FIG. 11A). The quality custom nCounter gene expression profile from resected FFPE samples for 202 MAGIC patients was used (see FIG. 8A, CONSORT diagram), and their clinicopathological details are detailed in Table 8.

Using penalized Cox regression analysis in 84 chemotherapy plus surgery treated patients, we identified 14 predictive genes with at least 80% frequency (FIGS. 8B and 9A, FIG. 11B-D and Supplementary Table S1). Standard Cox regression analysis on the selected 14 genes resulted in 7 genes (CDH1, ELOVL5, EGFR, PIP5K1B, FGF1, CD44v8.10, and TBCEL; named as GC-RiskAssigner signature), only prognostic in the perioperative chemotherapy group (Supplementary Table S2A). In order to stratify patients into different risk groups, we computed the risk score for each patient, i.e., a numerical measure quantifying the risk of mortality. The risk scores were generated by multiplying the expression values of the seven genes (GC-RiskAssigner) with their corresponding HR (representing the risk associated with each gene). Finally, patients were divided into either two (low/high) or three (low, moderate and high) risk groups based on their risk scores.

Figure 9:
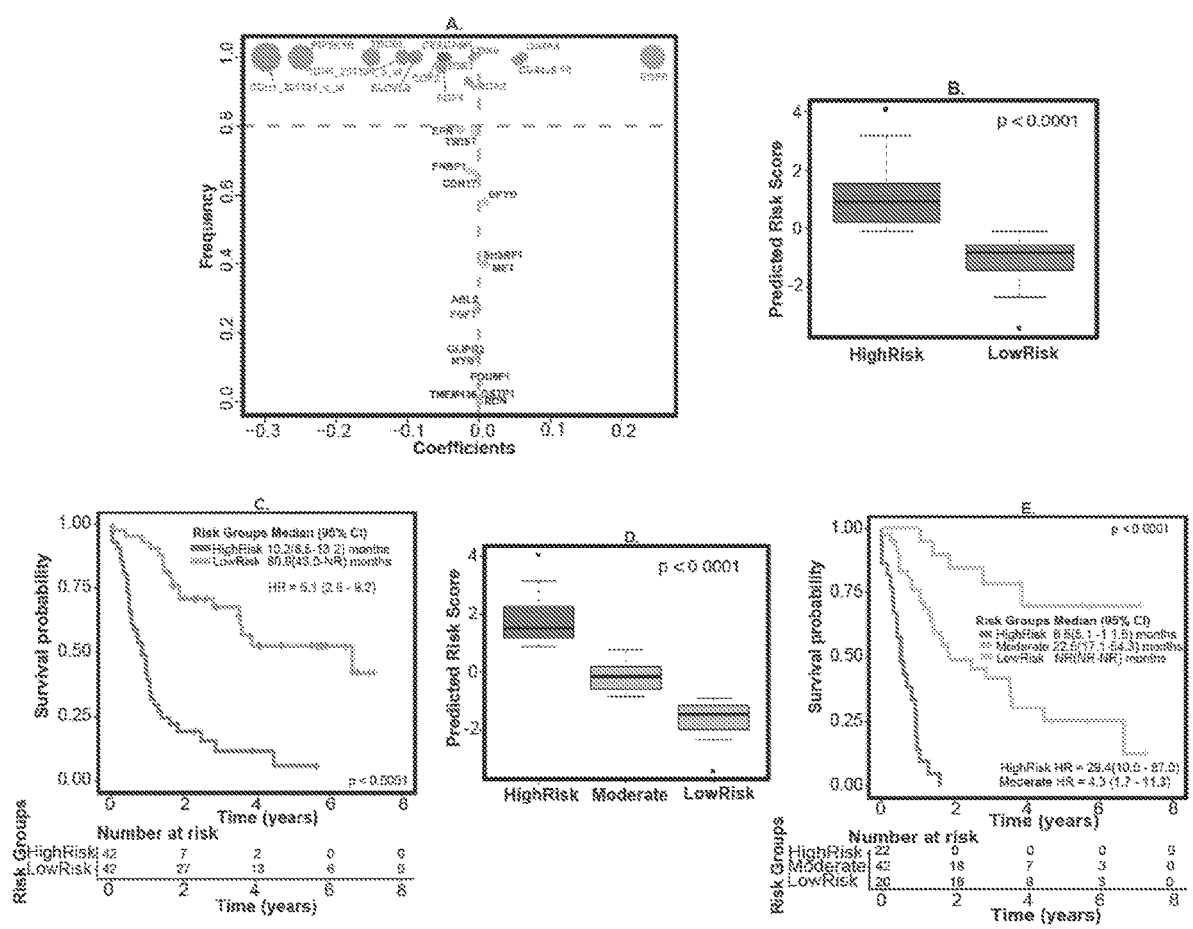
FIG. 9. Gene selection using penalized Cox regression and determination of risk groups in MAGIC perioperative chemotherapy treated patients. A. A plot showing frequency (between 0 and 1) at which genes were selected by penalized Cox regression and the corresponding regression coefficients. Horizontal grey dashed line identifies 14 genes selected at frequency of 0.8. High expression of genes with positive regression coefficients, denoted by red dots, is associated with worst prognosis whilst those in purple are associated with good prognosis. B. A boxplot of risk groups identified by dichotomizing the GC-RiskAssigner risk scores based on median cut-off. C. The Kaplan-Meier plots highlighting the prognostic value of the two risk groups derived using median of risk scores as a cut-off. D-E. A boxplot and Kaplan-Meir plot of three risk groups identified by K-Means clustering.

When patients were dichotomised based on whether they fall into lower half (low-risk) or upper half (high-risk) of their median risk scores (median cut-off) (FIG. 9B), the median OS for the high-risk group was 10.2 months (95% CI of 6.5 to 13.2 months) compared to 80.9 months (95% CI 43.0 months to not assessable) for the low-risk group (HR=5.1 [95% CI of 2.8-9.2]; p<0.0001; FIG. 9C).

Alternatively, when the risk scores were clustered into three risk groups using a clustering method K-means, the median OS for the high-risk group was 6.5 months (95% CI 5.1 to 11.6) and 22.6 months (17.1 to 54.3) for the moderate risk group whilst it was not assessable for the low risk group (FIG. 9D-E, Cox p<0.0001). Rates of one, three and five years OS for patients in both two and three risk groups are shown in Supplementary Table S2B.

Figure 10:
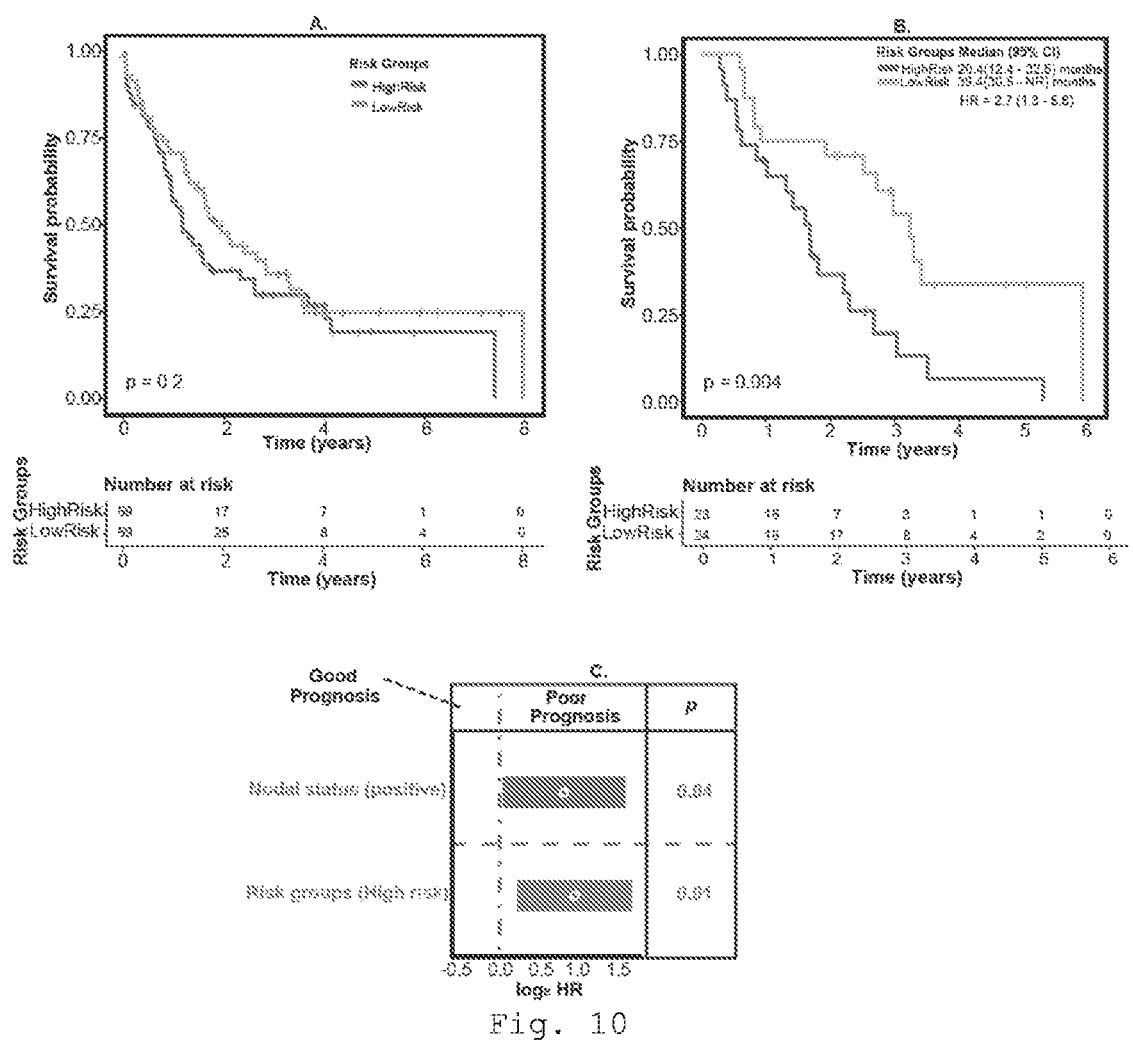
FIG. 10. Determination of the risk groups in the surgery only patients and validation of the risk groups in a validation cohort. A-B. Kaplan-Meier plots showing the difference in OS between (A.) the risk groups from surgery only patients and (B.) the predicted risk groups in the validation cohort, PROGRESS cohort of patients. (C.) Multivariate analysis of risk groups and nodal status for the validation cohort. HR and p denote hazard ratios and p-values, respectively.
Figure 12:
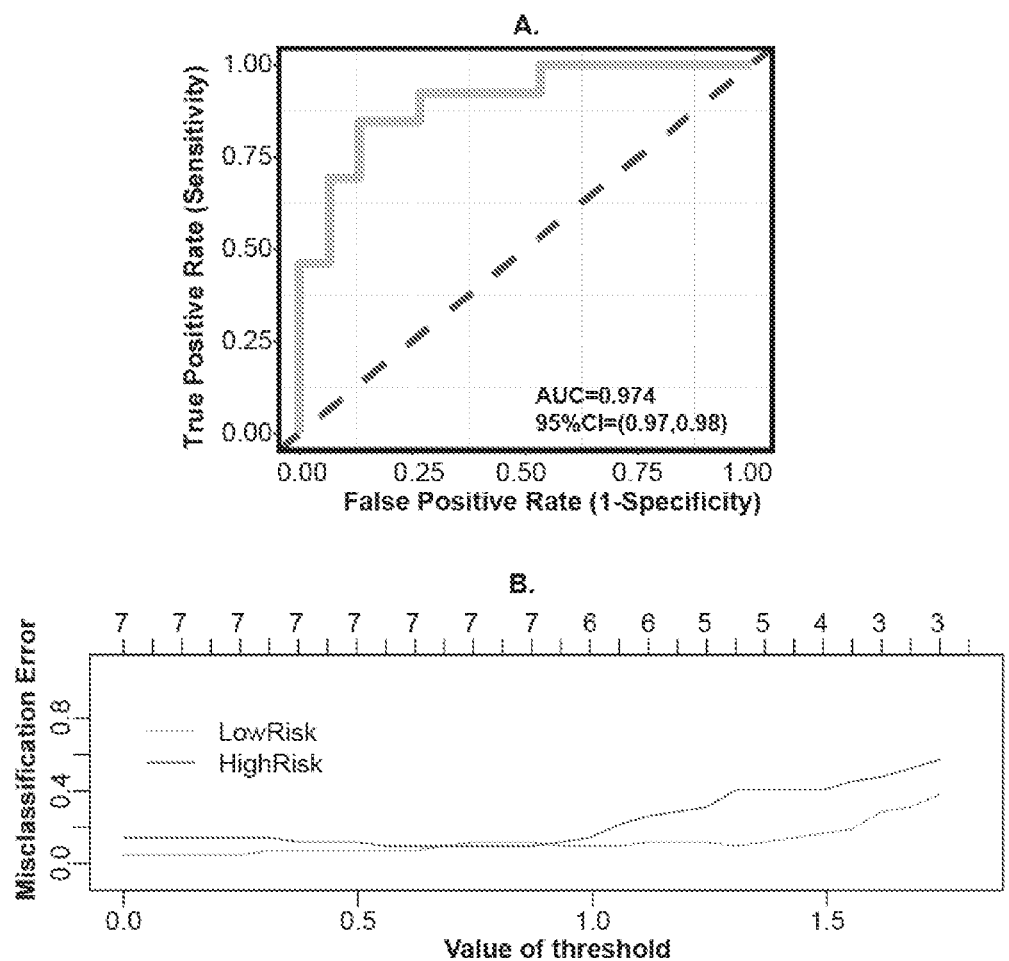
FIG. 12. Plots showing (A.) AUC from ROC curve analysis and (B.) per risk group misclassification error rates of the GC-RiskAssigner PAM centroids from MAGIC cohort of samples.

Multivariate analysis including nodal status was performed to determine if the risk groups were an independent predictor of OS in the perioperative chemotherapy treated patients. Table 9 shows that risk groups remained predictive of OS when controlling for lymph node status, only known confounder of survival.[5] In contrast, when the GC-RiskAssigner was applied to the surgery only patients, none of the 7 genes were associated with OS (Supplementary Table S2A) and there was no significant difference in the OS between the two risk groups derived using median cut-off (log-rank p=0.2; FIG. 10A). We evaluated the performance of the 7 genes from the GC-RiskAssigner signature in predicting the risk groups using receiver operating characteristic (ROC) curve analysis using MAGIC samples. An average area under the curve was high with 0.97 (95% CI of 0.97 and 0.98) as assessed that suggests the robustness of the GC-RiskAssigner signature in predicting the two perioperative risk groups (FIG. 12A). Next, we generated prediction analysis of microarray (PAM[11]) based centroids (which represent the summarized gene expression of each gene in each risk group) for the two median-based risk groups from MAGIC samples (Supplementary Table S3A and FIG. 12B) using the GC-RiskAssigner signature and developed an nCounter platform biomarker assay for the same genes. The patients from the PROGRESS validation cohort (n=47; Table 10) were assigned to the risk groups based on the maximum correlation coefficient values after correlating (Pearson correlation) each patient expression profile with the GC-RiskAssigner signature PAM centroids. The risk of death (HR=2.7; 95% CI 1.3-5.6; p=0.004; FIG. 10B and Supplementary Table S3B) in the high-risk group was almost three times the risk of the low risk group in PROGRESS cohort. The median OS was 20.4 months (95% CI 12.4-32.5) in the high-risk group compared to 39.4 months (95% CI 30.5—not reached) in the low-risk group. Rates of one, three and five years OS for patients in the two predicted risk groups are shown in Supplementary Table S3C. Multivariate analysis of risk score and lymph node metastasis confirmed the independent prognostic value of risk groups (Cox p=0.01) also in the validation cohort (FIG. 10C).

Discussion

Platinum and fluoropyrimidine based perioperative chemotherapy is a common treatment for patients with operable gastroesophageal adenocarcinoma which is endorsed by international guidelines.[4] In this study, patients from MAGIC trial were risk stratified into distinct groups with different survival outcomes following preoperative chemotherapy using a 7-gene (GC-RiskAssigner) signature. These findings were validated in an independent cohort of patients treated with identical chemotherapy plus surgery using our NanoString assay for the GC-RiskAssigner signature. Importantly, risk group based on the GC-RiskAssigner signature provided prognostic information independent of lymph node metastasis, which is the best established prognostic variable so far identified for patients treated with perioperative chemotherapy.[5] These results are potentially important because, in future, clinical trials could be designed using gene signature based risk groups to select the patients most likely to develop recurrent cancer in which to develop novel or more intensive postoperative therapies.

Prognostic gene signatures that predict survival after surgical resection have been validated in other cancers, and have been adopted into routine clinical practice in hormone receptor positive breast cancer and to a lesser extent in colon cancer.[12, 13] These and other prognostic signatures were developed for use in patients who have undergone primary surgery without neoadjuvant chemotherapy and inform the likely benefit from adjuvant chemotherapy based on a recurrence risk calculated on gene expression in an untreated primary tumor.[12-14] A post-chemotherapy gene expression signature was developed in metastatic gastric cancer and validated in a second cohort as prognostic for survival, however to our knowledge this is the first signature which has been developed for patients with resected gastric cancer. [15] Although a gene signature predictive of response to neoadjuvant chemotherapy is the ideal, the frequently scanty tissue available in diagnostic specimens renders this challenging. Therefore, development of a prognostic signature based on post-chemotherapy gene expression profiles that can be measured in the more abundant tissue of the surgical resection may be a pragmatic solution. Dynamic changes in gene expression following chemotherapy have been associated with survival in ovarian cancer pre-clinical models and in breast cancer patients treated in the Investigation of Serial Studies to Predict Your Therapeutic Response with Imaging and Molecular Analysis (I-SPY) trial; [16, 17] however to our knowledge this study is the first to present a prognostic model in patients treated with neoadjuvant chemotherapy for resectable gastroesophageal cancer, and to do so in the context of a randomised clinical trial.

Although the gene panel from which the 7-gene signature was derived contains only 200 genes, these genes were selected for their biologically important roles in gastroesophageal cancer.[7] Importantly, several of the genes included in the signature have been identified a priori as having a prognostic role in gastric cancer. These include EGFR, amplification of which is associated with adverse survival outcomes in several series, and CD44v8-10, a marker of gastric cancer stem cells, which are associated with chemoresistance and worse survival in chemotherapy treated gastric cancer patients.[18-21] Furthermore, although the validation PROGRESS cohort is not a clinical trial dataset, patients in this cohort had been treated with an almost identical chemotherapy to patients in MAGIC. We note that the validation cohort contained more patients with esophageal or junctional cancer, compared to MAGIC, which contains a majority (75%) of gastric cancers. However, this could also be perceived as a strength in terms of the generalizability of the results. As the contribution of each individual chemotherapy component in MAGIC is not known, an appropriate next step would be to validate the prognostic signature in patients who have not received epirubicin, cisplatin and 5-fluorouracil chemotherapy. This is of particular importance because of the recent presentation of the results of the FLOT4-AIO study of perioperative docetaxel, oxaliplatin and 5-fluorouracil (FLOT) which demonstrated improved OS compared to ECF/X chemotherapy[3].

In conclusion, we demonstrate that our signature identified in post-chemotherapy resection specimens from patients with gastroesophageal cancer treated in the MAGIC trial can help to determine prognosis in patients who have been treated with perioperative chemotherapy. Importantly, this signature can be used in conjunction with nodal status to classify patients into risk groups after preoperative chemotherapy. We suggest further exploration of this signature in contemporary trial datasets such as FLOT4-AIO and future design of risk stratified clinical trials to improve survival for patients with resectable gastroesophageal cancer.

Tables for Example 6

TABLE 8

Clinico-pathological characteristics of MAGIC patient cohort

| Variable | Value | Perioperative chemotherapy n = 84 (%) | Surgery only n = 118 (%) |
| --- | --- | --- | --- |
| Sex | Male | 68 (81) | 87 (74) |
|  | Female | 16 (19) | 31 (26) |
| Site of tumor | Stomach | 69 (82) | 95 (80) |
|  | Lower oesophagus | 5 (6) | 9 (8) |
|  | O-G junction | 10 (12) | 14 (12) |
| Age | Median | 64 | 62 |
|  | IQR | 56-70 | 54-70 |
|  | Range | 34-77 | 27-80 |
| Histology | Diffuse | 11 (13) | 26 (22) |
|  | Intestinal | 73 (87) | 85 (72) |
|  | Mixed | 0 (0) | 7 (6) |

TABLE 8-continued

Clinico-pathological characteristics of MAGIC patient cohort

| Variable | Value | Perioperative chemotherapy n = 84 (%) | Surgery only n = 118 (%) |
|---|---|---|---|
| Nodal-status | Yes | 50 (60) | 71 (60) |
| | No | 17 (20) | 21 (18) |
| | NA | 17 (20) | 26 (22) |

O-G, oesophagogastric;
IQR, interquartile range;
NA, not applicable

TABLE 9

Multivariate analysis of overall survival in chemotherapy treated MAGIC patients

| Clinical Variables | Median Based Risk Groups | | K-Means Based Risk Groups | |
|---|---|---|---|---|
| | HR (95% CI) | p | HR (95% CI) | p |
| Nodal status-Yes | 3.6 (1.2-10.7) | 0.02 | 3.5 (1.2-10.3) | 0.03 |
| Risk groups | | | | |
| High risk | 3.6 (1.8-7.2) | 0.0002 | 13.8 (4.5-42.8) | <0.0001 |
| Moderate risk | NA | NA | 5.5 (2.6-11.8) | <0.0001 |

NA, not applicable

TABLE 10

Clinicopathological variables of validation cohort in which all patients received pre-operative ECX chemotherapy

| Variable | Level | n = 47 (%) |
|---|---|---|
| Sex | Male | 44 (94) |
| | Female | 3 (6) |
| Site of tumor | TypeIII OGJ/Stomach | 1 (2) |
| | Lower oesophagus | 6 (13) |
| | Type I/II OGJ | 39 (3) |
| | Not available | 1 (2) |
| Age (years) | Median | 68 |
| | IQR | 60-73 |
| | Range | 42-80 |
| Nodal-status | Yes | 30 (64) |
| | No | 17 (36) |

ECX, epirubicin, cisplatin and capecitabine;
OGJ, oesophagogastric junction;
IQR, interquartile range Supplementary Information to Example 6

Development of GC-RiskAssigner Classifier

In order to develop a classifier to assign future samples into the two risk groups, firstly we performed receiver operating characteristic (ROC) curve analysis to assess the sensitivity and specificity of GC-RiskAssigner in distinguishing the two risk groups. This was carried out by developing the model in the training data and evaluating area under the curve (AUC) in the test dataset. This splitting of data into training and testing set was carried out 100 times to remove sampling bias and the average AUC was presented in FIG. 12A). Secondly, we developed a classifier based on prediction analysis of microarray (PAM)[1] centroids and seven risk score-based (GC-RiskAssigner) genes. The ten-fold cross-validation based PAM analysis in the perioperative chemotherapy treated patients showed eight percent misclassification error rate at a threshold of 0.5595 (FIG. 12B).

Batch Effect Assessment and Correction

In order to assess the batch (or technical) effects between different runs of the nCounter platform experiments or between pilot experimental samples and the rest of the samples from the MAGIC trial, we used our exploBATCH [2] computational tool. exploBATCH contains a tool findBATCH, which uses probabilistic principal component analysis with covariates, to assess batch effects by identifying those principal components that are associated with the given batch information. Those principal components with 95% confidence interval (CI) not containing zero will inform significant batch effect in the data.

Using MAGIC data and runs of the experiments as batch information, FIG. 11B shows no batch effect in the data. On the other hand, FIG. 11C shows significant (95% CI containing no zero) batch effect between pilot and the rest of the samples. Hence, the batch effect between pilot and MAGIC samples was corrected using a computational tool, Combating Batch effect (ComBat)[3]. Further evaluation of batch effect using ComBat corrected data and exploBATCH showed no significant batch effect (FIG. 11D). This ComBat corrected data (n=202) from MAGIC trial were further used for risk score analysis.

In order to assess the batch effect in PROGRESS study samples, we again employed exploBATCH and provided six different experimental runs as batch information. There was no significant batch effect in the PROGRESS dataset (data not shown).

Supplementary Methods

RNA Isolation

Haematoxylin and eosin stained tissue sections were reviewed by a trained pathologist. Resection specimens with >40% of tumor content was chosen for RNA extraction. After deparaffinization, total RNA was extracted using High Pure RNA Paraffin Kit (Roche, Burgess Hill, UK) for MAGIC samples and Ambion Recover All Isolation Kit (Life Technologies, Carlsbad, Calif., USA) for PROGRESS samples, according to the manufacturers' instructions.

Gene Expression Profiling

For the MAGIC data analysis, up to 100 ng of total RNA was hybridized with the custom designed CodeSet of custom genes and processed according to the manufacturer's instructions on the nCounter platform (NanoString Technologies, Seattle, Wash.). The hybridised products were immobilised on sample cartridges in the nCounter Prep Station and colour coded molecular barcodes (NanoString Technologies) were digitally analyzed using nCounter Digital Analyzer (nCounter® Max Analysis System, NanoString Technologies)[4]. Data were collected in Reporter Code Count (RCC) files, and then analyzed using the nSolver 3.0 Analysis Software (NanoString Technologies) according to the manufacturer's instructions. Background subtraction of the geometric mean of 8 negative controls was performed followed by normalization using the geometric mean of 6 positive controls and 3 manually selected housekeeping genes (ACTB, GAPDH and TBP) available in the panel. Five samples (out of 216) with low quality were removed.

For the validation dataset, a new custom panel of 60 genes was designed. This included 23 selected genes for risk score prediction from MAGIC data analysis, the 3 housekeeping genes used in the discovery cohort and further 5 housekeeping genes previously tested with the same platform. We analysed only 23 selected genes in this study.

Custom-designed target-specific oligonucleotide probe pairs for the gene targets were obtained from Integrated DNA Technologies, Inc. (Leuven, Belgium). The targeted sequence of each gene product used in the discovery cohort was maintained for consistency. nCounter Elements™ Tag-Sets were obtained from NanoString Technologies. A modified Elements chemistry protocol (from the manufacturer) was used to perform the hybridization reactions as described.[4] High correlation between standard (used in the discovery cohort) and modified protocols was previously demonstrated.[4] The hybridized products were processed with the nCounter® Max Analysis System and analyzed with nSolver 3.0 Analysis Software similar to MAGIC samples. Those 13 samples that did not pass the quality control as per the manufacturer's criteria from nSolver 3.0 Analysis were not considered in validation cohort.

Prediction Analysis of Microarray (PAM)

PAM is a class prediction computation tool that can also be used to identify a smaller set of genes that best discriminate given class by down weighting noisy genes (not having variable expression across samples). PAM centroids are the average gene expression of each class scaled by variability of that class. PAM centroids can be used for single sample prediction.[5] PAM analysis was performed using R-based pamr tool.[1]

Batch Assessment and Correction

Batch assessment was performed using exploBATCH[2] and correction was done using ComBAT computational tools. More specific information are available in the Supplement Information.

Statistical Analysis

Kaplan-Meier curves were plotted and log-rank test was performed for overall survival analysis. Analysis of variance (ANOVA) was applied to assess the overall effect of each factor in multivariate Cox regression analysis. Wilcoxon sign rank and Kruskal Wallis test was used to test association of risk scores with two or three risk groups, respectively. Wilcoxon sign rank test was also used to find differentially expressed genes.

Supplementary Tables to Example 6

SUPPLEMENTARY TABLE S1

Results from penalized Cox regression applied to the perioperative ECF (Chemotherapy + Surgery) group.

| Genes | Coefficient | Effect | Frequency |
| --- | --- | --- | --- |
| ABL2 | −0.0007703 | −0.4115396 | 0.27 |
| BRCA2 | −0.0152951 | −1.8231342 | 0.93 |
| CD44v8.10 | 0.05315989 | 2.70202811 | 0.99 |

SUPPLEMENTARY TABLE S1-continued

Results from penalized Cox regression applied to the perioperative ECF (Chemotherapy + Surgery) group.

| Genes | Coefficient | Effect | Frequency |
| --- | --- | --- | --- |
| CDH1_201130_s_at | −0.1063832 | −7.864758 | 1 |
| CDH1_201131_s_at | −0.2983063 | −8.5656279 | 1 |
| CDH17 | −0.0035749 | −1.2122637 | 0.66 |
| CDK6 | −0.009653 | −0.9394694 | 1 |
| CEACAM1 | −0.0503185 | −2.841899 | 1 |
| COX2 | −0.0519836 | −2.7357207 | 1 |
| DPYD | 0.00866841 | 0.87082375 | 0.58 |
| EGFR | 0.2434155 | 9.87391443 | 1 |
| ELOVL5 | −0.0884339 | −4.7311532 | 1 |
| EPR | −0.0264551 | −1.2091134 | 0.79 |
| FGF1 | −0.0523678 | −2.0088023 | 0.97 |
| FGF7 | −0.0032074 | −0.3553595 | 0.27 |
| FNBP1 | −0.0137578 | −1.1345559 | 0.67 |
| GATA4 | 0.06043949 | 3.31110885 | 1 |
| GLIPR2 | −0.002237 | −0.3282089 | 0.13 |
| GSTP1 | 0.00013354 | 0.09925671 | 0.01 |
| MET | 0.00611789 | 0.53051012 | 0.4 |
| MYB | −0.0021009 | −0.3342788 | 0.13 |
| OCT4..POU5F1. | 0.00040946 | 0.20560068 | 0.05 |
| PIP5K1B | −0.249377 | −6.6994279 | 1 |
| RON | 6.46E−05 | 0.09847661 | 0.01 |
| SH3RF1 | 0.00930966 | 0.62497889 | 0.4 |
| TBCEL | −0.1510019 | −8.4180691 | 1 |
| TMEM136 | −9.98E−05 | −0.0990075 | 0.01 |
| TOX3 | −0.0454889 | −14.356461 | 1 |
| TWIST | −0.0060228 | −1.4650602 | 0.78 |

SUPPLEMENTARY TABLE S2A

Cox regression p values for seven genes from GC-RiskAssigner in perioperative ECF (Chemotherapy + Surgery) and surgery only groups.
Cox regression statistical p values for seven genes from GC-RiskAssigner in perioperative ECF (Chemotherapy +Surgery) and surgery only groups.

| Genes | Chemotherapy + Surgery p | Surgery Only p |
| --- | --- | --- |
| CDH1_201131_s_at | <0.0001 | 0.237 |
| ELOVL5 | 0.0086 | 0.76 |
| EGFR | <0.0001 | 0.962 |
| PIP5K1B | <0.0001 | 0.614 |
| FGF1 | 0.0084 | 0.739 |
| CD44v8.10 | 0.0091 | 0.925 |
| TBCEL | 0.0292 | 0.458 |

SUPPLEMENTARY TABLE S2B

The probability for one, three and five year overall survival for patients in the perioperative chemotherapy treated group.
The probability for one, three and five year overall survival for patients in the perioperative chemotherapy treated group.

|  | Median cut-off risk groups % (95% CI) | | K-Means clustered risk groups % (95% CI) | | |
| --- | --- | --- | --- | --- | --- |
|  | Low | High | Low | Moderate | High |
| 1 year | 93 (85-100) | 39 (27-57) | 95 (86-100) | 76 (64-90) | 14 (5-41) |
| 3 year | 68 (54-84) | 12 (4-30) | 79 (62-99.8) | 42 (28-61) | 0 |
| 5 year | 53 (38-73) | 6 (1-31) | 70 (50-97) | 25 (13-48) | 0 |

SUPPLEMENTARY TABLE S3A

PAM centroids for the seven-GC-RiskAssigner genes for predicting the two risk groups.

| Genes | Low-Risk | High-Risk |
| --- | --- | --- |
| CDH1_201131_s_at | 0.1357 | −0.1357 |
| ELOVL5 | 0.135 | −0.135 |
| CD44v8.10 | 0.1293 | −0.1293 |
| TBCEL | −0.1045 | 0.1045 |
| PIP5K1B | 0.0928 | −0.0928 |
| FGF1 | −0.0689 | 0.0689 |
| EGFR | 0.0422 | −0.0422 |

SUPPLEMENTARY TABLE S3B

The two risk groups predicted in PROGRESS data using GC-RiskAssigner PAM centroids from (Supplementary Table S3A.) and Pearson correlation.

| Sample IDs | LowRisk | HighRisk | Risk groups |
| --- | --- | --- | --- |
| 1664 | 0.5896557 | −0.5896557 | LowRisk |
| 1678J | −0.6561253 | 0.65612526 | HighRisk |
| 1729 | 0.15370838 | −0.1537084 | LowRisk |
| 1746N | −0.5785698 | 0.57856985 | HighRisk |
| RMH1123 | 0.25188579 | −0.2518858 | LowRisk |
| RMH1151 | −0.6940435 | 0.69404353 | HighRisk |
| 1642J | −0.7025793 | 0.7025793 | HighRisk |
| 1644K | −0.2640054 | 0.26400539 | HighRisk |
| 1658L | 0.14559129 | −0.1455913 | LowRisk |
| 1665K | 0.49317523 | −0.4931752 | LowRisk |
| 1674M | −0.1917976 | 0.19179757 | HighRisk |
| 1705N | −0.3762835 | 0.37628345 | HighRisk |
| 1716N | 0.27384757 | −0.2738476 | LowRisk |
| 1724G | −0.0768169 | 0.07681687 | HighRisk |
| 1653J | −0.1982853 | 0.19828527 | HighRisk |
| 1666R | −0.5849864 | 0.58498636 | HighRisk |

SUPPLEMENTARY TABLE S3B-continued

The two risk groups predicted in PROGRESS data using GC-RiskAssigner PAM centroids from (Supplementary Table S3A.) and Pearson correlation.

| Sample IDs | LowRisk | HighRisk | Risk groups |
| --- | --- | --- | --- |
| 1695M | −0.1530381 | 0.15303808 | HighRisk |
| 1699I | 0.20939173 | −0.2093917 | LowRisk |
| 1734 | 0.02477136 | −0.0247714 | LowRisk |
| 1700N | −0.2211737 | 0.22117367 | HighRisk |
| 1720P | 0.31437504 | −0.314375 | LowRisk |
| 1722R | 0.0419367 | −0.0419367 | LowRisk |
| 1738L | 0.0988467 | −0.0988467 | LowRisk |
| 1763O | −0.0196734 | 0.01967335 | HighRisk |
| 1608GU | 0.17426038 | −0.1742604 | LowRisk |
| 1626M | 0.48316706 | −0.4831671 | LowRisk |
| 1640Q | −0.0053557 | 0.0053557 | HighRisk |
| 1646M | 0.02176589 | −0.0217659 | LowRisk |
| 1669K | 0.33689715 | −0.3368971 | LowRisk |
| 1721K | 0.23312757 | −0.2331276 | LowRisk |
| 1723I | −0.5572429 | 0.55724289 | HighRisk |
| 1728J | 0.19247174 | −0.1924717 | LowRisk |
| 1742OD | −0.2212675 | 0.22126747 | HighRisk |
| 1635K | −0.2030405 | 0.2030405 | HighRisk |
| 1690M | −0.3045958 | 0.3045958 | HighRisk |
| 1698 | 0.33203954 | −0.3320395 | LowRisk |
| 1725J | −0.0822306 | 0.08223061 | HighRisk |
| 1747L | 0.32328035 | −0.3232803 | LowRisk |
| 1769J | 0.3185625 | −0.3185625 | LowRisk |
| 1611T | −0.4605895 | 0.46058948 | HighRisk |
| 1677H | −0.0654176 | 0.06541763 | HighRisk |
| 1692K | 0.34390543 | −0.3439054 | LowRisk |
| 1732D | 0.7214926 | −0.7214926 | LowRisk |
| 1733H | −0.0930023 | 0.09300226 | HighRisk |
| 1735K | 0.37611736 | −0.3761174 | LowRisk |
| 1755N | −0.0791218 | 0.07912181 | HighRisk |
| 1760V | 0.06394561 | −0.0639456 | LowRisk |

SUPPLEMENTARY TABLE S3C

The probability for one, three and five year overall survival for patients in the validation cohort.

| Year | Low-risk % (95% CI) | High-risk % (95% CI) |
| --- | --- | --- |
| 1 year | 75 (60-95) | 70 (53-91) |
| 3 year | 54 (36-81) | 20 (8-49) |
| 5 year | 34 (17-66) | 7 (1-41) |

Example 7—Further Development of Centroids and Replicate Results Tables

Further experimental work with an expanded dataset has led to the following additional results tables and additional centroids.

TABLE 11

Genes associated with overall survival on Cox regression

| Genes | HR | HR_lower | HR_upper | P-value | Improved/worse survival |
| --- | --- | --- | --- | --- | --- |
| CDH1_201131_s_at | 0.5279 | 0.4268 | 0.6528 | <0.0001 | Improved |
| ELOVL5 | 0.6523 | 0.4743 | 0.8971 | 0.0086 | Improved |
| EGFR | 1.5308 | 1.2808 | 1.8297 | <0.0001 | Worse |
| PIP5K1B | 0.537 | 0.4119 | 0.7 | <0.0001 | Improved |
| FGF1 | 0.6604 | 0.485 | 0.8992 | 0.0084 | Improved |
| CD44v8.10 | 1.3418 | 1.0759 | 1.6733 | 0.0091 | Worse |
| TBCEL | 0.6569 | 0.4502 | 0.9584 | 0.0292 | Improved |

TABLE 12

Multivariate analysis of OS in chemotherapy treated patients (2 group model)

| Clinical Variables | Two (Median Based) Risk Groups | |
|---|---|---|
| | HR (95% CI) | p |
| Nodal status-Yes | 3.6 (1.2-10.7) | 0.02 |
| Risk groups | | |
| High risk | 3.6 (1.8-7.2) | 0.0002 |

TABLE 13

Multivariate analysis of OS in chemotherapy treated patients (3 group model)

| Clinical Variables | Three (K-Means Based) Risk Groups | |
|---|---|---|
| | HR (95% CI) | p |
| Nodal status-Yes | 3.5(1.2-10.3) | 0.03 |
| Risk groups | | |
| High risk | 13.8(4.5-42.8) | <0.0001 |
| Moderate risk | 5.5(2.6-11.8) | <0.0001 |

TABLE 14

Prognostic role of gene signature genes in surgery only patients

| Genes | HR | HR_lower | HR_upper | P-value |
|---|---|---|---|---|
| CDH1_201131_s_at | 0.9007 | 0.7575 | 1.071 | 0.237 |
| ELOVL5 | 1.0409 | 0.805 | 1.346 | 0.76 |
| EGFR | 0.995 | 0.8115 | 1.22 | 0.962 |
| PIP5K1B | 1.0524 | 0.8627 | 1.284 | 0.614 |
| FGF1 | 1.0371 | 0.8368 | 1.286 | 0.739 |
| CD44v8.10 | 1.0076 | 0.8602 | 1.18 | 0.925 |
| TBCEL | 0.8872 | 0.6468 | 1.217 | 0.458 |

TABLE 15

Multivariate analysis of overall survival in surgery-only-treated patients (2 group model).

| Clinical Variables | Two (Median Based) Risk Groups | |
|---|---|---|
| | HR (95% CI) | p |
| Nodal status-Yes | 1.9(1.0-3.5) | 0.05 |
| Risk groups | | |
| High risk | 1.5(0.9-2.5) | 0.1 |

Additional Centroids

TABLE 16

Centroids for 2 risk groups and 7 genes

| Genes | Low-Risk | High-Risk |
|---|---|---|
| ELOVL5 | 0.1357 | −0.1357 |
| TBCEL | 0.135 | −0.135 |
| CDH1_201131_s_at | 0.1293 | −0.1293 |
| CD44v8.10 | −0.1045 | 0.1045 |
| PIP5K1B | 0.0928 | −0.0928 |
| EGFR | −0.0689 | 0.0689 |
| FGF1 | 0.0422 | −0.0422 |

TABLE 17

Centroids for 2 risk groups and 29 genes

| Genes | Low-Risk | High-Risk |
|---|---|---|
| ELOVL5 | 0.1967 | −0.1967 |
| TBCEL | 0.1961 | −0.1961 |
| CDH1_201131_s_at | 0.1903 | −0.1903 |
| FGF7 | 0.1737 | −0.1737 |
| CD44v8.10 | −0.1656 | 0.1656 |
| PIP5K1B | 0.1538 | −0.1538 |
| CDK6 | 0.1513 | −0.1513 |
| GLIPR2 | 0.1379 | −0.1379 |
| FNBP1 | 0.1308 | −0.1308 |
| EGFR | −0.1299 | 0.1299 |
| TOX3 | 0.1212 | −0.1212 |
| ABL2 | 0.1179 | −0.1179 |
| CDH1_201130_s_at | 0.1044 | −0.1044 |
| FGF1 | 0.1033 | −0.1033 |
| RON | −0.1003 | 0.1003 |
| CDH17 | 0.0996 | −0.0996 |
| GATA4 | −0.0929 | 0.0929 |
| TWIST | 0.0848 | −0.0848 |
| COX2 | 0.0739 | −0.0739 |
| BRCA2 | 0.0664 | −0.0664 |
| DPYD | 0.0635 | −0.0635 |
| CEACAM1 | 0.0607 | −0.0607 |
| EPR | 0.0568 | −0.0568 |
| MET | −0.0452 | 0.0452 |
| TMEM136 | 0.043 | −0.043 |
| MYB | 0.0206 | −0.0206 |
| SH3RF1 | 0.0129 | −0.0129 |
| OCT4..POU5F1. | 0.0127 | −0.0127 |
| GSTP1 | 0.0043 | −0.0043 |

TABLE 18

Centroids for 3 risk groups and 7 genes

| Genes | High | Low | Moderate |
|---|---|---|---|
| TBCEL | −0.3688 | 0.2627 | 0.0681 |
| EGFR | 0.3531 | −0.1283 | −0.1239 |
| ELOVL5 | −0.3206 | 0.2344 | 0.0563 |
| CDH1_201131_s_at | −0.2778 | 0.3142 | −0.0041 |
| CD44v8.10 | 0.0779 | −0.295 | 0.0997 |
| FGF1 | −0.2371 | 0.2825 | −0.0103 |
| PIP5K1B | −0.2292 | 0.2442 | 0.0037 |

TABLE 19

Centroids for 3 risk groups and 29 genes

| Genes | High | Low | Moderate |
|---|---|---|---|
| TBCEL | −0.3694 | 0.2631 | 0.0682 |
| EGFR | 0.3536 | −0.1285 | −0.1241 |
| FGF7 | −0.3519 | 0.1373 | 0.119 |
| CDH17 | −0.3282 | 0.0807 | 0.1335 |
| ELOVL5 | −0.3212 | 0.2348 | 0.0564 |
| CDH1_201131_s_at | −0.2782 | 0.3146 | −0.0041 |
| TWIST | −0.3039 | 0.0257 | 0.1469 |
| CD44v8.10 | 0.078 | −0.2954 | 0.0998 |
| ABL2 | −0.2104 | 0.2853 | −0.0256 |

TABLE 19-continued

Centroids for 3 risk groups and 29 genes

| Genes | High | Low | Moderate |
|---|---|---|---|
| FGF1 | −0.2375 | 0.283 | −0.0104 |
| CDH1_201130_s_at | −0.1852 | 0.2752 | −0.034 |
| FNBP1 | −0.2645 | 0.1321 | 0.0756 |
| CDK6 | −0.194 | 0.2446 | −0.0149 |
| PIP5K1B | −0.2295 | 0.2446 | 0.0037 |
| TOX3 | −0.227 | 0.1031 | 0.0698 |
| GLIPR2 | −0.2095 | 0.1334 | 0.0462 |
| GATA4 | 0.1937 | 0.0048 | −0.1038 |
| COX2 | −0.1928 | 0.1143 | 0.0466 |
| BRCA2 | −0.188 | 0.0496 | 0.0749 |
| MET | 0.0811 | −0.1698 | 0.0384 |
| OCT4..POU5F1. | −0.0991 | 0.1662 | −0.0272 |
| TMEM136 | −0.0566 | 0.1508 | −0.0421 |
| MYB | −0.1271 | 0.0064 | 0.0635 |
| CEACAM1 | −0.1086 | 0.0886 | 0.0147 |
| GSTP1 | −0.0989 | 0.0172 | 0.0436 |
| RON | 0.0965 | −0.0625 | −0.0208 |
| DPYD | −0.0166 | 0.0506 | −0.0154 |
| EPR | −0.04 | −0.0284 | 0.0345 |
| SH3RF1 | 0.037 | 0.0297 | −0.0336 |

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. Siegel, R. L., K. D. Miller, and A. Jemal, *Cancer statistics,* 2016. CA Cancer J Clin, 2016. 66(1): p. 7-30.
2. Edgren, G., et al., *A global assessment of the oesophageal adenocarcinoma epidemic.* Gut, 2012.
3. Arnold, M., et al., *Recent trends in incidence of five common cancers in 26 European countries since 1988: Analysis of the European Cancer Observatory.* Eur J Cancer, 2015. 51(9): p. 1164-87.
4. Wu, H., et al., *Stomach Carcinoma Incidence Patterns in the United States by Histologic Type and Anatomic Site.* Cancer Epidemiology Biomarkers & Prevention, 2009. 18(7): p. 1945-1952.
5. Forman, D. and V. J. Burley, *Gastric cancer: global pattern of the disease and an overview of environmental risk factors.* Best Pract Res Clin Gastroenterol, 2006. 20(4): p. 633-49.
6. Devesa, S. S., W. J. Blot, and J. F. F. Jr., *Changing patterns in the incidence of esophageal and gastric carcinoma in the United States.* Cancer, 1998. 83(10): p. 2049-2053.
7. Rice, T. W., et al., *Cancer of the esophagus and esophagogastric junction: data-driven staging for the seventh edition of the American Joint Committee on Cancer/International Union Against Cancer Cancer Staging Manuals.* Cancer, 2010. 116(16): p. 3763-73.
8. Washington, K., *7th edition of the AJCC cancer staging manual: stomach.* Ann Surg Oncol, 2010. 17(12): p. 3077-9.
9. *Surgical resection with or without preoperative chemotherapy in oesophageal cancer: a randomised controlled trial.* The Lancet, 2002. 359(9319): p. 1727-1733.
10. Cunningham, D., et al., *Perioperative chemotherapy versus surgery alone for resectable gastroesophageal cancer.* N Engl J Med, 2006. 355(1): p. 11-20.
11. Ychou, M., et al., *Perioperative Chemotherapy Compared With Surgery Alone for Resectable Gastroesophageal Adenocarcinoma: An FNCLCC and FFCD Multicenter Phase III Trial.* Journal of Clinical Oncology, 2011. 29(13): p. 1715-1721.
12. van Hagen, P., et al., *Preoperative Chemoradiotherapy for Esophageal or Junctional Cancer.* New England Journal of Medicine, 2012. 366(22): p. 2074-2084.
13. Macdonald, J. S., et al., *Chemoradiotherapy after surgery compared with surgery alone for adenocarcinoma of the stomach or gastroesophageal junction.* N Engl J Med, 2001. 345(10): p. 725-30.
14. Sakuramoto, S., et al., *Adjuvant chemotherapy for gastric cancer with S-1, an oral fluoropyrimidine.* N Engl J Med, 2007. 357(18): p. 1810-20.
15. Bang, Y. J., et al., *Adjuvant capecitabine and oxaliplatin for gastric cancer after D2 gastrectomy (CLASSIC): a phase 3 open-label, randomised controlled trial.* Lancet, 2012. 379(9813): p. 315-21.
16. Herskovic, A., et al., *Combined chemotherapy and radiotherapy compared with radiotherapy alone in patients with cancer of the esophagus.* N Engl J Med, 1992. 326(24): p. 1593-8.
17. nccn.org/professionals/physician_gls/pdf/gastric.pdf. NCCN Gastric Cancer Guidelines 2015 [cited 2015, 27 Oct.]; Version 3.0:[Available from: nccn.org/professionals/physician_gls/pdf/gastric.pdf
18. Smyth, E. C., et al., *Gastric cancer: ESMO Clinical Practice Guidelines for diagnosis, treatment and follow-up.* Ann Oncol, 2016. 27(suppl 5): p. v38-v49.
19. Cunningham, D., et al., *Capecitabine and Oxaliplatin for Advanced Esophagogastric Cancer.* New England Journal of Medicine, 2008. 358(1): p. 36-46.
20. Findlay, J. M., et al., *Pragmatic staging of oesophageal cancer using decision theory involving selective endoscopic ultrasonography, PET and laparoscopy.* Br J Surg, 2015. 102(12): p. 1488-99.
21. Smyth, E., et al., *A prospective evaluation of the utility of 2-deoxy-2-[(18) F]fluoro-D-glucose positron emission tomography and computed tomography in staging locally advanced gastric cancer.* Cancer, 2012.
22. Leake, P. A., et al., *A systematic review of the accuracy and indications for diagnostic laparoscopy prior to curative-intent resection of gastric cancer.* Gastric Cancer, 2012. 15 Suppl 1: p. S38-47.
23. Cunningham, D., et al., 2201 *Peri-operative chemotherapy ± bevacizumab for resectable gastro-oesophageal adenocarcinoma: Results from the UK Medical Research Council randomised ST03 trial (ISRCTN 46020948).* European Journal of Cancer, 2015. 51: p. 5400.
24. Rice, T., E. Blackstone, and V. Rusch, *7th Edition of the AJCC <i> Cancer Staging Manual:</i> Esophagus and Esophagogastric Junction.* Annals of Surgical Oncology, 2010. 17(7): p. 1721-1724.
25. Alderson, D., et al., *Neoadjuvant chemotherapy for resectable oesophageal and junctional adenocarcinoma: Results from the UK Medical Research Council randomised OEO5 trial (ISRCTN 01852072).* ASCO Meeting Abstracts, 2015. 33(15_suppl): p. 4002.
26. Riddell, A. M., et al., *The appearances of oesophageal carcinoma demonstrated on high-resolution, T2-weighted MRI, with histopathological correlation.* European Radiology, 2007. 17(2): p. 391-399.

27. Kattan, M. W., et al., *Postoperative Nomogram for Disease-Specific Survival After an R0 Resection for Gastric Carcinoma*. Journal of Clinical Oncology, 2003. 21(19): p. 3647-3650.
28. Novotny, A. R., et al., *Predicting individual survival after gastric cancer resection: validation of a U.S.-derived nomogram at a single high-volume center in Europe*. Ann Surg, 2006. 243(1): p. 74-81.
29. Peeters, K. C., et al., *Validation of a nomogram for predicting disease-specific survival after an R0 resection for gastric carcinoma*. Cancer, 2005. 103(4): p. 702-7.
30. Lauren, P., *The Two Main Histological Types of Gastic Carcinoma*. Acta Pathol Microbiol Scand, 1965. 64: p. 31-49.
31. Lee, J. H., et al., *Lauren Histologic Type Is the Most Important Factor Associated With Pattern of Recurrence Following Resection of Gastric Adenocarcinoma*. Ann Surg, 2016.
32. Chen, Y. C., et al., *Clinicopathological Variation of Lauren Classification in Gastric Cancer*. Pathol Oncol Res, 2016. 22(1): p. 197-202.
33. Yu, C. C., et al., *Pathological prognostic factors in the second British Stomach Cancer Group trial of adjuvant therapy in resectable gastric cancer*. Br J Cancer, 1995. 71(5): p. 1106-10.
34. Becker, K., et al., *Significance of histopathological tumor regression after neoadjuvant chemotherapy in gastric adenocarcinomas: a summary of 480 cases*. Ann Surg, 2011. 253(5): p. 934-9.
35. Schmidt, T., et al., *Prognostic value of histopathological regression in 850 neoadjuvantly treated oesophagogastric adenocarcinomas*. Br J Cancer, 2014. 110(7): p. 1712-20.
36. Piessen, G., et al., *Signet ring cell histology is an independent predictor of poor prognosis in gastric adenocarcinoma regardless of tumoral clinical presentation*. Ann Surg, 2009. 250(6): p. 878-87.
37. Messager, M., et al., *The impact of perioperative chemotherapy on survival in patients with gastric signet ring cell adenocarcinoma: a multicenter comparative study*. Ann Surg, 2011. 254(5): p. 684-93; discussion 693.
38. Shibata, A., et al., *Histological classification of gastric adenocarcinoma for epidemiological research: concordance between pathologists*. Cancer Epidemiol Biomarkers Prev, 2001. 10(1): p. 75-8.
39. Hansson, L. E., A. Lindgren, and O. Nyren, *Can endoscopic biopsy specimens be used for reliable Lauren classification of gastric cancer?* Scand J Gastroenterol, 1996. 31(7): p. 711-5.
40. Flucke, U., et al., *Differences between biopsy-or specimen-related Lauren and World Health Organization classification in gastric cancer*. World J Surg, 2002. 26(2): p. 137-40.
41. Blok, P., et al., *Loss of E-cadherin expression in early gastric cancer*. Histopathology, 1999. 34(5): p. 410-5.
42. Shun, C. T., et al., *An immunohistochemical study of E-cadherin expression with correlations to clinicopathological features in gastric cancer*. Hepatogastroenterology, 1998. 45(22): p. 944-9.
43. Forrest, L. M., et al., *Comparison of an inflammation-based prognostic score (GPS) with performance status (ECOG) in patients receiving platinum-based chemotherapy for inoperable non-small-cell lung cancer*. Br J Cancer, 2004. 90(9): p. 1704-6.
44. Petrelli, F., et al., *The Modified Glasgow Prognostic Score and Survival in Colorectal Cancer: A Pooled Analysis of the Literature*. Rev Recent Clin Trials, 2015. 10(2): p. 135-41.
45. La Torre, M., et al., *The glasgow prognostic score as a predictor of survival in patients with potentially resectable pancreatic adenocarcinoma*. Ann Surg Oncol, 2012. 19(9): p. 2917-23.
46. Zhang, C. X., et al., *Association between pretreatment Glasgow prognostic score and gastric cancer survival and clinicopathological features: a meta-analysis*. Onco Targets Ther, 2016. 9: p. 3883-91.
47. Nakayama, Y., et al., *Usefulness of the neutrophil/lymphocyte ratio measured preoperatively as a predictor of peritoneal metastasis in patients with advanced gastric cancer*. Surg Today, 2014. 44(11): p. 2146-52.
48. Shimada, H., et al., *High preoperative neutrophil-lymphocyte ratio predicts poor survival in patients with gastric cancer*. Gastric Cancer, 2010. 13(3): p. 170-6.
49. Urabe, M., H. Yamashita, and Y. Seto, *Pretreatment Neutrophil to Lymphocyte Ratio Independently Predicts Disease-specific Survival in Patients With Resectable Gastroesophageal Junction and Gastric Cancer*. Ann Surg, 2016.
50. Wang, S. C., et al., *Pretreatment Neutrophil to Lymphocyte Ratio Independently Predicts Disease-specific Survival in Resectable Gastroesophageal Junction and Gastric Adenocarcinoma*. Ann Surg, 2016. 263(2): p. 292-7.
51. Xu, Z., et al., *The Prognostic Role of the Platelet-Lymphocytes Ratio in Gastric Cancer: A Meta-Analysis*. PLoS One, 2016. 11(9): p. e0163719.
52. Zheng, D., et al., *The Value of Preoperative Neutrophil to Lymphocyte Ratio in Indicating Lymph Node Metastasis in Patients with Resectable T2 Stage Gastric Adenocarcinoma*. Clin Lab, 2016. 62(4): p. 659-65.
53. Giampieri, R., et al., *Mismatch repair deficiency may affect clinical outcome through immune response activation in metastatic gastric cancer patients receiving first-line chemotherapy*. Gastric Cancer, 2016.
54. Grenader, T., et al., *Prognostic value of neutrophil-to-lymphocyte ratio in advanced oesophago-gastric cancer: exploratory analysis of the REAL-2 trial*. Ann Oncol, 2016. 27(4): p. 687-92.
55. *Comprehensive molecular characterization of gastric adenocarcinoma*. Nature, 2014. 513(7517): p. 202-9.
56. Cristescu, R., et al., *Molecular analysis of gastric cancer identifies subtypes associated with distinct clinical outcomes*. Nat Med, 2015. 21(5): p. 449-56.
57. Yoon, C., et al., *Chemotherapy resistance in diffuse type gastric adenocarcinoma is mediated by RhoA activation in cancer stem-like cells*. Clin Cancer Res, 2015.
58. Choi, Y. Y., et al., *Is microsatellite instability a prognostic marker in gastric cancer?: A systematic review with meta-analysis*. J Surg Oncol, 2014.
59. van Beek, J., et al., *EBV-positive gastric adenocarcinomas: a distinct clinicopathologic entity with a low frequency of lymph node involvement*. J Clin Oncol, 2004. 22(4): p. 664-70.
60. The Cancer Genome Atlas Research, N., *Integrated genomic characterization of oesophageal carcinoma*. Nature, 2017. advance online publication.
61. Hasina, R., et al., *O-6-methylguanine-deoxyribonucleic acid methyltransferase methylation enhances response to temozolomide treatment in esophageal cancer*. Journal of Carcinogenesis, 2013. 12(1): p. 20-20.
62. Yun, T., et al., *Methylation of CHFR sensitizes esophageal squamous cell cancer to docetaxel and paclitaxel*. Genes Cancer, 2015. 6(1-2): p. 38-48.

63. Secrier, M., et al., *Mutational signatures in esophageal adenocarcinoma define etiologically distinct subgroups with therapeutic relevance.* Nat Genet, 2016. 48(10): p. 1131-41.
64. Bang, Y.-J., et al., *Trastuzumab in combination with chemotherapy versus chemotherapy alone for treatment of HER2-positive advanced gastric or gastro-oesophageal junction cancer (ToGA): a phase 3, open-label, randomised controlled trial.* The Lancet, 2010. 376(9742): p. 687-697.
65. Kang, Y., Shah, M A., Atsushi Ohtsu A., *A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC).* J Clin Oncol 2016. 34(Supp 4S): p. Abstr 5.
66. Hecht, J. R., et al., *Lapatinib in Combination With Capecitabine Plus Oxaliplatin in Human Epidermal Growth Factor Receptor 2-Positive Advanced or Metastatic Gastric, Esophageal, or Gastroesophageal Adenocarcinoma: TRIO-013/LOGiC-A Randomized Phase III Trial.* J Clin Oncol, 2016. 34(5): p. 443-51.
67. Lordick, F., et al., *Capecitabine and cisplatin with or without cetuximab for patients with previously untreated advanced gastric cancer (EXPAND): a randomised, open-label phase 3 trial.* Lancet Oncol, 2013. 14(6): p. 490-9.
68. Waddell, T., et al., *Epirubicin, oxaliplatin, and capecitabine with or without panitumumab for patients with previously untreated advanced oesophagogastric cancer (REAL3): a randomised, open-label phase 3 trial.* Lancet Oncol, 2013. 14(6): p. 481-9.
69. Cunningham, D., et al., *Phase III, randomized, double-blind, multicenter, placebo (P)-controlled trial of rilotumumab (R) plus epirubicin, cisplatin and capecitabine (ECX) as first-line therapy in patients (pts) with advanced MET-positive (pos) gastric or gastroesophageal junction (G/GEJ) cancer: RILOMET-1 study.* ASCO Meeting Abstracts, 2015. 33(15_suppl): p. 4000.
70. Shah, M. A., et al., *METGastric: A phase III study of onartuzumab plus mFOLFOX6 in patients with metastatic HER2-negative (HER2-) and MET-positive (MET+) adenocarcinoma of the stomach or gastroesophageal junction (GEC).* ASCO Meeting Abstracts, 2015. 33(15_suppl): p. 4012.
71. Ohtsu, A., et al., *Everolimus for previously treated advanced gastric cancer: results of the randomized, double-blind, phase III GRANITE-1 study.* J Clin Oncol, 2013. 31(31): p. 3935-43.
72. Verma, S., et al., *Trastuzumab Emtansine for HER2-Positive Advanced Breast Cancer.* New England Journal of Medicine, 2012. 367(19): p. 1783-1791.
73. Yoon, H. H., et al., *Adverse Prognostic Impact of Intratumor Heterogeneous HER2 Gene Amplification in Patients With Esophageal Adenocarcinoma.* Journal of Clinical Oncology, 2012. 30(32): p. 3932-3938.
74. Muro, K., et al., *Pembrolizumab for patients with PD-L1-positive advanced gastric cancer (KEYNOTE-012): a multicentre, open-label, phase 1b trial.* Lancet Oncol, 2016.
75. Smyth, E. C. and D. Cunningham, *Encouraging results for PD-1 inhibition in gastric cancer.* Lancet Oncol, 2016. 17(6): p. 682-3.
76. Yuan, J., et al., *Programmed death-ligand-1 expression in advanced gastric cancer detected with RNA in situ hybridization and its clinical significance.* Oncotarget, 2016. 7(26): p. 39671-39679.
77. Fuchs, C. S., et al., *Ramucirumab monotherapy for previously treated advanced gastric or gastro-oesophageal junction adenocarcinoma (REGARD): an international, randomised, multicentre, placebo-controlled, phase 3 trial.* Lancet, 2013.
78. Wilke, H., et al., *Ramucirumab plus paclitaxel versus placebo plus paclitaxel in patients with previously treated advanced gastric or gastro-oesophageal junction adenocarcinoma (RAINBOW): a double-blind, randomised phase 3 trial.* Lancet Oncol, 2014. 15(11): p. 1224-35.
79. Ohtsu, A., et al., *Bevacizumab in combination with chemotherapy as first-line therapy in advanced gastric cancer: a randomized, double-blind, placebo-controlled phase III study.* J Clin Oncol, 2011. 29(30): p. 3968-76.
80. *AJCC Cancer Staging Manual*, S. B. B. Edge, D. R.; Compton, C. C.; Fritz, A. G.; Greene, F. L.; Trotti, A., Editor. 2010.
81. Mansour, J., et al., *Does Graded Histologic Response After Neoadjuvant Chemotherapy Predict Survival for Completely Resected Gastric Cancer?* Annals of Surgical Oncology, 2007. 14(12): p. 3412-3418.
82. Fareed, K. R., et al., *Tumour regression and ERCC1 nuclear protein expression predict clinical outcome in patients with gastro-oesophageal cancer treated with neoadjuvant chemotherapy.* Br J Cancer, 2010. 102(11): p. 1600-1607.
83. Koh, Y. W., et al., *Postoperative Nodal Status and Diffuse-type Histology Are Independent Prognostic Factors in Resectable Advanced Gastric Carcinomas After Preoperative Chemotherapy.* Am J Surg Pathol, 2013. 37(7): p. 1022-9.
84. Noble, F., et al., *Refining pathological evaluation of neoadjuvant therapy for adenocarcinoma of the esophagus.* World J Gastroenterol, 2013. 19(48): p. 9282-93.
85. Mandard, A. M., et al., *Pathologic assessment of tumor regression after preoperative chemoradiotherapy of esophageal carcinoma. Clinicopathologic correlations.* Cancer, 1994. 73(11): p. 2680-6.
86. Smyth, E. C., et al., *Effect of Pathologic Tumor Response and Nodal Status on Survival in the Medical Research Council Adjuvant Gastric Infusional Chemotherapy Trial.* J Clin Oncol, 2016.
87. Fareed, K. R., et al., *Tumour regression grade (TRG) analyses in patients with resectable gastro-oesophageal adenocarcinomas treated with platinum-based neoadjuvant chemotherapy.* Histopathology, 2009. 55(4): p. 399-406.
88. Becker, K., et al., *Histomorphology and grading of regression in gastric carcinoma treated with neoadjuvant chemotherapy.* Cancer, 2003. 98(7): p. 1521-30.
89. Rodel, C., et al., *Prognostic significance of tumor regression after preoperative chemoradiotherapy for rectal cancer.* J Clin Oncol, 2005. 23(34): p. 8688-96.
90. Dworak, O., L. Keilholz, and A. Hoffmann, *Pathological features of rectal cancer after preoperative radiochemotherapy.* Int J Colorectal Dis, 1997. 12(1): p. 19-23.
91. Davies, A. R., et al., *Tumor Stage After Neoadjuvant Chemotherapy Determines Survival After Surgery for Adenocarcinoma of the Esophagus and Esophagogastric Junction.* J Clin Oncol, 2014.
92. Fields, R. C., et al., *Recurrence and survival after pathologic complete response to preoperative therapy followed by surgery for gastric or gastrooesophageal adenocarcinoma.* Br J Cancer, 2011. 104(12): p. 1840-1847.
93. Weber, W. A., et al., *Prediction of Response to Preoperative Chemotherapy in Adenocarcinomas of the Esoph-*

94. Ott, K., et al., *Prediction of Response to Preoperative Chemotherapy in Gastric Carcinoma by Metabolic Imaging: Results of a Prospective Trial.* J Clin Oncol, 2003. 21(24): p. 4604-4610.
95. Lordick, F., et al., *PET to assess early metabolic response and to guide treatment of adenocarcinoma of the oesophagogastric junction: the MUNICON phase II trial.* The Lancet Oncology, 2007. 8(9): p. 797-805.
96. zum Buschenfelde, C. M., et al., *(18)F-FDG PET-guided salvage neoadjuvant radiochemotherapy of adenocarcinoma of the esophagogastric junction: the MUNICON II trial.* J Nucl Med, 2011. 52(8): p. 1189-96.
97. Jiricny, J., *The multifaceted mismatch-repair system.* Nat Rev Mol Cell Biol, 2006. 7(5): p. 335-46.
98. Bhattacharyya, N. P., et al., *Mutator phenotypes in human colorectal carcinoma cell lines.* Proc Natl Acad Sci USA, 1994. 91(14): p. 6319-23.
99. Miguel, C., et al., *Frequent alteration of DNA damage signalling and repair pathways in human colorectal cancers with microsatellite instability.* Oncogene, 2007. 26(40): p. 5919-26.
100. Duval, A. and R. Hamelin, *Mutations at coding repeat sequences in mismatch repair-deficient human cancers: toward a new concept of target genes for instability.* Cancer Res, 2002. 62(9): p. 2447-54.
101. Lynch, H. T., et al., *Hereditary colorectal cancer syndromes: molecular genetics, genetic counseling, diagnosis and management.* Fam Cancer, 2008. 7(1): p. 27-39.
102. Imai, K. and H. Yamamoto, *Carcinogenesis and microsatellite instability: the interrelationship between genetics and epigenetics.* Carcinogenesis, 2008. 29(4): p. 673-80.
103. Kim, J. Y., et al., *Microsatellite instability status in gastric cancer: a reappraisal of its clinical significance and relationship with mucin phenotypes.* Korean J Pathol, 2013. 47(1): p. 28-35.
104. Maekita, T., et al., *High levels of aberrant DNA methylation in Helicobacter pylori-infected gastric mucosae and its possible association with gastric cancer risk.* Clin Cancer Res, 2006. 12(3 Pt 1): p. 989-95.
105. Nakajima, T., et al., *Higher methylation levels in gastric mucosae significantly correlate with higher risk of gastric cancers.* Cancer Epidemiol Biomarkers Prev, 2006. 15(11): p. 2317-21.
106. Niwa, T., et al., *Prevention of Helicobacter pylori-induced gastric cancers in gerbils by a DNA demethylating agent.* Cancer Prev Res (Phila), 2013. 6(4): p. 263-70.
107. Katsurano, M., et al., *Early-stage formation of an epigenetic field defect in a mouse colitis model, and non-essential roles of T-and B-cells in DNA methylation induction.* Oncogene, 2012. 31(3): p. 342-51.
108. Machado, A. M., et al., *Helicobacter pylori infection induces genetic instability of nuclear and mitochondrial DNA in gastric cells.* Clin Cancer Res, 2009. 15(9): p. 2995-3002.
109. Park, D. I., et al., *Effect of Helicobacter pylori infection on the expression of DNA mismatch repair protein.* Helicobacter, 2005. 10(3): p. 179-84.
110. Wilson, P. M., et al., *Standing the test of time: targeting thymidylate biosynthesis in cancer therapy.* Nat Rev Clin Oncol, 2014. 11(5): p. 282-98.
111. Carethers, J. M., et al., *Mismatch Repair Proficiency and In Vitro Response to 5-Fluorouracil.* Gastroenterology, 1999. 117(1): p. 123-131.
112. Tokunaga, E., et al., *Differential growth inhibition by 5-fluorouracil in human colorectal carcinoma cell lines.* Eur J Cancer, 2000. 36(15): p. 1998-2006.
113. Meyers, M., et al., *Role of the hMLH1 DNA mismatch repair protein in fluoropyrimidine-mediated cell death and cell cycle responses.* Cancer Res, 2001. 61(13): p. 5193-201.
114. Tajima, A., et al., *The mismatch repair complex hMutS alpha recognizes 5-fluorouracil-modified DNA: implications for chemosensitivity and resistance.* Gastroenterology, 2004. 127(6): p. 1678-84.
115. Meyers, M., et al., *DNA mismatch repair-dependent response to fluoropyrimidine-generated damage.* J Biol Chem, 2005. 280(7): p. 5516-26.
116. Arnold, C. N., A. Goel, and C. R. Boland, *Role of hMLH1 promoter hypermethylation in drug resistance to 5-fluorouracil in colorectal cancer cell lines.* Int J Cancer, 2003. 106(1): p. 66-73.
117. Sawant, A., et al., *Role of mismatch repair proteins in the processing of cisplatin interstrand cross-links.* DNA Repair (Amst), 2015. 35: p. 126-36.
118. Fink, D., et al., *The role of DNA mismatch repair in platinum drug resistance.* Cancer Res, 1996. 56(21): p. 4881-6.
119. Ribic, C. M., et al., *Tumor Microsatellite-Instability Status as a Predictor of Benefit from Fluorouracil-Based Adjuvant Chemotherapy for Colon Cancer.* New England Journal of Medicine, 2003. 349(3): p. 247-257.
120. Popat, S., R. Hubner, and R. S. Houlston, *Systematic review of microsatellite instability and colorectal cancer prognosis.* J Clin Oncol, 2005. 23(3): p. 609-18.
121. Kim, G. P., et al., *Prognostic and predictive roles of high-degree microsatellite instability in colon cancer: a National Cancer Institute-National Surgical Adjuvant Breast and Bowel Project Collaborative Study.* J Clin Oncol, 2007. 25(7): p. 767-72.
122. Sargent, D. J., et al., *Defective mismatch repair as a predictive marker for lack of efficacy of fluorouracil-based adjuvant therapy in colon cancer.* J Clin Oncol, 2010. 28(20): p. 3219-26.
123. Sinicrope, F. A., et al., *DNA mismatch repair status and colon cancer recurrence and survival in clinical trials of 5-fluorouracil-based adjuvant therapy.* J Natl Cancer Inst, 2011. 103(11): p. 863-75.
124. Network, N.C.C. *Clinical Practice Guidelines in Oncology: Colon Cancer.* 2016, 25 March 2016]; Available from: nccn.org/professionals/physician_gls/pdf/colon.pdf.
125. Shia, J., *Immunohistochemistry versus microsatellite instability testing for screening colorectal cancer patients at risk for hereditary nonpolyposis colorectal cancer syndrome. Part I. The utility of immunohistochemistry.* J Mol Diagn, 2008. 10(4): p. 293-300.
126. Zhang, L., *Immunohistochemistry versus microsatellite instability testing for screening colorectal cancer patients at risk for hereditary nonpolyposis colorectal cancer syndrome. Part II. The utility of microsatellite instability testing.* J Mol Diagn, 2008. 10(4): p. 301-7.
127. Boland, C. R., et al., *A National Cancer Institute Workshop on Microsatellite Instability for cancer detection and familial predisposition: development of international criteria for the determination of microsatellite instability in colorectal cancer.* Cancer Res, 1998. 58(22): p. 5248-57.

128. Suraweera, N., et al., *Evaluation of tumor microsatellite instability using five quasimonomorphic mononucleotide repeats and pentaplex PCR*. Gastroenterology, 2002. 123(6): p. 1804-11.
129. Umar, A., et al., *Revised Bethesda Guidelines for hereditary nonpolyposis colorectal cancer (Lynch syndrome) and microsatellite instability*. J Natl Cancer Inst, 2004. 96(4): p. 261-8.
130. Wirtz, H. C., et al., *Prognostic value and clinicopathological profile of microsatellite instability in gastric cancer*. Clin Cancer Res, 1998. 4(7): p. 1749-54.
131. Warneke, V. S., et al., *Prognostic and putative predictive biomarkers of gastric cancer for personalized medicine*. Diagn Mol Pathol, 2013. 22(3): p. 127-37.
132. Murphy, C., et al., *Alterations in serum prothrombotic markers induced by treatment with bevacizumab-based chemotherapy regimens*. ASCO Meeting Abstracts, 2008. 26(15_suppl): p. 15034.
133. Marrelli, D., et al., *Strong Prognostic Value of Microsatellite Instability in Intestinal Type Non-cardia Gastric Cancer*. Ann Surg Oncol, 2016. 23(3): p. 943-50.
134. Fang, W. L., et al., *Microsatellite instability is associated with a better prognosis for gastric cancer patients after curative surgery*. World J Surg, 2012. 36(9): p. 2131-8.
135. An, J. Y., et al., *Microsatellite instability in sporadic gastric cancer: its prognostic role and guidance for 5-FU based chemotherapy after R0 resection*. Int J Cancer, 2012. 131(2): p. 505-11.
136. Beghelli, S., et al., *Microsatellite instability in gastric cancer is associated with better prognosis in only stage II cancers*. Surgery, 2006. 139(3): p. 347-56.
137. Kim, S. Y., et al., *The benefit of microsatellite instability is attenuated by chemotherapy in stage II and stage III gastric cancer: Results from a large cohort with subgroup analyses*. Int J Cancer, 2015. 137(4): p. 819-25.
138. Yashiro, M., et al., *Allelic imbalance at p53 and microsatellite instability are predictive markers for resistance to chemotherapy in gastric carcinoma*. Ann Surg Oncol, 2009. 16(10): p. 2926-35.
139. Ott, K., et al., *Chromosomal instability rather than p53 mutation is associated with response to neoadjuvant cisplatin-based chemotherapy in gastric carcinoma*. Clin Cancer Res, 2003. 9(6): p. 2307-15.
140. Kim, K. J., et al., *Prognostic implications of tumor-infiltrating FoxP3+ regulatory T cells and CD8+ cytotoxic T cells in microsatellite-unstable gastric cancers*. Hum Pathol, 2014. 45(2): p. 285-93.
141. Howitt, B. E., et al., *Association of Polymerase e-Mutated and Microsatellite-Instable Endometrial Cancers With Neoantigen Load, Number of Tumor-Infiltrating Lymphocytes, and Expression of PD-1 and PD-L1*. JAMA Oncol, 2015. 1(9): p. 1319-23.
142. Verma, R., et al., *Lymphocyte depletion and repopulation after chemotherapy for primary breast cancer*. Breast Cancer Res, 2016. 18(1): p. 10.
143. Cicek, M. S., et al., *Quality assessment and correlation of microsatellite instability and immunohistochemical markers among population-and clinic-based colorectal tumors results from the Colon Cancer Family Registry*. J Mol Diagn, 2011. 13(3): p. 271-81.
144. Klarskov, L., et al., *Interobserver variability in the evaluation of mismatch repair protein immunostaining*. Hum Pathol, 2010. 41(10): p. 1387-96.
145. Wahlberg, S. S., et al., *Evaluation of microsatellite instability and immunohistochemistry for the prediction of germ-line MSH2 and MLH1 mutations in hereditary non-polyposis colon cancer families*. Cancer Res, 2002. 62(12): p. 3485-92.
146. Hansen, M. F., et al., *A novel POLE mutation associated with cancers of colon, pancreas, ovaries and small intestine*. Familial Cancer, 2015. 14(3): p. 437-448.
147. Mathiak, M., et al., *Clinicopathologic Characteristics of Microsatellite Instable Gastric Carcinomas Revisited: Urgent Need for Standardization*. Appl Immunohistochem Mol Morphol, 2015.
148. Bindra, R. S., M. E. Crosby, and P. M. Glazer, *Regulation of DNA repair in hypoxic cancer cells*. Cancer Metastasis Rev, 2007. 26(2): p. 249-60.
149. Chang, C. L., et al., *Oxidative stress inactivates the human DNA mismatch repair system*. Am J Physiol Cell Physiol, 2002. 283(1): p. C148-54.
150. Lee, H. S., et al., *Distinct clinical features and outcomes of gastric cancers with microsatellite instability*. Mod Pathol, 2002. 15(6): p. 632-40.
151. Evans, S. C., et al., *Microsatellite instability in esophageal adenocarcinoma*. Cancer Lett, 2004. 212(2): p. 241-51.
152. Falkenback, D., et al., *Defective mismatch-repair as a minor tumorigenic pathway in Barrett esophagus-associated adenocarcinoma*. Cancer Genet Cytogenet, 2005. 157(1): p. 82-6.
153. Ivanova, T., et al., *Integrated epigenomics identifies BMP4 as a modulator of cisplatin sensitivity in gastric cancer*. Gut, 2013. 62(1): p. 22-33.
154. Napieralski, R., et al., *Methylation of tumor-related genes in neoadjuvant-treated gastric cancer: relation to therapy response and clinicopathologic and molecular features*. Clin Cancer Res, 2007. 13(17): p. 5095-102.
155. Li, Y., et al., *Predictive value of CHFR and MLH1 methylation in human gastric cancer*. Gastric cancer: official journal of the International Gastric Cancer Association and the Japanese Gastric Cancer Association, 2015. 18(2): p. 280-287.
156. Haraldsdottir, S., et al., *Patients with colorectal cancer associated with Lynch syndrome and MLH1 promoter hypermethylation have similar prognoses*. Genet Med, 2016. 18(9): p. 863-8.
157. Roth, A. D., et al., *Prognostic role of KRAS and BRAF in stage II and III resected colon cancer: results of the translational study on the PETACC-3, EORTC 40993, SAKK 60-00 trial*. J Clin Oncol, 2010. 28(3): p. 466-74.
158. Okines, A. F., et al., *Biomarker analysis in oesophago-gastric cancer: Results from the REAL5 and Trans-MAGIC trials*. Eur J Cancer, 2013.
159. The Cancer Genome Atlas Research, N., *Comprehensive molecular characterization of gastric adenocarcinoma*. Nature, 2014. advance online publication.
160. Kim, K. J., et al., *Differential clinicopathologic features in microsatellite-unstable gastric cancers with and without MLH1 methylation*. Hum Pathol, 2013. 44(6): p. 1055-64.
161. Sasako, M., et al., *Five-year outcomes of a randomized phase III trial comparing adjuvant chemotherapy with S-1 versus surgery alone in stage II or III gastric cancer*. J Clin Oncol, 2011. 29(33): p. 4387-93.
162. Noh, S. H., et al., *Adjuvant capecitabine plus oxaliplatin for gastric cancer after D2 gastrectomy (CLASSIC): 5-year follow-up of an open-label, randomised phase 3 trial*. Lancet Oncol, 2014. 15(12): p. 1389-96.

163. Arai, T., et al., *Frequent microsatellite instability in papillary and solid-type, poorly differentiated adenocarcinomas of the stomach.* Gastric Cancer, 2013. 16(4): p. 505-12.

164. Chang, M. S., et al., *Epstein-Barr virus, p53 protein, and microsatellite instability in the adenoma-carcinoma sequence of the stomach.* Hum Pathol, 2002. 33(4): p. 415-20.

165. Chang, M. S., et al., *Epstein-Barr virus and microsatellite instability in gastric carcinogenesis.* J Pathol, 2003. 199(4): p. 447-52.

166. Chiaravalli, A. M., et al., *Histotype-based prognostic classification of gastric cancer.* World J Gastroenterol, 2012. 18(9): p. 896-904.

167. Corso, G., et al., *Correlation of microsatellite instability at multiple loci with long-term survival in advanced gastric carcinoma.* Arch Surg, 2009. 144(8): p. 722-7.

168. Falchetti, M., et al., *Gastric cancer with high-level microsatellite instability: target gene mutations, clinicopathologic features, and long-term survival.* Hum Pathol, 2008. 39(6): p. 925-32.

169. Fang, W. L., et al., *Molecular and survival differences between familial and sporadic gastric cancers.* Biomed Res Int, 2013. 2013: p. 396272.

170. Hayden, J. D., et al., *Prognostic significance of microsatellite instability in patients with gastric carcinoma.* Eur J Cancer, 1997. 33(14): p. 2342-6.

171. Kim, H., et al., *High microsatellite instability predicts good prognosis in intestinal-type gastric cancers.* J Gastroenterol Hepatol, 2011. 26(3): p. 585-92.

172. Oki, E., et al., *Chemosensitivity and survival in gastric cancer patients with microsatellite instability.* Ann Surg Oncol, 2009. 16(9): p. 2510-5.

173. Ottini, L., et al., *Microsatellite instability in gastric cancer is associated with tumor location and family history in a high-risk population from Tuscany.* Cancer Res, 1997. 57(20): p. 4523-9.

174. Polom, K., et al., *High-risk and low-risk gastric cancer areas in Italy and its association with microsatellite instability.* J Cancer Res Clin Oncol, 2016. 142(8): p. 1817-24.

175. Seo, H. M., et al., *Clinicopathologic characteristics and outcomes of gastric cancers with the MSI-H phenotype.* J Surg Oncol, 2009. 99(3): p. 143-7.

176. Alving, A. S., et al., *Enzymatic deficiency in primaquine-sensitive erythrocytes.* Science, 1956. 124(3220): p. 484-5.

177. Lee, A. M., et al., *DPYD variants as predictors of 5-fluorouracil toxicity in adjuvant colon cancer treatment (NCCTG N0147).* J Natl Cancer Inst, 2014. 106(12).

178. Campbell, J. M., et al., *Irinotecan-induced toxicity pharmacogenetics: an umbrella review of systematic reviews and meta-analyses.* Pharmacogenomics J, 2016.

179. Hoskins, J. M., L. A. Carey, and H. L. McLeod, *CYP2D6 and tamoxifen: DNA matters in breast cancer.* Nat Rev Cancer, 2009. 9(8): p. 576-586.

180. Goekkurt, E., et al., *Pharmacogenetic Analyses of a Phase III Trial in Metastatic Gastroesophageal Adenocarcinoma With Fluorouracil and Leucovorin Plus Either Oxaliplatin or Cisplatin: A Study of the Arbeitsgemeinschaft Internistische Onkologie.* Journal of Clinical Oncology, 2009. 27(17): p. 2863-2873.

181. Ott, K., et al., *DNA Repair Gene and MTHFR; Gene Polymorphisms as Prognostic Markers in Locally Advanced Adenocarcinoma of the Esophagus or Stomach Treated with Cisplatin and 5-Fluorouracil-Based Neoadjuvant Chemotherapy.* Annals of Surgical Oncology, 2011. 18(9): p. 2688-2698.

182. Kawakami, K., et al., *Prognostic Role of Thymidylate Synthase Polymorphisms in Gastric Cancer Patients Treated with Surgery and Adjuvant Chemotherapy.* Clinical Cancer Research, 2005. 11(10): p. 3778-3783.

183. Peters, G. J., et al., *Sensitivity of human, murine, and rat cells to 5-fluorouracil and 5'-deoxy-5-fluorouridine in relation to drug-metabolizing enzymes.* Cancer Res, 1986. 46(1): p. 20-8.

184. Sakamoto, E., et al., *Orotate phosphoribosyltransferase expression level in tumors is a potential determinant of the efficacy of 5-fluorouracil.* Biochem Biophys Res Commun, 2007. 363(1): p. 216-22.

185. Fujii, R., A. Seshimo, and S. Kameoka, *Relationships between the expression of thymidylate synthase, dihydropyrimidine dehydrogenase, and orotate phosphoribosyltransferase and cell proliferative activity and 5-fluorouracil sensitivity in colorectal carcinoma.* Int J Clin Oncol, 2003. 8(2): p. 72-8.

186. Ichikawa, W., et al., *Orotate phosphoribosyltransferase gene polymorphism predicts toxicity in patients treated with bolus 5-fluorouracil regimen.* Clin Cancer Res, 2006. 12(13): p. 3928-34.

187. Sakurai, Y., et al., *[Predictive value of orotate phosphoribosyltransferase in chemoresistant patients with gastric carcinoma who underwent S-1-based neoadjuvant/adjuvant chemotherapy].* Gan To Kagaku Ryoho, 2008. 35(7): p. 1147-55.

188. Ishikawa, M., T. Miyauchi, and Y. Kashiwagi, *Clinical implications of thymidylate synthetase, dihydropyrimidine dehydrogenase and orotate phosphoribosyl transferase activity levels in colorectal carcinoma following radical resection and administration of adjuvant 5-FU chemotherapy.* BMC Cancer, 2008. 8: p. 188.

189. Suchi, M., et al., *Molecular cloning of the human UMP synthase gene and characterization of point mutations in two hereditary orotic aciduria families.* Am J Hum Genet, 1997. 60(3): p. 525-39.

190. Goekkurt, E., et al., *Pharmacogenetic analyses of a phase III trial in metastatic gastroesophageal adenocarcinoma with fluorouracil and leucovorin plus either oxaliplatin or cisplatin: a study of the arbeitsgemeinschaft internistische onkologie.* J Clin Oncol, 2009. 27(17): p. 2863-73.

191. Tsunoda, A., et al., *Associations of various gene polymorphisms with toxicity in colorectal cancer patients receiving oral uracil and tegafur plus leucovorin: a prospective study.* Ann Oncol, 2011. 22(2): p. 355-61.

192. Wohlhueter, R. M., R. S. McIvor, and P. G. Plagemann, *Facilitated transport of uracil and 5-fluorouracil, and permeation of orotic acid into cultured mammalian cells.* J Cell Physiol, 1980. 104(3): p. 309-19.

193. Diasio, R. B., T. L. Beavers, and J. T. Carpenter, *Familial deficiency of dihydropyrimidine dehydrogenase. Biochemical basis for familial pyrimidinemia and severe 5-fluorouracil-induced toxicity.* J Clin Invest, 1988. 81(1): p. 47-51.

194. Maring, J. G., et al., *Reduced 5-FU clearance in a patient with low DPD activity due to heterozygosity for a mutant allele of the DPYD gene.* Br J Cancer, 2002. 86(7): p. 1028-33.

195. Ezzeldin, H. and R. Diasio, *Dihydropyrimidine dehydrogenase deficiency, a pharmacogenetic syndrome asso-*

196. Morel, A., et al., *Clinical relevance of different dihydropyrimidine dehydrogenase gene single nucleotide polymorphisms on 5-fluorouracil tolerance.* Mol Cancer Ther, 2006. 5(11): p. 2895-904.

197. van Kuilenburg, A. B., R. A. De Abreu, and A. H. van Gennip, *Pharmacogenetic and clinical aspects of dihydropyrimidine dehydrogenase deficiency.* Ann Clin Biochem, 2003. 40(Pt 1): p. 41-5.

198. Offer, S. M., et al., *Comparative functional analysis of DPYD variants of potential clinical relevance to dihydropyrimidine dehydrogenase activity.* Cancer Res, 2014. 74(9): p. 2545-54.

199. Schwab, M., et al., *Role of genetic and nongenetic factors for fluorouracil treatment-related severe toxicity: a prospective clinical trial by the German 5-FU Toxicity Study Group.* J Clin Oncol, 2008. 26(13): p. 2131-8.

200. Van Kuilenburg, A. B., et al., *Increased risk of grade IV neutropenia after administration of 5-fluorouracil due to a dihydropyrimidine dehydrogenase deficiency: high prevalence of the IVS14+1g>a mutation.* Int J Cancer, 2002. 101(3): p. 253-8.

201. Raida, M., et al., *Prevalence of a common point mutation in the dihydropyrimidine dehydrogenase (DPD) gene within the 5'-splice donor site of intron 14 in patients with severe 5-fluorouracil (5-FU)-related toxicity compared with controls.* Clin Cancer Res, 2001. 7(9): p. 2832-9.

202. Deenen, M. J., et al., *Relationship between single nucleotide polymorphisms and haplotypes in DPYD and toxicity and efficacy of capecitabine in advanced colorectal cancer.* Clin Cancer Res, 2011. 17(10): p. 3455-68.

203. Wei, X., et al., *Molecular basis of the human dihydropyrimidine dehydrogenase deficiency and 5-fluorouracil toxicity.* J Clin Invest, 1996. 98(3): p. 610-5.

204. Zhang, H., et al., *[The association between DPYD gene polymorphism and chemotherapeutic toxicity of 5-FU in gastric carcinoma and colonic carcinoma].* Zhonghua Nei Ke Za Zhi, 2007. 46(2): p. 103-6.

205. Teh, L. K., et al., *Potential of dihydropyrimidine dehydrogenase genotypes in personalizing 5-fluorouracil therapy among colorectal cancer patients.* Ther Drug Monit, 2013. 35(5): p. 624-30.

206. Sun, W., et al., *Correlation analysis of peripheral DPYD gene polymorphism with 5-fluorouracil susceptibility and side effects in colon cancer patients.* Int J Clin Exp Med, 2014. 7(12): p. 5857-61.

207. Toffoli, G., et al., *Clinical validity of a DPYD-based pharmacogenetic test to predict severe toxicity to fluoropyrimidines.* International Journal of Cancer, 2015. 137(12): p. 2971-2980.

208. Braun, M. S., et al., *Association of molecular markers with toxicity outcomes in a randomized trial of chemotherapy for advanced colorectal cancer: the FOCUS trial.* J Clin Oncol, 2009. 27(33): p. 5519-28.

209. Ferry, K. V., T. C. Hamilton, and S. W. Johnson, *Increased nucleotide excision repair in cisplatin-resistant ovarian cancer cells: role of ERCC1-XPF.* Biochem Pharmacol, 2000. 60(9): p. 1305-13.

210. Li, Q., et al., *Association between the level of ERCC-1 expression and the repair of cisplatin-induced DNA damage in human ovarian cancer cells.* Anticancer Res, 2000. 20(2a): p. 645-52.

211. Britten, R. A., et al., *ERCC1 expression as a molecular marker of cisplatin resistance in human cervical tumor cells.* Int J Cancer, 2000. 89(5): p. 453-7.

212. Arnould, S., et al., *Cellular determinants of oxaliplatin sensitivity in colon cancer cell lines.* Eur J Cancer, 2003. 39(1): p. 112-9.

213. Li, W., et al., *ERCC1 siRNA ameliorates drug resistance to cisplatin in gastric carcinoma cell lines.* Mol Med Rep, 2014. 9(6): p. 2423-8.

214. Olaussen, K. A., et al., *DNA Repair by ERCC1 in Non-Small-Cell Lung Cancer and Cisplatin-Based Adjuvant Chemotherapy.* New England Journal of Medicine, 2006. 355(10): p. 983-991.

215. Shirota, Y., et al., *ERCC1 and thymidylate synthase mRNA levels predict survival for colorectal cancer patients receiving combination oxaliplatin and fluorouracil chemotherapy.* J Clin Oncol, 2001. 19(23): p. 4298-304.

216. Metzger, R., et al., *ERCC1 mRNA levels complement thymidylate synthase mRNA levels in predicting response and survival for gastric cancer patients receiving combination cisplatin and fluorouracil chemotherapy.* J Clin Oncol, 1998. 16(1): p. 309-16.

217. Friboulet, L., et al., *ERCC1 isoform expression and DNA repair in non-small-cell lung cancer.* N Engl J Med, 2013. 368(12): p. 1101-10.

218. Suk, R., et al., *Polymorphisms in ERCC1 and grade 3 or 4 toxicity in non-small cell lung cancer patients.* Clin Cancer Res, 2005. 11(4): p. 1534-8.

219. Khrunin, A. V., et al., *Genetic polymorphisms and the efficacy and toxicity of cisplatin-based chemotherapy in ovarian cancer patients.* Pharmacogenomics J, 2010. 10(1): p. 54-61.

220. Perez-Ramirez, C., et al., *Pharmacogenetic predictors of toxicity to platinum based chemotherapy in non-small cell lung cancer patients.* Pharmacol Res, 2016. 111: p. 877-884.

221. Kamikozuru, H., et al., *ERCC1 codon 118 polymorphism is a useful prognostic marker in patients with pancreatic cancer treated with platinum-based chemotherapy.* Int J Oncol, 2008. 32(5): p. 1091-6.

222. Yin, M., et al., *ERCC1 and ERCC2 polymorphisms predict clinical outcomes of oxaliplatin-based chemotherapies in gastric and colorectal cancer: a systemic review and meta-analysis.* Clin Cancer Res, 2011. 17(6): p. 1632-40.

223. Wang, Z., et al., *Polymorphisms in ERCC1, GSTs, TS and MTHFR predict clinical outcomes of gastric cancer patients treated with platinum/5-Fu-based chemotherapy: a systematic review.* BMC Gastroenterol, 2012. 12: p. 137.

224. Findlay, J. M., M. R. Middleton, and I. Tomlinson, *A systematic review and meta-analysis of somatic and germline DNA sequence biomarkers of esophageal cancer survival, therapy response and stage.* Ann Oncol, 2015. 26(4): p. 624-44.

225. Xu, Z., et al., *DNA repair protein levels vis-a-vis anticancer drug resistance in the human tumor cell lines of the National Cancer Institute drug screening program.* Anticancer Drugs, 2002. 13(5): p. 511-9.

226. Lunn, R. M., et al., *XPD polymorphisms: effects on DNA repair proficiency.* Carcinogenesis, 2000. 21(4): p. 551-5.

227. Zhang, X., et al., *XRCC1 and XPD genetic polymorphisms and clinical outcomes of gastric cancer patients treated with oxaliplatin-based chemotherapy: a meta-analysis.* Tumour Biol, 2014.

228. Duldulao, M. P., et al., *Gene polymorphisms predict toxicity to neoadjuvant therapy in patients with rectal cancer.* Cancer, 2013. 119(5): p. 1106-12.
229. Ludovini, V., et al., *Association of cytidine deaminase and xeroderma pigmentosum group D polymorphisms with response, toxicity, and survival in cisplatin/gemcitabine-treated advanced non-small cell lung cancer patients.* J Thorac Oncol, 2011. 6(12): p. 2018-26.
230. Li, Y., et al., *Lack of any relationship between chemotherapy toxicity in non-small cell lung cancer cases and polymorphisms in XRCC1 codon 399 or XPD codon 751.* Asian Pac J Cancer Prev, 2011. 12(3): p. 739-42.
231. London, R. E., *The structural basis of XRCC1-mediated DNA repair.* DNA Repair (Amst), 2015. 30: p. 90-103.
232. Abdel-Fatah, T., et al., *Clinicopathological and functional significance of XRCC1 expression in ovarian cancer.* Int J Cancer, 2013. 132(12): p. 2778-86.
233. Xu, W., et al., *TXNL1-XRCC1 pathway regulates cisplatin-induced cell death and contributes to resistance in human gastric cancer.* Cell Death Dis, 2014. 5: p. e1055.
234. Tengstrom, M., et al., *XRCC1 rs25487 polymorphism predicts the survival of patients after postoperative radiotherapy and adjuvant chemotherapy for breast cancer.* Anticancer Res, 2014. 34(6): p. 3031-7.
235. Liu, R., et al., *Influences of ERCC1, ERCC2, XRCC1, GSTP1, GSTT1, and MTHFR polymorphisms on clinical outcomes in gastric cancer patients treated with EOF chemotherapy.* Tumour Biol, 2016. 37(2): p. 1753-62.
236. Cui, Z., et al., *Association between polymorphisms in XRCC1 gene and clinical outcomes of patients with lung cancer: a meta-analysis.* BMC Cancer, 2012. 12: p. 71.
237. Grimminger, P. P., et al., *XRCC1 gene polymorphism for prediction of response and prognosis in the multimodality therapy of patients with locally advanced rectal cancer.* J Surg Res, 2010. 164(1): p. e61-6.
238. Ruzzo, A., et al., *Genetic markers for toxicity of adjuvant oxaliplatin and fluoropyrimidines in the phase III TOSCA trial in high-risk colon cancer patients.* Sci Rep, 2014. 4: p. 6828.
239. Peng, Y., et al., *Association of DNA base excision repair genes (OGG1, APE1 and XRCC1) polymorphisms with outcome to platinum-based chemotherapy in advanced nonsmall-cell lung cancer patients.* Int J Cancer, 2014. 135(11): p. 2687-96.
240. Liu, Y. P., et al., *Genetic polymorphisms of ERCC1118, XRCC1399 and GSTP1105 are associated with the clinical outcome of gastric cancer patients receiving oxaliplatin based adjuvant chemotherapy.* Mol Med Rep, 2013. 7(6): p. 1904-11.
241. Depeille, P., et al., *Combined effects of GSTP1 and MRP1 in melanoma drug resistance.* Br J Cancer, 2005. 93(2): p. 216-23.
242. Zhang, *GSTP1 determines cis-platinum cytotoxicity in gastric adenocarcinoma MGC803 cells: regulation by promoter methylation and extracellular regulated kinase signaling.* Anti-Cancer Drugs, 2009. 20(3): p. 208-214.
243. Joshi, M. B., et al., *High gene expression of TS1, GSTP1, and ERCC1 are risk factors for survival in patients treated with trimodality therapy for esophageal cancer.* Clin Cancer Res, 2005. 11(6): p. 2215-21.
244. Yamamoto, Y., et al., *Significance of GSTP1 for predicting the prognosis and chemotherapeutic efficacy in esophageal squamous cell carcinoma.* Oncol Rep, 2013. 30(4): p. 1687-94.
245. Ali-Osman, F., et al., *Molecular cloning, characterization, and expression in Escherichia coli of full-length cDNAs of three human glutathione S-transferase Pi gene variants. Evidence for differential catalytic activity of the encoded proteins.* J Biol Chem, 1997. 272(15): p. 10004-12.
246. Johansson, A.-S., et al., *Structure-activity relationships and thermal stability of human glutathione transferase P1-1 governed by the H-site residue 105.* Journal of Molecular Biology, 1998. 278(3): p. 687-698.
247. Shen, X., et al., *Predictive value of GSTP1 Ile105Val polymorphism in clinical outcomes of chemotherapy in gastric and colorectal cancers: a systematic review and meta-analysis.* Cancer Chemother Pharmacol, 2016. 77(6): p. 1285-302.
248. Yao, S., et al., *Gene polymorphisms in cyclophosphamide metabolism pathway, treatment-related toxicity, and disease-free survival in SWOG 8897 clinical trial for breast cancer.* Clin Cancer Res, 2010. 16(24): p. 6169-76.
249. McLeod, H. L., et al., *Pharmacogenetic predictors of adverse events and response to chemotherapy in metastatic colorectal cancer: results from North American Gastrointestinal Intergroup Trial N9741.* J Clin Oncol, 2010. 28(20): p. 3227-33.
250. Sommer, H. and D. V. Santi, *Purification and amino acid analysis of an active site peptide from thymidylate synthetase containing covalently bound 5-fluoro-2'-deoxyuridylate and methylenetetrahydrofolate.* Biochem Biophys Res Commun, 1974. 57(3): p. 689-95.
251. Santi, D. V., C. S. McHenry, and H. Sommer, *Mechanism of interaction of thymidylate synthetase with 5-fluorodeoxyuridylate.* Biochemistry, 1974. 13(3): p. 471-81.
252. Johnston, P. G., et al., *The role of thymidylate synthase expression in prognosis and outcome of adjuvant chemotherapy in patients with rectal cancer.* J Clin Oncol, 1994. 12(12): p. 2640-7.
253. Yeh, K. H., et al., *High expression of thymidylate synthase is associated with the drug resistance of gastric carcinoma to high dose 5-fluorouracil-based systemic chemotherapy.* Cancer, 1998. 82(9): p. 1626-31.
254. Wang, W., et al., *Pharmacogenomic dissection of resistance to thymidylate synthase inhibitors.* Cancer Res, 2001. 61(14): p. 5505-10.
255. Ma, T., et al., *Correlation of thymidylate synthase, thymidine phosphorylase and dihydropyrimidine dehydrogenase with sensitivity of gastrointestinal cancer cells to 5-fluorouracil and 5-fluoro-2'-deoxyuridine.* World J Gastroenterol, 2004. 10(2): p. 172-6.
256. Horie, N., et al., *Functional analysis and DNA polymorphism of the tandemly repeated sequences in the 5'-terminal regulatory region of the human gene for thymidylate synthase.* Cell Struct Funct, 1995. 20(3): p. 191-7.
257. Kawakami, K., et al., *Polymorphic tandem repeats in the thymidylate synthase gene is associated with its protein expression in human gastrointestinal cancers.* Anticancer Res, 1999. 19(4b): p. 3249-52.
258. Etienne, M. C., et al., *Prognostic value of tumoral thymidylate synthase and p53 in metastatic colorectal cancer patients receiving fluorouracil-based chemotherapy: phenotypic and genotypic analyses.* J Clin Oncol, 2002. 20(12): p. 2832-43.
259. Ott, K., et al., *The thymidylate synthase tandem repeat promoter polymorphism: A predictor for tumor-related survival in neoadjuvant treated locally advanced gastric cancer.* Int J Cancer, 2006. 119(12): p. 2885-94.

260. Iacopetta, B., et al., *A polymorphism in the enhancer region of the thymidylate synthase promoter influences the survival of colorectal cancer patients treated with 5-fluorouracil*. Br J Cancer, 2001. 85(6): p. 827-30.
261. Lecomte, T., et al., *Thymidylate synthase gene polymorphism predicts toxicity in colorectal cancer patients receiving 5-fluorouracil-based chemotherapy*. Clin Cancer Res, 2004. 10(17): p. 5880-8.
262. Seo, B. G., et al., *Comprehensive analysis of excision repair complementation group 1, glutathione S-transferase, thymidylate synthase and uridine diphosphate glucuronosyl transferase 1A1 polymorphisms predictive for treatment outcome in patients with advanced gastric cancer treated with FOLFOX or FOLFIRI*. Oncol Rep, 2009. 22(1): p. 127-36.
263. Hoban, P. R., et al., *Reduced topoisomerase II and elevated alpha class glutathione S-transferase expression in a multidrug resistant CHO cell line highly cross-resistant to mitomycin C*. Biochem Pharmacol, 1992. 43(4): p. 685-93.
264. Chao, C. C., et al., *Overexpression of glutathione S-transferase and elevation of thiol pools in a multidrug-resistant human colon cancer cell line*. Mol Pharmacol, 1992. 41(1): p. 69-75.
265. Ott, K., et al., *Glutathione-transferase P1, T1 and M1 genetic polymorphisms in neoadjuvant-treated locally advanced gastric cancer: GSTM1-present genotype is associated with better prognosis in completely resected patients*. International Journal of Colorectal Disease, 2008. 23(8): p. 773-782.
266. Naoe, T., et al., *Prognostic significance of the null genotype of glutathione S-transferase-T1 in patients with acute myeloid leukemia: increased early death after chemotherapy*. Leukemia, 2002. 16(2): p. 203-8.
267. Davies, S. M., et al., *Glutathione S-Transferase Polymorphisms and Outcome of Chemotherapy in Childhood Acute Myeloid Leukemia*. Journal of Clinical Oncology, 2001. 19(5): p. 1279-1287.
268. Romero, R. Z., et al., *Potential application of GSTT1-null genotype in predicting toxicity associated to 5-fluouracil irinotecan and leucovorin regimen in advanced stage colorectal cancer patients*. Oncol Rep, 2006. 16(3): p. 497-503.
269. Zhang, S., et al., *Technical Reproducibility of Single-Nucleotide and Size-Based DNA Biomarker Assessment Using DNA Extracted from Formalin-Fixed, Paraffin-Embedded Tissues*. J Mol Diagn, 2015.
270. Goekkurt, E., et al., *Polymorphisms of glutathione S-transferases (GST) and thymidylate synthase (TS)-novel predictors for response and survival in gastric cancer patients*. Br J Cancer, 2005. 94(2): p. 281-286.
271. Huang, K., et al., *Evaluation of effects of thymidylate synthase and excision repair cross-complementing 1 polymorphisms on chemotherapy outcome in patients with gastrointestinal tumors using peripheral venous blood*. Oncol Lett, 2016. 11(5): p. 3477-3482.
272. Han, S.-W., et al., *Epidermal growth factor receptor intron 1 CA dinucleotide repeat polymorphism and survival of advanced gastric cancer patients treated with cetuximab plus modified FOLFOX6*. Cancer Science, 2010. 101(3): p. 793-799.
273. Mandola, M. V., et al., *A Novel Single Nucleotide Polymorphism within the 5′ Tandem Repeat Polymorphism of the Thymidylate Synthase Gene Abolishes USF-1 Binding and Alters Transcriptional Activity*. Cancer Research, 2003. 63(11): p. 2898-2904.
274. Meulendijks, D., et al., *Clinical relevance of DPYD variants c.1679T>G, c.1236G>A/HapB3, and c.1601G>A as predictors of severe fluoropyrimidine-associated toxicity: a systematic review and meta-analysis of individual patient data*. Lancet Oncol, 2015. 16(16): p. 1639-50.
275. Ho, T. V. and O. D. Scharer, *Translesion DNA synthesis polymerases in DNA interstrand crosslink repair*. Environ Mol Mutagen, 2010. 51(6): p. 552-66.
276. Hoeijmakers, J. H., J. M. Egly, and W. Vermeulen, *TFIIH: a key component in multiple DNA transactions*. Curr Opin Genet Dev, 1996. 6(1): p. 26-33.
277. Sung, P., et al., *Human xeroderma pigmentosum group D gene encodes a DNA helicase*. Nature, 1993. 365 (6449): p. 852-5.
278. Macerelli, M., et al., *Can the response to a platinum-based therapy be predicted by the DNA repair status in non-small cell lung cancer?* Cancer Treatment Reviews, 2016. 48: p. 8-19.
279. Krivak, T. C., et al., *Relationship Between ERCC1 Polymorphisms, Disease Progression, and Survival in the Gynecologic Oncology Group Phase III Trial of Intraperitoneal Versus Intravenous Cisplatin and Paclitaxel for Stage III Epithelial Ovarian Cancer*. Journal of Clinical Oncology, 2008. 26(21): p. 3598-3606.
280. Bohanes, P., M. J. LaBonte, and H.-J. Lenz, *A Review of Excision Repair Cross-complementation Group 1 in Colorectal Cancer*. Clinical Colorectal Cancer, 2011. 10(3): p. 157-164.
281. Lambrechts, S., et al., *Genetic variability in drug transport, metabolism or DNA repair affecting toxicity of chemotherapy in ovarian cancer*. BMC Pharmacol Toxicol, 2015. 16: p. 2.
282. Sakano, S., et al., *Nucleotide excision repair gene polymorphisms may predict acute toxicity in patients treated with chemoradiotherapy for bladder cancer*. Pharmacogenomics, 2010. 11(10): p. 1377-87.
283. Ruzzo, A., et al., *Pharmacogenetic Profiling and Clinical Outcome of Patients With Advanced Gastric Cancer Treated With Palliative Chemotherapy*. Journal of Clinical Oncology, 2006. 24(12): p. 1883-1891.
284. Goff, L. W., et al., *Thymidylate synthase genotype-directed chemotherapy for patients with gastric and gastroesophageal junction cancers*. PLoS One, 2014. 9(9): p. e107424.
285. Weekes, C. D., et al., *Thymidylate Synthase (TYMS) Enhancer Region Genotype-Directed Phase II Trial of Oral Capecitabine for 2nd Line Treatment of Advanced Pancreatic Cancer*. Investigational new drugs, 2011. 29(5): p. 1057-1065.
286. Toffoli, G., et al., *Genotype-driven phase I study of irinotecan administered in combination with fluorouracil/leucovorin in patients with metastatic colorectal cancer*. J Clin Oncol, 2010. 28(5): p. 866-71.
287. Kim, K. P., et al., *A phase I study of UGT1A1 *28/*6 genotype-directed dosing of irinotecan (CPT-11) in Korean patients with metastatic colorectal cancer receiving FOLFIRI*. Oncology, 2015. 88(3): p. 164-72.
288. Deenen, M. J., et al., *Upfront Genotyping of DPYD*2A to Individualize Fluoropyrimidine Therapy: A Safety and Cost Analysis*. J Clin Oncol, 2016. 34(3): p. 227-34.
289. Caudle, K. E., et al., *Clinical Pharmacogenetics Implementation Consortium guidelines for dihydropyrimidine dehydrogenase genotype and fluoropyrimidine dosing*. Clin Pharmacol Ther, 2013. 94(6): p. 640-5.

290. Swen, J. J., et al., *Pharmacogenetics: from bench to byte*—an update of guidelines. Clin Pharmacol Ther, 2011. 89(5): p. 662-73.
291. Relling, M. V. and W. E. Evans, *Pharmacogenomics in the clinic.* Nature, 2015. 526(7573): p. 343-350.
292. Yen, J. L. and H. L. McLeod, *Should DPD analysis be required prior to prescribing fluoropyrimidines?* European Journal of Cancer, 2007. 43(6): p. 1011-1016.
293. Rosmarin, D., et al., *Genetic markers of toxicity from capecitabine and other fluorouracil-based regimens: investigation in the QUASAR2 study, systematic review, and meta-analysis.* J Clin Oncol, 2014. 32(10): p. 1031-9.
294. Mandola, M. V., et al., *A 6 bp polymorphism in the thymidylate synthase gene causes message instability and is associated with decreased intratumoral TS mRNA levels.* Pharmacogenetics, 2004. 14(5): p. 319-27.
295. Benjamini, Y. and Y. Hochberg, *Controlling the False Discovery Rate: A Practical and Powerful Approach to Multiple Testing.* Journal of the Royal Statistical Society. Series B (Methodological), 1995. 57(1): p. 289-300.
296. Shah, M. A., et al., *Molecular Classification of Gastric Cancer: A New Paradigm.* Clinical Cancer Research, 2011. 17(9): p. 2693-2701.
297. Ming, S. C., Gastric carcinoma. *A pathobiological classification.* Cancer, 1977. 39(6): p. 2475-85.
298. Tan, I. B., et al., *Intrinsic Subtypes of Gastric Cancer, Based on Gene Expression Pattern, Predict Survival and Respond Differently to Chemotherapy.* Gastroenterology, 2011. 141(2): p. 476-485.e11.
299. Lovmar, L., et al., *Silhouette scores for assessment of SNP genotype clusters.* BMC Genomics, 2005. 6: p. 35.
300. Brunet, J.-P., et al., *Metagenes and molecular pattern discovery using matrix factorization.* Proceedings of the National Academy of Sciences, 2004. 101(12): p. 4164-4169.
301. Lee, D. D. and H. S. Seung, *Learning the parts of objects by non-negative matrix factorization.* Nature, 1999. 401(6755): p. 788-91.
302. Ringner, M., *What is principal component analysis?* Nat Biotech, 2008. 26(3): p. 303-304.
303. Joliffe, I. T. and B. J. Morgan, *Principal component analysis and exploratory factor analysis.* Stat Methods Med Res, 1992. 1(1): p. 69-95.
304. Geiss, G. K., et al., *Direct multiplexed measurement of gene expression with color-coded probe pairs.* Nat Biotechnol, 2008. 26(3): p. 317-25.
305. Masuda, N., et al., *Analysis of chemical modification of RNA from formalin-fixed samples and optimization of molecular biology applications for such samples.* Nucleic Acids Res, 1999. 27(22): p. 4436-43.
306. von Ahlfen, S., et al., *Determinants of RNA quality from FFPE samples.* PLoS One, 2007. 2(12): p. e1261.
307. Reis, P. P., et al., *mRNA transcript quantification in archival samples using multiplexed, color-coded probes.* BMC Biotechnol, 2011. 11: p. 46.
308. Beard, R. E., et al., *Gene expression profiling using nanostring digital RNA counting to identify potential target antigens for melanoma immunotherapy.* Clinical Cancer Research, 2013. 19(18): p. 4941-4950.
309. Lee, H. J., et al., *Prognostic and predictive value of NanoString-based immune-related gene signatures in a neoadjuvant setting of triple-negative breast cancer: relationship to tumor-infiltrating lymphocytes.* Breast Cancer Res Treat, 2015. 151(3): p. 619-27.
310. Stricker, T. P., et al., *Validation of a prognostic multi-gene signature in high-risk neuroblastoma using the high throughput digital NanoString nCounter™ system.* Molecular oncology, 2014. 8(3): p. 669-678.
311. Veldman-Jones, M. H., et al., *Reproducible, quantitative, and flexible molecular subtyping of clinical DLBCL samples using the NanoString nCounter system.* Clinical Cancer Research, 2015. 21(10): p. 2367-2378.
312. Tibshirani, R., et al., *Diagnosis of multiple cancer types by shrunken centroids of gene expression.* Proc Natl Acad Sci USA, 2002. 99(10): p. 6567-72.
313. Sharan, R. N., et al., *Consensus reference gene(s) for gene expression studies in human cancers: end of the tunnel visible?* Cell Oncol (Dordr), 2015. 38(6): p. 419-31.
314. Waggott, D., et al., *NanoStringNorm: an extensible R package for the pre-processing of NanoString mRNA and miRNA data.* Bioinformatics, 2012. 28(11): p. 1546-8.
315. Hoshida, Y., *Nearest template prediction: a single-sample-based flexible class prediction with confidence assessment.* PLoS One, 2010. 5(11): p. e15543.
316. Deng, N., et al., *A comprehensive survey of genomic alterations in gastric cancer reveals systematic patterns of molecular exclusivity and co-occurrence among distinct therapeutic targets.* Gut, 2012.
317. Van Cutsem, E., et al., *HER2 screening data from ToGA: targeting HER2 in gastric and gastroesophageal junction cancer.* Gastric Cancer, 2015. 18(3): p. 476-84.
318. Okines, A. F., et al., *Effect of HER2 on prognosis and benefit from peri-operative chemotherapy in early oesophago-gastric adenocarcinoma in the MAGIC trial.* Ann Oncol, 2013. 24(5): p. 1253-61.
319. Okines, A. F., et al., *Biomarker analysis in oesophago-gastric cancer: Results from the REAL3 and Trans-MAGIC trials.* Eur J Cancer, 2013. 49(9): p. 2116-25.
320. Palli, D., et al., *Reproducibility of histologic classification of gastric cancer.* Br J Cancer, 1991. 63(5): p. 765-8.
321. Songun, I., et al., *Surgical treatment of gastric cancer: 15-year follow-up results of the randomised nationwide Dutch D1D2 trial.* The Lancet Oncology, 2010. 11(5): p. 439-449.
322. Lin, S. J., et al., *Signatures of tumour immunity distinguish Asian and non-Asian gastric adenocarcinomas.* Gut, 2014.
323. Lei, Z., et al., *Identification of molecular subtypes of gastric cancer with different responses to PI3-kinase inhibitors and 5-fluorouracil.* Gastroenterology, 2013. 145(3): p. 554-65.
324. Cristescu, R., et al., *Molecular analysis of gastric cancer identifies subtypes associated with distinct clinical outcomes.* Nat Med, 2015. 21(5): p. 449-456.
325. Secrier, M., et al., *Mutational signatures in esophageal adenocarcinoma define etiologically distinct subgroups with therapeutic relevance.* Nat Genet, 2016.
326. Guinney, J., et al., *The consensus molecular subtypes of colorectal cancer.* 2015. 21(11): p. 1350-6.
327. Goldhirsch, A., et al., *Strategies for subtypes—dealing with the diversity of breast cancer: highlights of the St. Gallen International Expert Consensus on the Primary Therapy of Early Breast Cancer 2011.* Ann Oncol, 2011. 22(8): p. 1736-47.
328. Paik, S., et al., *A multigene assay to predict recurrence of tamoxifen-treated, node-negative breast cancer.* N Engl J Med, 2004. 351(27): p. 2817-26.
329. Simon, R., et al., *Pitfalls in the use of DNA microarray data for diagnostic and prognostic classification.* J Natl Cancer Inst, 2003. 95(1): p. 14-8.

330. Chapman, P. B., et al., *Improved Survival with Vemurafenib in Melanoma with BRAF V600E Mutation*. New England Journal of Medicine, 2011. 364(26): p. 2507-2516.
331. Maemondo, M., et al., *Gefitinib or Chemotherapy for Non-Small-Cell Lung Cancer with Mutated EGFR*. New England Journal of Medicine, 2010. 362(25): p. 2380-2388.
332. Kwak, E. L., et al., *Anaplastic Lymphoma Kinase Inhibition in Non-Small-Cell Lung Cancer*. New England Journal of Medicine, 2010. 363(18): p. 1693-1703.
333. Fontana, E. and E. C. Smyth, *Novel targets in the treatment of advanced gastric cancer: a perspective review*. Ther Adv Med Oncol, 2016. 8(2): p. 113-25.
334. Smyth, E., et al., *A randomised phase II study of perioperative epirubicin, cisplatin and capecitabine (ECX)±lapatinib for operable, HER-2 positive gastric, oesophagogastric junctional (OGJ) or lower oesophageal adenocarcinoma: Results from the UK MRC ST03 lapatinib feasibility study (ISRCTN 46020948)*. Annals of Oncology, 2016. 27(suppl 6).
335. Kim, M. A., et al., *Heterogeneous amplification of ERBB2 in primary lesions is responsible for the discordant ERBB2 status of primary and metastatic lesions in gastric carcinoma*. Histopathology, 2011. 59(5): p. 822-31.
336. Birkman, E. M., et al., *EGFR gene amplification is relatively common and associates with outcome in intestinal adenocarcinoma of the stomach, gastro-oesophageal junction and distal oesophagus*. BMC Cancer, 2016. 16: p. 406.
337. Zhang, F., et al., *Epidermal growth factor receptor expression and gene copy number analysis in gastric carcinoma samples from Chinese patients*. Oncol Lett, 2016. 11(1): p. 173-181.
338. Higaki, E., et al., *Gene copy number gain of EGFR is a poor prognostic biomarker in gastric cancer: evaluation of 855 patients with bright-field dual in situ hybridization (DISH) method*. Gastric Cancer, 2016. 19(1): p. 63-73.
339. Janbabai, G., et al., *The prognostic impact of EGFR, ErbB2 and MET gene amplification in human gastric carcinomas as measured by quantitative Real-Time PCR*. J Cancer Res Clin Oncol, 2015. 141(11): p. 1945-52.
340. Qian, Z., et al., *Whole genome gene copy number profiling of gastric cancer identifies PAK1 and KRAS gene amplification as therapy targets*. Genes Chromosomes Cancer, 2014. 53(11): p. 883-94.
341. Su, X., Zhan, P., Gavine, PR., *FGFR2 amplification has prognostic significance in gastric cancer: results from a large international multicentre study*. British Journal of Cancer 2014. 110, p. 967-975
342. Han, N., et al., *Evaluation of Fibroblast Growth Factor Receptor 2 Expression, Heterogeneity and Clinical Significance in Gastric Cancer*. Pathobiology, 2015. 82(6): p. 269-79.
343. Ahn, S., et al., *FGFR2 in gastric cancer: protein overexpression predicts gene amplification and high H-index predicts poor survival*. Mod Pathol, 2016. 29(9): p. 1095-103.
344. Pearson, A., et al., *High-Level Clonal FGFR Amplification and Response to FGFR Inhibition in a Translational Clinical Trial*. Cancer Discov, 2016.
345. Peng, Z., et al., *Prognostic significance of MET amplification and expression in gastric cancer: a systematic review with meta-analysis*. PLoS ONE, 2014. 9(1): p. e84502.
346. Choi, J., et al., *Analysis of MET mRNA expression in gastric cancers using RNA in situ hybridization assay: its clinical implication and comparison with immunohistochemistry and silver in situ hybridization*. PLoS One, 2014. 9(11): p. e111658.
347. Zhang, L., et al., *A subset of gastric cancers with EGFR amplification and overexpression respond to cetuximab therapy*. Sci Rep, 2013. 3: p. 2992.
348. Shah, M. A., et al., *Effect of Fluorouracil, Leucovorin, and Oxaliplatin With or Without Onartuzumab in HER2-Negative, MET-Positive Gastroesophageal Adenocarcinoma: The METGastric Randomized Clinical Trial*. JAMA Oncol, 2016.
349. Kwak, E. L., et al., *Clinical activity of AMG 337, an oral MET kinase inhibitor, in adult patients (pts) with MET-amplified gastroesophageal junction (GEJ), gastric (G), or esophageal (E) cancer*. ASCO Meeting Abstracts, 2015. 33(3_suppl): p. 1.
350. Bang, Y.-J., et al., *A randomized, open-label phase II study of AZD4547 (AZD) versus Paclitaxel (P) in previously treated patients with advanced gastric cancer (AGC) with Fibroblast Growth Factor Receptor 2 (FGFR2) polysomy or gene amplification (amp): SHINE study*. ASCO Meeting Abstracts, 2015. 33(15_suppl): p. 4014.
351. Gomez-Martin, C., et al., *Level of HER2 gene amplification predicts response and overall survival in HER2-positive advanced gastric cancer treated with trastuzumab*. J Clin Oncol, 2013. 31(35): p. 4445-52.
352. Guilford, P., et al., *E-cadherin germline mutations in familial gastric cancer*. Nature, 1998. 392(6674): p. 402-5.
353. The Cancer Genome Atlas Research, N., *Comprehensive molecular characterization of gastric adenocarcinoma*. Nature, 2014. 513(7517): p. 202-209.
354. Beavon, I. R. G., *The E-cadherin–catenin complex in tumour metastasis*. European Journal of Cancer. 36(13): p. 1607-1620.
355. Yang, A. D., et al., *Chronic oxaliplatin resistance induces epithelial-to-mesenchymal transition in colorectal cancer cell lines*. Clin Cancer Res, 2006. 12(14 Pt 1): p. 4147-53.
356. Shah, A. N., et al., *Development and characterization of gemcitabine-resistant pancreatic tumor cells*. Ann Surg Oncol, 2007. 14(12): p. 3629-37.
357. Hara, J., et al., *Mesenchymal phenotype after chemotherapy is associated with chemoresistance and poor clinical outcome in esophageal cancer*. Oncol Rep, 2014. 31(2): p. 589-96.
358. Kawata, H., et al., *RhoC upregulation is correlated with reduced E-cadherin in human breast cancer specimens after chemotherapy and in human breast cancer MCF-7 cells*. Horm Cancer, 2014. 5(6): p. 414-23.
359. The Cancer Genome Atlas Research, N., *Integrated genomic characterization of oesophageal carcinoma*. Nature, 2017. 541(7636): p. 169-175.
360. Kim, S. H., et al., *Upregulated expression of BCL2, MCM7, and CCNE1 indicate cisplatin-resistance in the set of two human bladder cancer cell lines: T24 cisplatin sensitive and T24R2 cisplatin resistant bladder cancer cell lines*. Investigative and Clinical Urology, 2016. 57(1): p. 63-72.
361. Bar, J., et al., *miR Profiling Identifies Cyclin-Dependent Kinase 6 Downregulation as a Potential Mechanism of Acquired Cisplatin Resistance in Non-Small-Cell Lung Carcinoma*. Clin Lung Cancer, 2015. 16(6): p. e121-9.

362. Li, B., et al., *Knockdown of CDK6 enhances glioma sensitivity to chemotherapy*. Oncol Rep, 2012. 28(3): p. 909-14.
363. Generali, D., et al., *COX-2 expression is predictive for early relapse and aromatase inhibitor resistance in patients with ductal carcinoma in situ of the breast, and is a target for treatment*. Br J Cancer, 2014. 111(1): p. 46-54.
364. Kim, H. S., et al., *COX2 overexpression is a prognostic marker for Stage III breast cancer*. Breast Cancer Res Treat, 2012. 132(1): p. 51-9.
365. Meyer, S., et al., *Cyclooxygenase 2 (COX2) and Peroxisome Proliferator-Activated Receptor Gamma (PPARG) Are Stage-Dependent Prognostic Markers of Malignant Melanoma*. PPAR Res, 2009. 2009: p. 848645.
366. Wang, Y. and M. Wang, *Prognostic significance of expression of cysteine-rich 61 and cyclooxygenase-2 in gastric cancer*. BMC Gastroenterol, 2016. 16(1): p. 74.
367. Ferrandina, G., et al., *Increased cyclooxygenase-2 (COX-2) expression is associated with chemotherapy resistance and outcome in ovarian cancer patients*. Ann Oncol, 2002. 13(8): p. 1205-11.
368. Ferrandina, G., et al., *Increased cyclooxygenase-2 expression is associated with chemotherapy resistance and poor survival in cervical cancer patients*. J Clin Oncol, 2002. 20(4): p. 973-81.
369. Wulfing, C., et al., *Cyclooxygenase-2 expression in bladder cancer: correlation with poor outcome after chemotherapy*. Eur Urol, 2004. 45(1): p. 46-52.
370. Mercer, S. J., et al., *Rapid up-regulation of cyclooxygenase-2 by 5-fluorouracil in human solid tumors*. Anticancer Drugs, 2005. 16(5): p. 495-500.
371. Rohrig, F. and A. Schulze, *The multifaceted roles of fatty acid synthesis in cancer*. Nat Rev Cancer, 2016. 16(11): p. 732-749.
372. Cai, Y., et al., *Loss of Chromosome 8p Governs Tumor Progression and Drug Response by Altering Lipid Metabolism*. Cancer Cell. 29(5): p. 751-766.
373. Gonzalez-Bengtsson, A., et al., *Estrogen Enhances the Expression of the Polyunsaturated Fatty Acid Elongase Elovl2 via ERalpha in Breast Cancer Cells*. 2016. 11(10): p. e0164241.
374. Phipps, A. I., et al., *Common genetic variation and survival after colorectal cancer diagnosis: a genome-wide analysis*. Carcinogenesis, 2016. 37(1): p. 87-95.
375. Marien, E., et al., *Phospholipid profiling identifies acyl chain elongation as a ubiquitous trait and potential target for the treatment of lung squamous cell carcinoma*. Oncotarget, 2016. 7(11): p. 12582-97.
376. Zheng, R. and G. A. Blobel, *GATA Transcription Factors and Cancer*. Genes & Cancer, 2010. 1(12): p. 1178-1188.
377. Chia, N.Y., et al., *Regulatory crosstalk between lineage-survival oncogenes KLF5, GATA4 and GATA6 cooperatively promotes gastric cancer development*. Gut, 2015. 64(5): p. 707-19.
378. Wen, X. Z., et al., *Methylation of GATA-4 and GATA-5 and development of sporadic gastric carcinomas*. World J Gastroenterol, 2010. 16(10): p. 1201-8.
379. Hellebrekers, D. M., et al., *GATA4 and GATA5 are potential tumor suppressors and biomarkers in colorectal cancer*. Clin Cancer Res, 2009. 15(12): p. 3990-7.
380. Akiyama, Y., et al., *GATA-4 and GATA-5 transcription factor genes and potential downstream antitumor target genes are epi genetically silenced in colorectal and gastric cancer*. Mol Cell Biol, 2003. 23(23): p. 8429-39.
381. Zhao, Y., X. Mu, and G. Du, *Microtubule-stabilizing agents: New drug discovery and cancer therapy*. Pharmacol Ther, 2016. 162: p. 134-43.
382. Boekelheide, K., M. E. Arcila, and J. Eveleth, *cis-diamminedichloroplatinum (II) (cisplatin) alters microtubule assembly dynamics*. Toxicol Appl Pharmacol, 1992. 116(1): p. 146-51.
383. Yanagie, H., et al., *Improvement of sensitivity to platinum compound with siRNA knockdown of upregulated genes in platinum complex-resistant ovarian cancer cells in vitro*. Biomedicine & Pharmacotherapy, 2009. 63(8): p. 553-560.

References for Example 6

1. Cunningham D, Allum W H, Stenning S P et al. Perioperative chemotherapy versus surgery alone for resectable gastroesophageal cancer. N Engl J Med 2006; 355: 11-20.
2. Ychou M, Boige V, Pignon J-P et al. Perioperative Chemotherapy Compared With Surgery Alone for Resectable Gastroesophageal Adenocarcinoma: An FNCLCC and FFCD Multicenter Phase III Trial. Journal of Clinical Oncology 2011; 29: 1715-1721.
3. Al-Batran S, Homann N, Schmalenberg H, Kopp H. Perioperative chemotherapy with docetaxel, oxaliplatin, and fluorouracil/leucovorin (FLOT) versus epirubicin, cisplatin, and fluorouracil or capecitabine (ECF/ECX) for resectable gastric or gastroesophageal junction (GEJ) adenocarcinoma (FLOT4-AIO): A multicenter, randomized phase 3 trial. J Clin Oncol 2017; 35.
4. Smyth E C, Verheij M, Allum W et al. Gastric cancer: ESMO Clinical Practice Guidelines for diagnosis, treatment and follow-up. Ann Oncol 2016; 27: v38-v49.
5. Smyth E C, Fassan M, Cunningham D et al. Effect of Pathologic Tumor Response and Nodal Status on Survival in the Medical Research Council Adjuvant Gastric Infusional Chemotherapy Trial. J Clin Oncol 2016.
6. Davies A R, Gossage J A, Zylstra J et al. Tumor Stage After Neoadjuvant Chemotherapy Determines Survival After Surgery for Adenocarcinoma of the Esophagus and Esophagogastric Junction. J Clin Oncol 2014.
7. Tan I B, Ivanova T, Lim K H et al. Intrinsic Subtypes of Gastric Cancer, Based on Gene Expression Pattern, Predict Survival and Respond Differently to Chemotherapy. Gastroenterology 2011; 141: 476-485.e411.
8. The Cancer Genome Atlas Research N. Comprehensive molecular characterization of gastric adenocarcinoma. Nature 2014; 513: 202-209.
9. Ragulan C, Eason K, Nyamundanda G et al. A Low-Cost Multiplex Biomarker Assay Stratifies Colorectal Cancer Patient Samples into Clinically-Relevant Subtypes. bioRxiv 2017.
10. Gui J, Li H. Penalized Cox regression analysis in the high-dimensional and low-sample size settings, with applications to microarray gene expression data. Bioinformatics 2005; 21: 3001-3008.
11. Tibshirani R, Hastie T, Narasimhan B, Chu G. Diagnosis of multiple cancer types by shrunken centroids of gene expression. Proceedings of the National Academy of Sciences 2002; 99: 6567-6572.
12. Paik S, Shak S, Tang G et al. A multigene assay to predict recurrence of tamoxifen-treated, node-negative breast cancer. N Engl J Med 2004; 351: 2817-2826.
13. Gray R G, Quirke P, Handley K et al. Validation study of a quantitative multigene reverse transcriptase-polymerase chain reaction assay for assessment of recurrence risk in patients with stage II colon cancer. J Clin Oncol 2011; 29: 4611-4619.
14. Cheong J H, Yang H K, Kim H et al. Predictive test for chemotherapy response in resectable gastric cancer: a multi-cohort, retrospective analysis. Lancet Oncol 2018.
15. Kim H K, Choi I J, Kim C G et al. A gene expression signature of acquired chemoresistance to cisplatin and fluorouracil combination chemotherapy in gastric cancer patients. PLoS One 2011; 6: e16694.
16. Koussounadis A, Langdon S P, Harrison D J, Smith V A. Chemotherapy-induced dynamic gene expression changes in vivo are prognostic in ovarian cancer. Br J Cancer 2014; 110: 2975-2984.
17. Magbanua M J, Wolf D M, Yau C et al. Serial expression analysis of breast tumors during neoadjuvant chemotherapy reveals changes in cell cycle and immune pathways associated with recurrence and response. Breast Cancer Res 2015; 17: 73.
18. Birkman E M, Algars A, Lintunen M et al. EGFR gene amplification is relatively common and associates with outcome in intestinal adenocarcinoma of the stomach, gastro-oesophageal junction and distal oesophagus. BMC Cancer 2016; 16: 406.
19. Higaki E, Kuwata T, Nagatsuma A K et al. Gene copy number gain of EGFR is a poor prognostic biomarker in gastric cancer: evaluation of 855 patients with bright-field dual in situ hybridization (DISH) method. Gastric Cancer 2016; 19: 63-73.
20. Yoon C, Park D J, Schmidt B et al. CD44 expression denotes a subpopulation of gastric cancer cells in which Hedgehog signaling promotes chemotherapy resistance. Clin Cancer Res 2014.
21. Lau W M, Teng E, Chong H S et al. CD44v8-10 is a cancer-specific marker for gastric cancer stem cells. Cancer Res 2014; 74: 2630-2641.

References to Supplementary Information of Example 6

1. Tibshirani R, Hastie T, Narasimhan B, Chu G. Diagnosis of multiple cancer types by shrunken centroids of gene expression. Proceedings of the National Academy of Sciences 2002; 99: 6567-6572.
2. Nyamundanda G, Poudel P, Patil Y, Sadanandam A. A Novel Statistical Method to Diagnose, Quantify and Correct Batch Effects in Genomic Studies. Sci Rep 2017; 7: 10849.
3. Johnson W E, Li C, Rabinovic A. Adjusting batch effects in microarray expression data using empirical Bayes methods. Biostatistics 2007; 8: 118-127.
4. Ragulan C, Eason K, Nyamundanda G et al. A Low-Cost Multiplex Biomarker Assay Stratifies Colorectal Cancer Patient Samples into Clinically-Relevant Subtypes. bioRxiv 2017.
5. Sadanandam A, Lyssiotis C A, Homicsko K et al. A colorectal cancer classification system that associates cellular phenotype and responses to therapy. Nat Med 2013; 19: 619-625.

The invention claimed is:

1. A method of treatment of gastroesophageal cancer in a human patient, said patient having had at least one perioperative treatment with one or more chemotherapeutic agents and having had surgical resection of a gastroesophageal tumour, the method comprising:
   (a) measuring the gene expression of at least the genes CDH1, ELOVL5, EGFR, PIP5K1B, FGF1, CD44 and TBCEL in a sample obtained from the gastroesophageal tumour of the patient to obtain a sample gene expression profile of at least said genes CDH1, ELOVL5, EGFR, PIP5K1B, FGF1, CD44 and TBCEL; and
   (b) deriving a risk score by weighting the measured, and optionally normalised, expression level of each gene and summing the weighted expression level of each of the genes, wherein the contribution to the total risk score made by CD44 and EGFR has the opposite sign to that of the contribution made by CDH1, ELOVL5, PIP5K1B, FGF1 and TBCEL;
   (c) determining from said score that the patient is at high or moderate risk of poor prognosis; and
   (d) following said determining administering therapy to the patient a therapeutically effective amount of at least one chemotherapeutic agent selected from the group consisting of epirubicin, cisplatin, 5-fluorouracil, capecitabine, oxaliplatin, and docetaxel.

* * * * *